(12) United States Patent
Genetta

(10) Patent No.: US 7,078,180 B2
(45) Date of Patent: Jul. 18, 2006

(54) METHODS AND COMPOSITIONS USEFUL FOR DIAGNOSIS, STAGING, AND TREATMENT OF CANCERS AND TUMORS

(75) Inventor: Thomas Genetta, Atlanta, GA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 377 days.

(21) Appl. No.: 10/232,561

(22) Filed: Aug. 30, 2002

(65) Prior Publication Data

US 2003/0119772 A1    Jun. 26, 2003

Related U.S. Application Data

(60) Provisional application No. 60/317,300, filed on Sep. 5, 2001.

(51) Int. Cl.
*G01N 33/574* (2006.01)
(52) U.S. Cl. .................. 435/7.23; 435/7.2; 435/975; 530/350; 536/23.1
(58) Field of Classification Search ................ 435/975, 435/7.2, 7.23; 530/350; 536/23.1
See application file for complete search history.

(56) References Cited

U.S. PATENT DOCUMENTS 4,281,061 A * 7/1981 Zuk et al. .................. 435/7.9

FOREIGN PATENT DOCUMENTS

EP         1394274       *  3/2004

OTHER PUBLICATIONS

Skolnick et al TIBTECH vol. 18 p. 34 (2000).*
Abbott DW et al, "*BRCA1* Expression Restores Radiation Resistance in *BRCA1*-defective Cancer Cells through Enhancement of Transcription-coupled DNA Repair", *J Biol Chem* 1999;274(26):18808-18812.
Zhang Q et al, "Lack of Phosphotyrosine Phosphatase SHP-1 Expression in Malignant T-Cell Lymphoma Cells Results from Methylation of the SHP-1 Promoter", *AM J Pathol* 2000;157(4):1137-1146.
Wang HG et al, "Mechanisms of Bcl-2 protein function", *Histol Histopathol* 1998;13:521-530.
Wang XW, "Role of p53 and Apoptosis in Carcinogenesis", *Anticancer Res* 1999;19;4759-4771.
Welcsh P et al, "Insights into the Functions of BRCA1 and BRCA2", *Trends Genet* 2000;16(2):69-74.
Zhang X et al, "Structure of an XRCC1 BRCT domain: a new protein—protein interaction module", *EMBO J* 1998;17(21):6404-6411.
Huyton T et al, "The BRCA1 C-terminal domain: structure and function", *Mutation Research* 2000;460:319-332.
Inukai T et al, "*SLUG*, a *ces-1*-Related Zinc Finger Transcription Factor Gene with Antiapoptotic Activity, Is a Downstream Target of the E2A-HLF Oncoprotein", *Mol Cell* 1999;4:343-352.
Amrosini G et al, "Induction of apoptosis and Inhibition of Cell Proliferation by *survivin* Gene Targeting", *J Biol Chem* 1998;273(18):11177-11182.
Ambrosini G et al, "A novel anti-apoptosis gene, *survivin*, expressed in cancer and lymphoma", *Mature Medicine* 1997;3(8):917-921.
Arch RH et al, "Tumor necrosis factor receptor-associated factors (TRAFs)—a family of adapter proteins that regulates life and death", *Gene Dev* 1998;12:2821-2830.
Arch RH et al, "Lymphocyte Survival—The Struggle Against Death", *Annu Rev Cell Dev Biol* 1999;15:113-140.
Arnold H et al, "Muscle differentiation: more complexity to the network of myogenic regulators", *Curr Opin Genet Dev* 1998;8:539-544.
Bork P et al, "A superfamily of conserved domain in DNA damage-responsive cell cycle checkpoint proteins", *FASEB J* 1997;11:68-76.
Brabletz T et al, "Negative regulation of CD4 expression in T cells by the transcriptional repressor ZEB", *Int Immunol* 1999;11(10):1701-1708.
Brunet A et al, "Protein Kinase SGK Mediates Survival Signals by Phosphorylating the Forkhead Transcription Factor FKHRL1 (FOXO3a)", *Mol Cell Biol* 2001;21(3):952-965.
Callebaut I et al, "From BRCA1 to RAP1: a widespread BRCT module closely associated with DNA repair", *FEBS Letters* 1997;400:25-30.
Chen F et al, "Role of p53 in Cell Cycle Regulation and apoptosis following Exposure to Proteasome Inhibitors", *Cell Growth & Differentiation* 2000;11:239-246.
Cuevas B et al, "SHP-1 Regulates Lck-induced Phophatidylinositol 3-Kinase Phosphorylation and Activity", *J Biol Chem* 1999;274(39):27583-27589.
Deveraux QL et al, "IAP family proteins—suppressors of apoptosis", *Genes Dev* 1999;13:239-252.
Dragovich T et al, "Signal transduction pathways that regulate cell survival and cell death", *Oncogene* 1998;17:3207-3213.
Fields S et al, "A novel genetic system to detect protein—protein interactions", *Nature* 1989;340:245-246.

(Continued)

*Primary Examiner*—Sheela J. Huff
(74) *Attorney, Agent, or Firm*—Dann Dorfman Herrell and Skillman; Kathleen D. Rigaut

(57) ABSTRACT

Methods, compositions and kits which employ one or more ZEB specific detection reagents for detection and localization of ZEB associated molecules in tumor cells are disclosed. Also provided are methods for determining stage and progression of cancer in a mammal based on alterations in ZEB expression levels and subcellular localization. Also provided are methods for treating a cancer in a mammal by modulating ZEB expression levels and activity.

5 Claims, 24 Drawing Sheets

OTHER PUBLICATIONS

Funahashi J et al, "δ-crystallin enhancer binding protein δEF1 is a zinc finger-homeodomain protein implicated in postgastrulation embryogenesis", *Development* 1993;119:433-446.

Furusawa T et al, "Identification of CtBP1 and CtBP2 as Corepressors of Zinc Finger-Homeodomain Factor δEF1", *Mel Cell Biol* 1999;19(12):8581-8590.

Genetta T et al, "Displacement of an E-Box-Binding Repressor by Basic Helix-Loop-Helix Proteins: Implications for B-Cell Specificity of the Immunoglobulin Heavy-Chain Enhancer", *Mol Cell Biol* 1994;14(9):6153-6163.

Genetta T et al, "Cloning of a cDNA encoding a mouse transcriptional repressor displaying striking sequence conservation across vertebrates", *Gene* 1996;169:289-290.

Gregoire J et al, "T-cell Expression of the Human *GATA-3* Gene is Regulated by a Non-lineage-specific Silencer", *J Biol Chem* 1999;274(10):6567-6578.

Grooteclaes ML et al, "Evidence for a function of CtBP in epithelial gene regulation and anoikis", *Oncogene* 2000;19:3823-3828.

Hemavathy K et al, "Human Slug is a Repressor that Localizes to Sites of Active Transcription", *Mol Cell Biol* 2000;20(14):5087-5095.

Healy JI et al, "Positive versus negative signaling by lymphocyte antigen receptors", *Ann Rev Immunol* 1998;16:645-670.

Hengartner MO et al, "The biochemistry of apoptosis", *Nature* 407:770-776.

Hu Y et al, "Chromatin remodeling and activation of chromosomal DNA replication by an acidic transcriptional activation domain from BRCA1", *Genes Dev* 1999;13:637-642.

Weber BL et al, "transcript identification in the BRCA1 candidate region", *Breast Cancer Res Treat*1995;33:115-124.

Iwabuchi K et al, "Stimulation of p53-mediated transcriptional activation by the p53-binding proteins, 53BP1 and 53BP2", *J Biol Chem* 1998;273(4):26061-26068.

Jacobson MD et al, "Programmed cell death in animal development", *Cell* 1997;88:347-354.

Lakin ND et al, "Regulation of p53 in response to DNA damage", *Oncogene* 1999;18:7644-7655.

Lassar AB et al, "Functional activity of myogenic HLH proteins requires hetero-oligomerization with E12/E47-like proteins *in vivo*", *Cell* 1991;66:305-315.

Lee JE, "Basic helix-loop-helix genes in neural developement", *Curr Opin Neurobiol* 1997;7:13-20.

Lenardo M et al, "Mature T lymphocyte apoptosis—immune regulation in a dynamic and unpredictable antigenic environment", *Annu Rev Immunol* 1999;17:221-253.

Lopez CD et al, "Proapoptotic p53-interacting protein 53BP2 is induced by UV irradiation but suppressed by p53", *Mol Cell Biol* 2000;20(21):8018-8025.

Miyake T et al, "A functional comparison of BRCA1 C-terminal domain in transcription activation and chromatin remodeling", *J Biol Chem* 2000;275(51):40169-40173.

Monteiro Ana et al, "Evidence for a transcriptional activation function of BRCA1 c-terminal region", *PNAS* 1996;93:13595-13599.

Naumovski L et al, "The p53-binding protein 53BP2 also interacts with Bcl2 and impedes cell cycle progression at $G_2/M$", *Mol Cell Biol* 1996;16(7):3884-3892.

Nijhawan D et al, "Apoptosis in neural development and disease", *Annu Rev Neurosci* 2000;23:73-87.

Ono M et al, "Deletion of SHIP or SHP-1 reveals two distinct pathways for inhibitory signaling", *Cell* 1997;90:293-301.

Plas DR et al, "Direct regulation of ZAP-7 by SHP-1 in T cell antigen receptor signaling", *Science* 1996;272:1173-1176.

Postigo AA et al, "ZEB represses transcription through interaction with the corepressor CtBP", *PNAS* 1999;96:6683-6688.

Postigo AA et al, "zfh-1, the *Drosophila* Homologue of ZEB, Is a Transcriptional Repressor That Regulates Somatic Myogenesis", *Mol Cell Biol* 1999;19(10):7255-7263.

Postigo AA et al, "Differential expression and function of members of the *zfh-1* family of zinc finger/homeodomain repressors", *PNAS* 2000;97(12):6391-6396.

Postigo AA et al, "ZEB, a vertebrate homolog of *Drosophila* Zfh-1, is a negative regulator of muscle differentiation", *EMBO J* 1997;16(13):3935-3943.

Prabhu S et al, "Regulation of the expression of cyclin-dependent kinase inhibitor p21 by E2A and Id proteins", *Mol Cell Biol* 1997;17(10):5888-5896.

Aian D et al, "T cell antigen receptor signal transduction", *Curr Opin Cell Biol* 1997;9:205-212.

Rathmell JC et al, "The central effectors of cell death in the immune system", *Annu Rev Immunol* 1999;17:781-828.

Reed JC et al, "Apoptosis and cancer: strategies for integrating programmed cell death", *Siminars in Hematology* 2000;37(4)suppl7:9-16.

Rudin CM et al, "Apoptosis and disease: regulation and clinical relevance of programmed cell death", *Annu Rev Med* 1997;48:267-281.

Sakamuro D et al, "New Myc-interacting proteins: a second Myc network emerges", *Oncogene* 1999;18:2942-2954.

Schmajuk G et al, "Antisense oligonucleotides with different backbones", *J Biol Chem* 1999;274(31):21783-21789.

Schultz LB et al, "p53 Binding Protein 1 (53BP1) is an Early Participant in the Cellular Response to DNA Double-Strand Breaks", *J Cell Biol* 2000;151(7):1381-1390.

Sebzda E et al, "Selection of the T cell repertoire", *Annu Rev Immunol* 1999;17:829-874.

Sekido R et al, "The δ-Crystallin Enhancer-Binding Protein δEF1 Is a Repressor of E2-Box-mediated Gene activation", *Mol Cell Biol* 1994;14(9):5692-5700.

Iwabuchi K et al, "Two cellular proteins that bind to wild-type but not mutant p53", *PNAS* 1994;91:6098-6102.

Sensenbaugh KR et al, "Multiple promoter elements including a novel repressor site modulate expression of the chick ovalbumin gene", *DNA Cell Biol* 1999;18(2):147-156.

Sheikh MS et al, "Role of p53 Family Members in Apoptosis", *J Cell Physiol* 2000;182:171-181.

Siminovitch KA et al, "Regulation of B cell signal transduction by SH2-containing protein-tyrosine phosphatases", *Seminars in Immunology* 1998;10:329-347.

Takagi T et al, "δEF1, a zinc finger and homeodomain transcription factor, is required for skeleton patterning in multiple lineages", *Development* 1998;125:21-31.

Taylor MF et al, "*In vitro* efficacy of morpholino-modified antisense oligomers directed against tumor necrosis factor-α mRNA", *J Biol Chem*, 1996;271(29):17445-17452.

Thangaraju M et al, "BRCA1 facilitates stress-induced apoptosis in breast and ovarian cancer cell lines", *J Biol Chem* 2000;275(43):33487-33496.

Williams TM et al, "Identification of a zinc finger protein that inhibits IL-2 gene expression", *Science* 1991;254:1791-1794.

Xia Z et al, "Negative cell cycle regulation and DNA damage-inducible phosphorylation of the BRCT protein 53BP1", *J Biol Chem* 2001;276(4):2708-2718.

Yasui DH et al, "Transcriptional repression of the IL-2 gene in Th cells by ZEB", *J Immunol* 1998;160:4433-4440.

\* cited by examiner

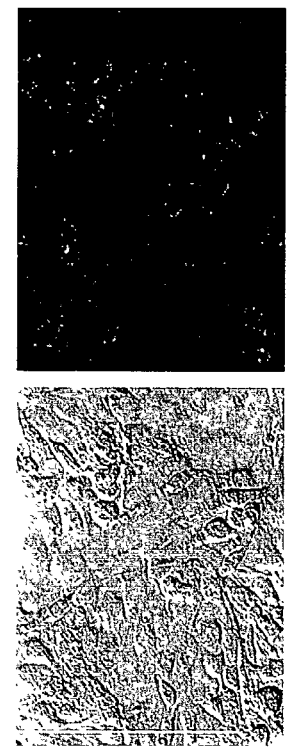
Fig. 4B  Missense
Fig. 4D
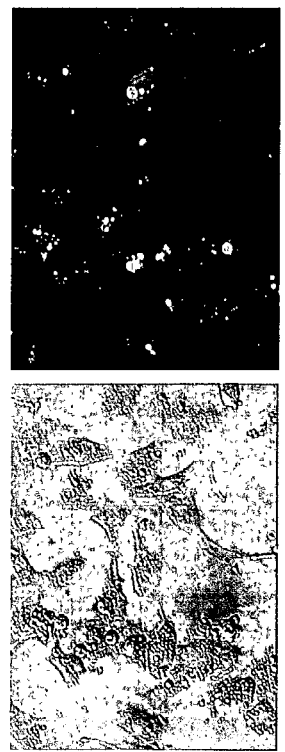
Fig. 4A  Anti-sense
Fig. 4C

Human ZEB cDNA

Genbank Accession Number: HSU19969

```
  1 ggaacagcag gcgagcagtg tgactggggc aggaaagaga agggagggag aggagggtgt
 61 agaaggggggt taggtcaggg aggtttgggg ctggatcagg tcgtcggtct tgcgggctgg
121 tgtaagcgca gaaagcaggc gaacccgcgg cgcaataacg ttacaaatta taatactgtg
181 gtagaaacaa attcagattc agatgatgaa gacaaactgc atattgtgga agaagaaagt
241 gttacagatg cagctgactg tgaaggtgta ccagaggatg acctgccaac agaccagaca
301 gtgttaccag ggaggagcag tgaaagagaa gggaatgcta agaactgctg ggaggatgac
361 agaaaggaag ggcaagaaat cctggggcct gaagctcagg cagatgaagc aggatgtaca
421 gtaaaagatg atgaatgcga gtcagatgca gaaaatgagc aaaaccatga tcctaatgtt
```

Fig. 9A

```
 481 gaagagtttc tacaacaaca agacactgct gtcattttc ctgaggcacc tgaagaggac
 541 cagaggcagg gcacaccaga agccagtggt catgatgaaa atggaacacc agatgcatt
 601 tcacaattac tcacctgtcc atattgtgat agaggctata aacgcttac ctctctgaaa
 661 gaacacatta aatatcgtca tgaaaagaat gaagataact ttagttgctc cctgtgcagt
 721 tacacctttg catacagaac ccaacttgaa cgtcacatga catcacataa atcaggaaga
 781 gatcaaagac atgtgacgca gtctgggtgt aatcgtaaat tcaaatgcac tgagtgtgga
 841 aaagctttca aatacaaaca tcacctaaaa gagcacttaa gaattcacag tggagagaag
 901 ccatatgaat gcccaaactg caagaaacgc tttcccatt ctggctccta tagctcacac
 961 ataagcagta agaaatgtat cagcttgata cctgtgaatg ggcgaccaag aacaggactc
1021 aagacatctc agtgttcttc accgtctctt tcagcatcac caggcagtcc cacacgacca
1081 cagatacggc aaaagataga gaataaaccc cttcaagaac aactttctgt taaccaaatt
1141 aaaactgaac ctgtggatta tgaattcaaa cccatagtgg ttgcttcagg aatcaactgt
1201 tcaaccctt tacaaaatgg ggttttcact ggtggtggcc cattacaggc aaccagttct
```

Fig. 9B

```
1261  cctcagggca  tggtgcaagc  tgttgttctg  ccaacagttg  gtttggtgtc  tcccataagt
1321  atcaatttaa  gtgatattca  gaatgtactt  aaagtggcgg  tagatggtaa  tgtaataagg
1381  caagtgttgg  agaataatca  agccaatctt  gcatccaaag  aacaagaaac  aatcaatgct
1441  tcacccatac  aacaaggtgg  ccattctgtt  atttcagcca  tcagtcttcc  tttggttgat
1501  caagatggaa  caaccaaaat  tatcatcaac  tacagtcttg  agcagcctag  ccaactttcaa
1561  gttgttcctc  aaaatttaaa  aaaagaaaat  ccagtcgcta  caaacagttg  taaaagtgaa
1621  aagttaccag  aagatcttac  tgttaagtct  gagaaggaca  aaagctttga  aggggggtg
1681  aatgatagca  cttgtcttct  gtgtgatgat  tgtccaggag  atattaatgc  acttccagaa
1741  ttaaagcact  atgacctaaa  gcagcctact  cagcctcctc  cactccctgc  agcagaagct
1801  gagaagcctg  agtcctctgt  ttcatcagct  actggagatg  gcaatttgtc  tcctagtcag
1861  ccacctttaa  agaacctctt  gtctctccta  aaagcatatt  atgctttgaa  tgcacaacca
1921  agtgcagaag  agctctcaaa  aattgctgat  tcagtaaacc  taccactgga  tgtagtaaaa
1981  aagtggtttg  aaaagatgca  agctggacag  atttcagtgc  agtcttctga  accatctct
```

Fig. 9C

```
2041  cctgaaccag gcaaagtaaa tatccctgcc aagaacaatg atcagcctca atctgcaaat
2101  gcaaatgaac cccaggacag cacagtaaat ctacaaagtc ctttgaagat gactaactcc
2161  cccgtttac cagtgggatc aaccaccaat ggttccagaa gtagtacacc atcccatca
2221  cctctaaacc tttcctcatc cagaaataca cagggttact tgtacacagc tgagggtgca
2281  caagaagagc cacaagtaga accctcttgat ctttcactac caaagcaaca gggagaatta
2341  ttagaaagaa ttcctttacc agaacagtgt ttattctgtc caggagaaac ccttgaactt
2401  gtcttggcaa aaaaggagcc acaaaaggac agttgtgtta cagactcaga accagttgta
2461  aatgtaatcc caccaagtgc caacccata tacctacagt tacctacagt cactgccag
2521  ttaccacaa tcgtggccat tgctgaccag aacagtgttc catgcttaag agcgctagct
2581  gccaataagc aaacgattct gattcccag cctactcaac tacggtcagc
2641  cctgcagtcc aagaaccacc cttgaaagtg atccagccaa atggaaatca ggatgaaaga
2701  caagatacta gctcagaagg agtatcaaat gtagaggatc agaatgactc tgattctaca
2761  ccgcccaaaa agaaaatgcg gaagacagaa aatggaaatgt atgcttgtga tttgtgtgac
```

Fig. 9D

```
2821  aagatattcc  aaaagagtag  ttcattattg  agacataaat  atgaacacac  aggtaaaaga
2881  cctcatgagt  gtggaatctg  taaaaaggca  tttaaacaca  aacatcattt  gattgaacac
2941  atgcgattac  attctggaga  aaagccctat  caatgtgaca  aatgtggaaa  gcgcttctca
3001  cactctgggt  ctagttctca  acacatgaat  catcgctact  ccatctgtaa  gagagaagcg
3061  gaagaacgtg  acagcacaga  gcaggaagag  gcagggcctg  aaatcctctc  gaatgagcac
3121  gtgggtgcca  gggcgtctcc  ctcacagggc  gactcggacg  agagagagag  tttgacaagg
3181  gaagaggatg  aagacagtga  aaaagaggaa  gaggaggagg  ataaagagat  ggaagaattg
3241  caggaagaaa  aagaatgtga  aaaaccacaa  ggggatgagg  aagaggagga  ggaggaggaa
3301  gaagtggaag  aggatgacag  agagagaggt  agaatgagg   gagaagaagc  aaaaactgaa
3361  ggtctgatga  agcaagtgtc  ggctgaaagt  caagcaagca  gcttaggaca  aaaagtaggc
3421  gagagtagtg  agcaagtgtc  tgaagaaaag  acaaatgaag  cctaatcgtt  tttctagaag
3481  gaaaataaat  tctaattgat  aatgaatttc  gttcaatatt  atccttcttt  tcatggaaac
3541  acagtaacct  gtatgctgtg  attcctgtta  cactactgtg  taaagtaaaa  actaaaaaaa
```

Fig. 9E

```
3601 tacaaaatac aaaacacaca cacacacaca cacacacaca caaaataaat
3661 ccgggcccgt tccctgaacc tcagacctag taattttca tgcagttttc aagttagga
3721 acaagtttgt aacatgcagc agattagaaa accttaatga ctcagagagc aacaatacaa
3781 gaggttaaag gaagctgatt aattagatat gcatctggca ttgttttatc ttatcagtat
3841 tatcactctt acgttggttt attcttaagc tgtacaattg ggagaaattt tataatttt
3901 tattggtaaa catatgctaa atccgcttca gtattttatt atgtttttta aaatgtgaga
3961 acttctgcac tacaaaattc ccttcacaga gaagtataat gtagttccaa cccgtgctaa
4021 ctaccttta taaattcagt ctagaaggta gtaatttcta atattagat gtcttagtag
4081 agcgtattat catttaaagt gtattgttag ccttaagaaa gcagctgata gaagaactga
4141 agtttcttac tcacgtggtt taaaatggag ttcaaaagat tgccttgagt tctgattgca
4201 ggggactaac aatgttaatc tgataaggac agcaaaatca tcagaatcag tgtttgtgat
4261 tgtgtttgaa tatgtggtaa catatgaagg atatgacatg aagctttgta tctcctttgg
4321 ccttaagcaa gacctgtgtg ctgtaagtgc catttctcag tatttcaag gctctaaccc
```

Fig. 9F

```
4381 gccttcaatc caatgtgtgg cctacaataa ctagcatttg ttgatttgtc tctgtatca
4441 aaattcccaa ataaaactta aaaccactga ctctgtcaga gaaactgaaa cactgggaca
4501 tttcatcctt caattcctcg gtattgattt tatgttgatt gattttcaga atttctctac
4561 agaaacgaaa gggaaatttt ctaatctgct ttatcatgta cttgcatttc agacatggac
4621 atgctattgt tatttggctc ataactgttt cccaaatgtt agttattatg gacccaattt
4681 attaacaaca ttagctgatt tttacctatc agtattattt tatttatttt agtttataga
4741 tctgtgcaac attttgactg atgtcttcaa acctggccgt aggaataccc ttcttactga
4801 catatgtact tttagtttta gaaaactttt atatttatgt gtcttatttt tatatttctt
4861 tatttattac acagtgtagt gtataatact gtagtttgta ttaatacaat aatatatttt
4921 agtatgaaaa tttggaaagt tgataagatt taaagtagag atgcaattgg ttctcctgca
4981 ttgagatttg atttaacagt gttatgttaa catttatact tgccttggac tgtagaacag
5041 aacttaaatg ggaatgtatt agtttacaa ctacaatcaa gtcattttac cttaccag
5101 tttaatat aaaacttaag gaattc
```

Fig. 9G

Human ZEB Protein Sequence

Genbank Accession Number: HSU19969

GTAGEQCDWGRKEKGGRGGCRRGLGQGGLGLDQVVGLAGWCKRR

KQANPRRNNVTNYNTVVETNSDSDDEDKLHIVEEESVTDAADCEGVPEDDLPTDQTVL

PGRSSEREGNAKNCWEDDRKEGQEILGPEAQADEAGCTVKDDECESDAENEQNHDPNV

EEFLQQQDTAVIFPEAPEEDQRQGTPEASGHDENGTPDAFSQLLTCPYCDRGYKRFTS

LKEHIKYRHEKNEDNFSCSLCSYTFAYRTQLERHMTSHKSGRDQRHVTQSGCNRKFKC

TECGKAFKYKHHLKEHLRIHSGEKPYECPNCKKRFSHSGSYSSHISSKKCISLIPVNG

RPRTGLKTSQCSSPSLSASPGSPTRPQIRQKIENKPLQEQLSVNQIKTEPVDYEFKPI

VVASGINCSTPLQNGVFTGGGPLQATSSPQGMVQAVVLPTVGLVSPISINLSDIQNVL

KVAVDGNVIRQVLENNQANLASKEQETINASPIQQGGHSVISAISLPLVDQDGTTKII

INYSLEQPSQLQVVPQNLKKENPVATNSCKSEKLPEDLTVKSEKDKSFEGGVNDSTCL

LCDDCPGDINALPELKHYDLKQPTQPPPLPAAEAEKPESSVSSATGDGNLSPSQPPLK

NLLSLLKAYYALNAQPSAEELSKIADSVNLPLDVVKKWFEKMQAGQISVQSSEPSSPE

PGKVNIPAKNNDQPQSANANEPQDSTVNLQSPLKMTNSPVLPVGSTTNGSRSSTPSPS

PLNLSSSRNTQGYLYTAEGAQEEPQVEPLDLSLPKQQGELLERIPLPEQCLFCPGRTL

ELVLAKKEPQKDSCVTDSEPVVNVIPPSANPINIAIPTVTAQLPTIVAIADQNSVPCL

RALAANKQTILIPQVAYTYSTTVSPAVQEPPLKVIQPNGNQDERQDTSSEGVSNVEDQ

NDSDSTPPKKKMRKTENGMYACDLCDKIFQKSSSLLRHKYEHTGKRPHECGICKKAFK

HKHHLIEHMRLHSGEKPYQCDKCGKRFSHSGSSSQHMNHRYSICKREAEERDSTEQEE

AGPEILSNEHVGARASPSQGDSDERESLTREEDEDSEKEEEEEDKEMEELQEEKECEK

PQGDEEEEEEEEVEEEEVEEAENEGEEAKTEGLMKDDRAESQASSLGQKVGESSEQVSEEKTNEA

Fig. 10

Murine ZEB cDNA sequence

Accession Number: L48363

```
  1 tggggcacca caagtaggcg tgaggcgcaa caaatcgtca tggctgaggc aggaaagagt
 61 agggtgggag aggataaggc tgtagaaggt gactcgagca tttagacaca agcgagagga
121 tcatggcgga tggcccagg tgtaagcgca gaaagcaggc gaacccgcgg cgcaataacg
181 ttacaaatta taatactgtg gtagaggcaa attcagatgc cgatgatgaa gacaaactcc
241 atattgtgga agaagaaagt attacagatg cagccgactg tgaaggtggc aagccagatg
301 atgaactgcc agcagaccag acagtattac caggaggcag tgacagggg ggcggtgcca
361 agaactgctg gcaagacaac gtgaaagaca acgagtgtga ttcagatgca gaaaatgagc
421 aaaaccatga tccgaatgtg gaagaatttc tgcagcaaca agacaccgcc gtcatttatc
481 ctgaggcgcc cgaggaccag cggcagggca caccagaagc cagcagtcat gatgaaaacg
541 gaacaccaga tgcattatcc cagttgctca cctgcccgta ttgtgataga ggctacaagc
601 gctttacctc tttgaaagaa cacattaagt accgccatga gaagaacgag gacaacttca
661 gctgctccct gtgcagttac acctttgcat acagaaccca gcttgaacgt catatgacat
721 cacataagtc aggaagagag caaagacatg tgacacagtc tgggggaaac cgcaagttca
781 agtgcactga atgcgggaag gcgttcaagt acaaacacca cctgaaagag cacttacgga
```

Fig. 11A

```
 841 ttcacagtgg agagaagcca tacgaatgcc cgaactgcaa gaaacggttt tcccattctg
 901 gctcctatag ctcacatata agcagtaaga agtgtattag cttgatgcct gtgaatggca
 961 ggcctagatc gggactcaag acatctcagt gttcctcgcc atctctttcg acatcaccag
1021 gcagtcccac acgcccacag atacgacaga agatagaggt aaataaaccc cttcaagaac
1081 cgctttctgt aaaccaaatc aaaactgaac ctgtggatta tgagttcaaa cccatagtgg
1141 ttgcttcagg aatcaactgt tcaacccctt tacaaaatgc ggttttttagc agtggtggcc
1201 aattgcaggc aaccagttct cctcagggtg tggtgcaagc cgttgttctg ccaacagttg
1261 gtttggtatc tcccataagt atcaacttaa gtgacattca gaatgtactt aaagtggctc
1321 tagatggtaa cgtaatacga caagtcttgg agactaatca agccagtctt gcatccaaag
1381 agcaagaagc agtgagtgct tcgcccatcc agcagggtgg ccattctgtc atttctgcca
1441 tcagtcttcc tttagttgat caggatggaa caaccaaaat catcatcaac tacagtcttg
1501 aggagcccag tcaacttcag gttgttcccc agaatttaaa gaaagaaatc ccagcccta
1561 caaacagctg caaaagtgag aagttaccag aagaccttac tgtcaaatca gaaacggaca
1621 aaaagctttga gggggccagg gatgatagca cttgccttct gtgtgaggac tgcccagggg
1681 acctcaatgc acttccagaa ctaaaaaagc actatgaccc agagtgccct gctcagcctc
1741 cacccctgc cccagccacc gagaagccag agtcctctgc ttcatcagct ggaaacggag
```

Fig. 11B

```
1801 atttgtctcc cagtcagcca cctttaaaga accttctgtc actcttgaaa gcctactatg
1861 ctctgaacgc gcagccaagc acagaagagc tctcaaagat cgccgattct gtgaacctac
1921 cgctggatgg agttaaaaag tggtttgaaa agatgcaagc tggacagatt ccaggacagt
1981 ctcctgaccc ccctttctcct ggaaccgggt cagtaaacat acctacaaaa accgatgagc
2041 agcctcaacc tgcggatgga aatgagcccc aggaagacag cacacgcgga cagagtcctg
2101 tcaagataag gagcactccg gttttacctg tgggatcagc catgaacggt tccagaagct
2161 gcacatcatc cccatcccct ctaaaccttt gctcagccag gaacccgcag ggttactctt
2221 gtgtggcaga gggtgcccag gaggagcccc aagtagaacc tcttgatctc tcactaccaa
2281 agcaacaggg agagttactg gaaaggtcga cagtcagtag cgtttaccag aacagtgttt
2341 attctgtcca ggaactaccc ttgaacttgt cttgtgcaaa aaaggaacca caaaaggaca
2401 gctgtgttac agactcagaa ccagttgtaa atgtagtccc accaagtgcc aacccataa
2461 acattgctat tcctacagtc actgcccagt taccacacaat cgtggccatt gctgaccaga
2521 acagtgttcc atgtttaaga gcactggccg ccaacaagca gactattctg attccccaag
2581 tggcatatgc ttattcagct actgtgagcc ctgccgtgca ggagccgcca gtgaaggtga
2641 tccagccaaa cggaaaccag gatgaaagac aagacactag ctcagaagga gtctccactg
2701 tggaggacca gaatgactct gactccacgc cacccaaaaa gaaaactcgg aagacagaga Fig. 11C
```

```
2761  atggaatgta tgcatgtgac ctgtgtgaca agatatttca gaagagcagc tcactgttga
2821  gacacaaata tgagcacaca ggtaagaggc ctcacgagtg tggaatctgt agaaaggcat
2881  ttaaacacaa gcatcatttg attgagcaca tgcggctgca ctctggggaa aagccctatc
2941  aatgtgacaa gtgtgtggcaag cgcttctcac actccggctc ctactctcaa catatgaatc
3001  accgctactc ctactgcaag agaggagctg aagacagaga tgctatggag caggaagacg
3061  ctgggcccga agtcctgccg gaagtcctgg cgactgagca tgtgggtgcc cgggcgtctc
3121  cctcacaggc tgactcggac gagagagaaa gtctgacaag ggaagaagat gaagacagtg
3181  aaaaggagga ggaggaggag gataaagaga tggaagaatt acaggaagga aaggaatgtg
3241  agaacccaca gggggaggag gaggaggagg aggaggagga agaggaggaa gaagaggagg
3301  aagaggaagt ggaagcggat gaagccgagc atgaggcagc agccaagact gatggtacag
3361  tggaggttgg agctgcacag caggcaggca gcttagagca gaaggccagc gagagcgaga
3421  tggagagcga aagcgagagt gagcagctgt ctgaggagaa gacaaatgaa gcttaggagt
3481  tcttctaaaa ggaaattcta cttggtaatg aaatttgctc tatattaccc acgctttttca
3541  tggaaacatg gctccatggc tcctgtgcta tggttcctgc gtaatgtcag
3601  aactgaaaaa aaaaaaaaat tccgggtgtg cgtgaacctc aaacctagta atttttcatg
3661  cagttttcaa agttaggaac aaatttataa catgaagcag cttagaaaac attaatgact
```

Fig. 11D 3721 cagaaaacaa aggtttctca gcaggttaca ggaggctgga tgggcgtccg gcatggctag 3781 cagtattatc actcttacgt tggctcattc ttaagctcta cattgggaga aattttataa 3841 ttttttttatt ggtaaacata tgctaaatcc gcttcagtat tttattatgt tttttaaaat 3901 gtgagaactt ctgcactaca gaattccctt cacagagcag tagaaagcag ttc

Fig. 11E

Murine ZEB protein Sequence
Accession Number: L48363

MADGPRCKRRKQANPRRNNVTNYNTVVEANSDADDEDKLHIVEE

ESITDAADCEGGKPDDELPADQTVLPGGSDRGGGAKNCWQDNVKDNECDSDAENEQNH

DPNVEEFLQQDTAVIYPEAPEDQRQGTPEASSHDENGTPDALSQLLTCPYCDRGYKR

FTSLKEHIKYRHEKNEDNFSCSLCSYTFAYRTQLERHMTSHKSGREQRHVTQSGGNRK

FKCTECGKAFKYKHHLKEHLRIHSGEKPYECPNCKKRFSHSGSYSSHISSKKCISLMP

VNGRPRSGLKTSQCSSPSLSTSPGSPTRPQIRQKIEVNKPLQEPLSVNQIKTEPVDYE

FKPIVVASGINCSTPLQNAVFSSGGQLQATSSPQGVVQAVVLPTVGLVSPISINLSDI

QNVLKVALDGNVIRQVLETNQASLASKEQEAVSASPIQQGGHSVISAISLPLVDQDGT

TKIINYSLEEPSQLQVVPQNLKKEIPAPTNSCKSEKLPEDLTVKSETDKSFEGARDD

STCLLCEDCPGDLNALPELKKHYDPECPAQPPPPAPATEKPESSASSAGNGDLSPSQP

PLKNLLSLLKAYYALNAQPSTEELSKIADSVNLPLDGVKKWFEKMQAGQIPGQSPDPP

SPGTGSVNIPTKTDEQPQPADGNEPQEDSTRGQSPVKIRSTPVLPVGSAMNGSRSCTS

SPSPLNLCSARNPQGYSCVAEGAQEEPQVEPLDLSLPKQQGELLERSTVSSVYQNSVY

SVQELPLNLSCAKKEPQKDSCVTDSEPVVNVPPSANPINIAIPTVTAQLPTIVAIAD

Fig. 12A

Immunostaining Melanoma Cell Lines

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
caagtgccaa ccccataaat                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tttttgggcg gtgtagaatc                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
catcaagaag gtggtgaagc                                                    20

<210> SEQ ID NO 4
<211> LENGTH: 20
<212> TYPE: DNA
<213> ORGANISM: Artificial Sequence
```

```
<220> FEATURE:
<223> OTHER INFORMATION: Primer

<400> SEQUENCE: 4
gagcttgaca aagtggtcgt                                                      20

<210> SEQ ID NO 5
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 5
gggccatccg ccatgatcct ctcgc                                                25

<210> SEQ ID NO 6
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 6
ggggcatgcg ccatgatcgt ctggc                                                25

<210> SEQ ID NO 7
<211> LENGTH: 42
<212> TYPE: DNA
<213> ORGANISM: Artificial Sequence
<220> FEATURE:
<223> OTHER INFORMATION: Primer

<400> SEQUENCE: 7
ataagcagta agaaatgtat cagcttgata cctgtgaatg gg                             42

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
attttgtaaa ggggttgaac agttgattcc tgaagcaacc ac                             42

<210> SEQ ID NO 9
<211> LENGTH: 5126
<212> TYPE: DNA
<213> ORGANISM: Human

<400> SEQUENCE: 9
ggaacagcag gcgagcagtg tgactggggc aggaaagaga agggagggag aggagggtgt          60 agaaggggt taggtcaggg aggtttgggg ctggatcagg tcgtcggtct tgcgggctgg          120
tgtaagcgca gaaagcaggc gaacccgcgg cgcaataacg ttacaaatta taatactgtg         180
gtagaaacaa attcagattc agatgatgaa gacaaactgc atattgtgga agaagaaagt         240
gttacagatg cagctgactg tgaaggtgta ccagaggatg acctgccaac agaccagaca         300
gtgttaccag ggaggagcag tgaaagagaa gggaatgcta agaactgctg ggaggatgac         360
agaaaggaag ggcaagaaat cctgggggcct gaagctcagg cagatgaagc aggatgtaca         420
gtaaaagatg atgaatgcga gtcagatgca gaaaatgagc aaaaccatga tcctaatgtt         480
```

-continued

```
gaagagtttc tacaacaaca agacactgct gtcattttc ctgaggcacc tgaagaggac      540
cagaggcagg gcacaccaga agccagtggt catgatgaaa atggaacacc agatgcattt      600
tcacaattac tcacctgtcc atattgtgat agaggctata aacgctttac ctctctgaaa      660
gaacacatta aatatcgtca tgaaaagaat gaagataact ttagttgctc cctgtgcagt      720
tacacctttg catacagaac ccaacttgaa cgtcacatga catcacataa atcaggaaga      780
gatcaaagac atgtgacgca gtctgggtgt aatcgtaaat tcaaatgcac tgagtgtgga      840
aaagctttca aatacaaaca tcacctaaaa gagcacttaa gaattcacag tggagagaag      900
ccatatgaat gcccaaactg caagaaacgc ttttcccatt ctggctccta tagctcacac      960
ataagcagta agaaatgtat cagcttgata cctgtgaatg ggcgaccaag aacaggactc     1020
aagacatctc agtgttcttc accgtctctt tcagcatcac caggcagtcc cacacgacca     1080
cagatacggc aaaagataga gaataaaccc cttcaagaac aactttctgt taaccaaatt     1140
aaaactgaac ctgtggatta tgaattcaaa cccatagtgg ttgcttcagg aatcaactgt     1200 tcaaccctt tacaaaatgg ggttttcact ggtggtggcc cattacaggc aaccagttct     1260
cctcagggca tggtgcaagc tgttgttctg ccaacagttg gtttggtgtc tcccataagt     1320
atcaatttaa gtgatattca gaatgtactt aaagtggcgg tagatggtaa tgtaataagg     1380
caagtgttgg agaataatca agccaatctt gcatccaaag aacaagaaac aatcaatgct     1440
tcacccatac aacaaggtgg ccattctgtt atttcagcca tcagtcttcc tttggttgat     1500
caagatggaa caaccaaaat tatcatcaac tacagtcttg agcagcctag ccaacttcaa     1560
gttgttcctc aaaatttaaa aaaagaaaat ccagtcgcta caaacagttg taaaagtgaa     1620
aagttaccag aagatcttac tgttaagtct gagaaggaca aaagctttga aggggggtg      1680 aatgatagca cttgtcttct gtgtgatgat tgtccaggag atattaatgc acttccagaa     1740
ttaaagcact atgacctaaa gcagcctact cagcctcctc cactccctgc agcagaagct     1800
gagaagcctg agtcctctgt ttcatcagct actggagatg gcaatttgtc tcctagtcag     1860
ccacctttaa agaaccttctt gtctctcta aaagcatatt atgctttgaa tgcacaacca     1920
agtgcagaag agctctcaaa aattgctgat tcagtaaacc taccactgga tgtagtaaaa     1980
aagtggtttg aaaagatgca agctggacag atttcagtgc agtcttctga accatcttct     2040
cctgaaccag gcaaagtaaa tatccctgcc aagaacaatg atcagcctca atctgcaaat     2100
gcaaatgaac cccaggacag cacagtaaat ctacaaagtc ctttgaagat gactaactcc     2160 cccgtttttac cagtgggatc aaccaccaat ggttccagaa gtagtacacc atccccatca     2220
cctctaaacc tttcctcatc cagaaataca cagggttact tgtacacagc tgagggtgca     2280
caagaagagc cacaagtaga aacctcttgat ctttcactac caaagcaaca gggagaatta     2340
ttagaaagaa ttcctttacc agaacagtgt ttattctgtc caggaagaac ccttgaactt     2400
gtcttggcaa aaaaggagcc acaaaaggac agttgtgtta cagactcaga accagttgta     2460
aatgtaatcc caccaagtgc caaccccata aatatcgcta tacctacagt cactgcccag     2520
ttacccacaa tcgtggccat tgctgaccag aacagtgttc catgcttaag agcgctagct     2580
gccaataagc aaacgattct gattccccag gtggcataca cctactcaac tacggtcagc     2640
cctgcagtcc aagaaccacc cttgaaagtg atccagccaa atggaaatca ggatgaaaga     2700
caagatacta gctcagaagg agtatcaaat gtagaggatc agaatgactc tgattctaca     2760
ccgcccaaaa agaaaatgcg gaagacagaa aatggaatgt atgcttgtga tttgtgtgac     2820
aagatattcc aaaagagtag ttcattattg agacataaat atgaacacac aggtaaaaga     2880
```

```
cctcatgagt gtggaatctg taaaaaggca tttaaacaca acatcatttt gattgaacac    2940
atgcgattac attctggaga aaagccctat caatgtgaca aatgtggaaa gcgcttctca    3000
cactctgggt ctagttctca acacatgaat catcgctact ccatctgtaa gagagaagcg    3060
gaagaacgtg acagcacaga gcaggaagag gcagggcctg aaatcctctc gaatgagcac    3120
gtgggtgcca gggcgtctcc ctcacagggc gactcggacg agagagagag tttgacaagg    3180
gaagaggatg aagacagtga aaaagaggaa gaggaggagg ataaagagat ggaagaattg    3240
caggaagaaa aagaatgtga aaaaccacaa ggggatgagg aagaggagga ggaggaggaa    3300
gaagtggaag aagaagaggt agaagaggca gagaatgagg gagaagaagc aaaaactgaa    3360
ggtctgatga aggatgacag ggctgaaagt caagcaagca gcttaggaca aaaagtaggc    3420
gagagtagtg agcaagtgtc tgaagaaaag acaaatgaag cctaatcgtt tttctagaag    3480
gaaaataaat tctaattgat aatgaatttc gttcaatatt atccttcttt tcatggaaac    3540
acagtaacct gtatgctgtg attcctgtta cactactgtg taaagtaaaa actaaaaaaa    3600
tacaaaatac aaaacacaca cacacacaca cacacacaca cacacacaca caaaataaat    3660
ccgggcccgt tccctgaacc tcagacctag taattttttca tgcagttttc aaagttagga    3720
acaagtttgt aacatgcagc agattagaaa accttaatga ctcagagagc aacaatacaa    3780
gaggttaaag gaagctgatt aattagatat gcatctggca ttgttttatc ttatcagtat    3840
tatcactctt acgttggttt attcttaagc tgtacaattg ggagaaattt tataatttt    3900 tattggtaaa catatgctaa atccgcttca gtatttttatt atgtttttta aaatgtgaga    3960
acttctgcac tacaaaattc ccttcacaga gaagtataat gtagttccaa cccgtgctaa    4020 ctaccttta taaattcagt ctagaaggta gtaatttcta atatttagat gtcttagtag    4080
agcgtattat catttaaagt gtattgttag ccttaagaaa gcagctgata aagaactga    4140 agtttcttac tcacgtggtt taaaatggag ttcaaaagat tgccttgagt tctgattgca    4200
ggggactaac aatgttaatc tgataaggac agcaaaatca tcagaatcag tgtttgtgat    4260
tgtgtttgaa tatgtggtaa catatgaagg atatgacatg aagctttgta tctcctttgg    4320
ccttaagcaa gacctgtgtg ctgtaagtgc catttctcag tatttttcaag gctctaaccc    4380 gccttcaatc caatgtgtgg cctacaataa ctagcatttg ttgatttgtc tcttgtatca    4440
aaattcccaa ataaaactta aaaccactga ctctgtcaga gaaactgaaa cactgggaca    4500
tttcatcctt caattcctcg gtattgattt tatgttgatt gattttcaga atttctctac    4560
agaaacgaaa gggaaatttt ctaatctgct ttatcatgta cttgcatttc agacatggac    4620
atgctattgt tatttggctc ataactgttt cccaaatgtt agttattatg gacccaattt    4680
attaacaaca ttagctgatt tttacctatc agtattattt tatttatttt agtttataga    4740
tctgtgcaac attttgactg atgtcttcaa acctggccgt aggaataccc ttcttactga    4800
catatgtact tttagttttta gaaaacttttt atatttatgt gtcttatttt tatatttctt    4860
tatttattac acagtgtagt gtataatact gtagtttgta ttaatacaat aatatatttt    4920
agtatgaaaa tttggaaagt tgataagatt taaagtagag atgcaattgg ttctcctgca    4980
ttgagatttg atttaacagt gttatgttaa catttatact tgccttggac tgtagaacag    5040
aacttaaatg ggaatgtatt agtttttacaa ctacaatcaa gtcatttttac ctttacccag    5100 tttttaatat aaaacttaag gaattc                                          5126
```

<210> SEQ ID NO 10

<211> LENGTH: 1154
<212> TYPE: PRT
<213> ORGANISM: Human

<400> SEQUENCE: 10

```
Gly Thr Ala Gly Glu Gln Cys Asp Trp Gly Arg Lys Glu Lys Gly Gly
  1               5                  10                  15
Arg Gly Gly Cys Arg Arg Gly Leu Gly Gln Gly Gly Leu Gly Leu Asp
             20                  25                  30
Gln Val Val Gly Leu Ala Gly Trp Cys Lys Arg Lys Gln Ala Asn
         35                  40                  45
Pro Arg Arg Asn Asn Val Thr Asn Tyr Asn Thr Val Glu Thr Asn
 50                  55                  60
Ser Asp Ser Asp Asp Glu Asp Lys Leu His Ile Val Glu Glu Ser
 65                  70                  75                  80
Val Thr Asp Ala Ala Asp Cys Glu Gly Val Pro Glu Asp Leu Pro
                 85                  90                  95
Thr Asp Gln Thr Val Leu Pro Gly Arg Ser Glu Arg Glu Gly Asn
                100                 105                 110
Ala Lys Asn Cys Trp Glu Asp Arg Lys Glu Gly Gln Glu Ile Leu
            115                 120                 125
Gly Pro Glu Ala Gln Ala Asp Glu Ala Gly Cys Thr Val Lys Asp Asp
130                 135                 140
Glu Cys Glu Ser Asp Ala Glu Asn Glu Gln Asn His Asp Pro Asn Val
145                 150                 155                 160
Glu Glu Phe Leu Gln Gln Asp Thr Ala Val Ile Phe Pro Glu Ala
                165                 170                 175
Pro Glu Glu Asp Gln Arg Gln Gly Thr Pro Glu Ala Ser Gly His Asp
                180                 185                 190
Glu Asn Gly Thr Pro Asp Ala Phe Ser Gln Leu Leu Thr Cys Pro Tyr
            195                 200                 205
Cys Asp Arg Gly Tyr Lys Arg Phe Thr Ser Leu Lys Glu His Ile Lys
210                 215                 220
Tyr Arg His Glu Lys Asn Glu Asp Asn Phe Ser Cys Ser Leu Cys Ser
225                 230                 235                 240
Tyr Thr Phe Ala Tyr Arg Thr Gln Leu Glu Arg His Met Thr Ser His
                245                 250                 255
Lys Ser Gly Arg Asp Gln Arg His Val Thr Gln Ser Gly Cys Asn Arg
            260                 265                 270
Lys Phe Lys Cys Thr Glu Cys Gly Lys Ala Phe Lys Tyr Lys His His
        275                 280                 285
Leu Lys Glu His Leu Arg Ile His Ser Gly Glu Lys Pro Tyr Glu Cys
    290                 295                 300
Pro Asn Cys Lys Lys Arg Phe Ser His Ser Gly Ser Tyr Ser Ser His
305                 310                 315                 320
Ile Ser Ser Lys Lys Cys Ile Ser Leu Ile Pro Val Asn Gly Arg Pro
                325                 330                 335
Arg Thr Gly Leu Lys Thr Ser Gln Cys Ser Ser Pro Ser Leu Ser Ala
            340                 345                 350
Ser Pro Gly Ser Pro Thr Arg Pro Gln Ile Arg Gln Lys Ile Glu Asn
        355                 360                 365
Lys Pro Leu Gln Glu Gln Leu Ser Val Asn Gln Ile Lys Thr Glu Pro
    370                 375                 380
Val Asp Tyr Glu Phe Lys Pro Ile Val Val Ala Ser Gly Ile Asn Cys
```

-continued

```
            385                 390                 395                 400
        Ser Thr Pro Leu Gln Asn Gly Val Phe Thr Gly Gly Pro Leu Gln
                        405                 410                 415
        Ala Thr Ser Ser Pro Gln Gly Met Val Gln Ala Val Leu Pro Thr
                        420                 425                 430
        Val Gly Leu Val Ser Pro Ile Ser Ile Asn Leu Ser Asp Ile Gln Asn
                        435                 440                 445
        Val Leu Lys Val Ala Val Asp Gly Asn Val Ile Arg Gln Val Leu Glu
                    450                 455                 460
        Asn Asn Gln Ala Asn Leu Ala Ser Lys Glu Gln Glu Thr Ile Asn Ala
        465                 470                 475                 480
        Ser Pro Ile Gln Gln Gly Gly His Ser Val Ile Ser Ala Ile Ser Leu
                            485                 490                 495
        Pro Leu Val Asp Gln Asp Gly Thr Thr Lys Ile Ile Ile Asn Tyr Ser
                            500                 505                 510
        Leu Glu Gln Pro Ser Gln Leu Gln Val Val Pro Gln Asn Leu Lys Lys
                        515                 520                 525
        Glu Asn Pro Val Ala Thr Asn Ser Cys Lys Ser Glu Lys Leu Pro Glu
        530                 535                 540
        Asp Leu Thr Val Lys Ser Glu Lys Asp Lys Ser Phe Glu Gly Gly Val
        545                 550                 555                 560
        Asn Asp Ser Thr Cys Leu Leu Cys Asp Asp Cys Pro Gly Asp Ile Asn
                            565                 570                 575
        Ala Leu Pro Glu Leu Lys His Tyr Asp Leu Lys Gln Pro Thr Gln Pro
                        580                 585                 590
        Pro Pro Leu Pro Ala Ala Glu Ala Lys Pro Glu Ser Ser Val Ser
                        595                 600                 605
        Ser Ala Thr Gly Asp Gly Asn Leu Ser Pro Ser Gln Pro Pro Leu Lys
                        610                 615                 620
        Asn Leu Leu Ser Leu Leu Lys Ala Tyr Tyr Ala Leu Asn Ala Gln Pro
        625                 630                 635                 640
        Ser Ala Glu Glu Leu Ser Lys Ile Ala Asp Ser Val Asn Leu Pro Leu
                        645                 650                 655
        Asp Val Val Lys Lys Trp Phe Glu Lys Met Gln Ala Gly Gln Ile Ser
                            660                 665                 670
        Val Gln Ser Ser Glu Pro Ser Pro Glu Pro Gly Lys Val Asn Ile
                        675                 680                 685
        Pro Ala Lys Asn Asn Asp Gln Pro Gln Ser Ala Asn Ala Asn Glu Pro
                        690                 695                 700
        Gln Asp Ser Thr Val Asn Leu Gln Ser Pro Leu Lys Met Thr Asn Ser
        705                 710                 715                 720
        Pro Val Leu Pro Val Gly Ser Thr Thr Asn Gly Ser Arg Ser Ser Thr
                            725                 730                 735
        Pro Ser Pro Ser Pro Leu Asn Leu Ser Ser Arg Asn Thr Gln Gly
                        740                 745                 750
        Tyr Leu Tyr Thr Ala Glu Gly Ala Gln Glu Pro Gln Val Glu Pro
                        755                 760                 765
        Leu Asp Leu Ser Leu Pro Lys Gln Gln Gly Glu Leu Leu Glu Arg Ile
                770                 775                 780
        Pro Leu Pro Glu Gln Cys Leu Phe Cys Pro Gly Arg Thr Leu Glu Leu
        785                 790                 795                 800
        Val Leu Ala Lys Lys Glu Pro Gln Lys Asp Ser Cys Val Thr Asp Ser
                        805                 810                 815
```

Glu Pro Val Val Asn Val Ile Pro Pro Ser Ala Asn Pro Ile Asn Ile
            820                 825                 830

Ala Ile Pro Thr Val Thr Ala Gln Leu Pro Thr Ile Val Ala Ile Ala
        835                 840                 845

Asp Gln Asn Ser Val Pro Cys Leu Arg Ala Leu Ala Ala Asn Lys Gln
    850                 855                 860

Thr Ile Leu Ile Pro Gln Val Ala Tyr Thr Tyr Ser Thr Thr Val Ser
865                 870                 875                 880

Pro Ala Val Gln Glu Pro Pro Leu Lys Val Ile Gln Pro Asn Gly Asn
                885                 890                 895

Gln Asp Glu Arg Gln Asp Thr Ser Ser Glu Gly Val Ser Asn Val Glu
            900                 905                 910

Asp Gln Asn Asp Ser Asp Ser Thr Pro Lys Lys Met Arg Lys
        915                 920                 925

Thr Glu Asn Gly Met Tyr Ala Cys Asp Leu Cys Asp Lys Ile Phe Gln
    930                 935                 940

Lys Ser Ser Ser Leu Leu Arg His Lys Tyr Glu His Thr Gly Lys Arg
945                 950                 955                 960

Pro His Glu Cys Gly Ile Cys Lys Lys Ala Phe Lys His Lys His His
                965                 970                 975

Leu Ile Glu His Met Arg Leu His Ser Gly Glu Lys Pro Tyr Gln Cys
            980                 985                 990

Asp Lys Cys Gly Lys Arg Phe Ser His Ser Gly Ser Ser Gln His
        995                 1000                1005

Met Asn His Arg Tyr Ser Ile Cys Lys Arg Glu Ala Glu Arg Asp
    1010                1015                1020

Ser Thr Glu Gln Glu Glu Ala Gly Pro Glu Ile Leu Ser Asn Glu His
1025                1030                1035                1040

Val Gly Ala Arg Ala Ser Pro Ser Gln Gly Asp Ser Asp Glu Arg Glu
                1045                1050                1055

Ser Leu Thr Arg Glu Glu Asp Glu Asp Ser Glu Lys Glu Glu Glu Glu
            1060                1065                1070

Glu Asp Lys Glu Met Glu Glu Leu Gln Glu Lys Glu Cys Glu Lys
        1075                1080                1085

Pro Gln Gly Asp Glu Glu Glu Glu Glu Glu Glu Val Glu Glu
    1090                1095                1100

Glu Glu Val Glu Glu Ala Glu Asn Glu Gly Glu Glu Ala Lys Thr Glu
1105                1110                1115                1120

Gly Leu Met Lys Asp Asp Arg Ala Glu Ser Gln Ala Ser Ser Leu Gly
                1125                1130                1135

Gln Lys Val Gly Glu Ser Ser Glu Gln Val Ser Glu Glu Lys Thr Asn
            1140                1145                1150

Glu Ala

<210> SEQ ID NO 11
<211> LENGTH: 3953
<212> TYPE: DNA
<213> ORGANISM: Mouse

<400> SEQUENCE: 11
tggggcacca caagtaggcg tgaggcgcaa caaatcgtca tggctgaggc aggaaagagt        60
agggtgggag aggataaggc tgtagaaggt gactcgagca tttagacaca agcgagagga       120
tcatggcgga tggccccagg tgtaagcgca gaaagcaggc gaacccgcgg cgcaataacg       180

-continued

```
ttacaaatta taatactgtg gtagaggcaa attcagatgc cgatgatgaa gacaaactcc    240
atattgtgga agaagaaagt attacagatg cagccgactg tgaaggtggc aagccagatg    300
atgaactgcc agcagaccag acagtattac caggaggcag tgacagggg ggcggtgcca     360
agaactgctg gcaagacaac gtgaaagaca acgagtgtga ttcagatgca gaaaatgagc    420
aaaaccatga tccgaatgtg gaagaatttc tgcagcaaca agacaccgcc gtcatttatc    480
ctgaggcgcc cgaggaccag cggcagggca caccagaagc cagcagtcat gatgaaaacg    540
gaacaccaga tgcattatcc cagttgctca cctgcccgta ttgtgataga ggctacaagc    600
gctttacctc tttgaaagaa cacattaagt accgccatga agaacgag acaacttca       660
gctgctccct gtgcagttac acctttgcat acagaaccca gcttgaacgt catatgacat    720
cacataagtc aggaagagag caaagacatg tgacacagtc tggggaaac cgcaagttca     780
agtgcactga atgcgggaag gccttcaagt acaaacacca cctgaaagag cacttacgga    840
ttcacagtgg agagaagcca tacgaatgcc cgaactgcaa gaaacggttt tcccattctg    900
gctcctatag ctcacatata agcagtaaga agtgtattag cttgatgcct gtgaatggca    960
ggcctagatc gggactcaag acatctcagt gttcctcgcc atctctttcg acatcaccag   1020
gcagtcccac acgccacag atacgacaga agatagaggt aaataaaccc cttcaagaac    1080
cgctttctgt aaaccaaatc aaaactgaac ctgtggatta tgagttcaaa cccatagtgg   1140
ttgcttcagg aatcaactgt tcaacccctt tacaaaatgc ggttttttagc agtggtggcc   1200
aattgcaggc aaccagttct cctcagggtg tggtgcaagc cgttgttctg ccaacagttg   1260
gtttggtatc tcccataagt atcaacttaa gtgacattca gaatgtactt aaagtggctc   1320
tagatggtaa cgtaatacga caagtcttgg agactaatca agccagtctt gcatccaaag   1380
agcaagaagc agtgagtgct tcgcccatcc agcagggtgg ccattctgtc atttctgcca   1440
tcagtctttc tttagttgat caggatggaa caaccaaaat catcatcaac tacagtcttg   1500
aggagcccag tcaacttcag gttgttcccc agaatttaaa gaaagaaatc ccagccccta   1560
caaacagctg caaaagtgag aagttaccag aagaccttac tgtcaaatca gaaacggaca   1620
aaagctttga gggggccagg gatgatagca cttgccttct gtgtgaggac tgcccagggg   1680
acctcaatgc acttccagaa ctaaaaaagc actatgaccc agagtgccct gctcagcctc   1740
cacccctgc cccagccacc gagaagccag agtcctctgc ttcatcagct ggaaacggag   1800
atttgtctcc cagtcagcca cctttaaaga accttctgtc actcttgaaa gcctactatg   1860
ctctgaacgc gcagccaagc acagaagagc tctcaaagat cgccgattct gtgaacctac   1920
cgctggatga agttaaaaag tggtttgaaa agatgcaagc tggacagatt ccaggacagt   1980
ctcctgaccc cccttctcct ggaaccgggt cagtaaacat acctacaaaa accgatgagc   2040
agcctcaacc tgcggatgga aatgagcccc aggaagacag cacacgcgga cagagtcctg   2100
tcaagataag gagcactccg gttttacctg tgggatcagc catgaacggt tccagaagct   2160
gcacatcatc cccatcccct ctaaacctttt gctcagccag gaaccgcag ggttactctt    2220
gtgtggcaga gggtgcccag gaggagcccc aagtagaacc tcttgatctc tcactaccaa   2280
agcaacaggg agagttactg gaaaggtcga cagtcagtag cgtttaccag aacagtgttt   2340
attctgtcca ggaactaccc ttgaacttgt cttgtgcaaa aaaggaacca caaaaggaca   2400
gctgtgttac agactcagaa ccagttgtaa atgtagtccc accaagtgcc aaccccataa   2460
acattgctat tcctacagtc actgcccagt tacccacaat cgtggccatt gctgaccaga   2520
```

-continued

```
acagtgttcc atgtttaaga gcactggccg ccaacaagca gactattctg attccccaag    2580
tggcatatgc ttattcagct actgtgagcc ctgccgtgca ggagccgcca gtgaaggtga    2640
tccagccaaa cggaaaccag gatgaaagac aagacactag ctcagaagga gtctccactg    2700
tggaggacca gaatgactct gactccacgc cacccaaaaa gaaaactcgg aagacagaga    2760
atggaatgta tgcatgtgac ctgtgtgaca agatatttca gaagagcagc tcactgttga    2820
gacacaaata tgagcacaca ggtaagaggc ctcacgagtg tggaatctgt agaaaggcat    2880
ttaaacacaa gcatcatttg attgagcaca tgcggctgca ctctggggaa aagccctatc    2940
aatgtgacaa gtgtggcaag cgcttctcac actccggctc ctactctcaa catatgaatc    3000
accgctactc ctactgcaag agaggagctg aagacagaga tgctatggag caggaagacg    3060
ctgggcccga agtcctgccg gaagtcctgg cgactgagca tgtgggtgcc cgggcgtctc    3120
cctcacaggc tgactcggac gagagagaaa gtctgacaag ggaagaagat gaagacagtg    3180
aaaaggagga ggaggaggaa gataaagaga tggaagaatt acaggaagga aaggaatgtg    3240
agaacccaca gggggaggag gaggaggagg aggaggagga gaggaggaa gaagaggagg    3300 aagaggaagt ggaagcggat gaagccgagc atgaggcagc agccaagact gatggtacag    3360
tggaggttgg agctgcacag caggcaggca gcttagagca gaaggccagc gagagcgaga    3420
tggagagcga aagcgagagt gagcagctgt ctgaggagaa gacaaatgaa gcttaggagt    3480
tcttctaaaa ggaaattcta cttggtaatg aaatttgctc tatattaccc acgcttttca    3540
tggaaacatg gctccatggc tcctgtgcta tggttcctgc tcactactgt gtaatgtcag    3600
aactgaaaaa aaaaaaaaat tccgggtgtg cgtgaacctc aaacctagta attttcatg    3660 cagttttcaa agttaggaac aaatttataa catgaagcag cttagaaaac attaatgact    3720
cagaaaacaa aggtttctca gcaggttaca ggaggctgga tgggcgtccg gcatggctag    3780
cagtattatc actcttacgt tggctcattc ttaagctcta cattgggaga aatttttataa    3840 tttttttatt ggtaaacata tgctaaatcc gcttcagtat tttattatgt tttttaaaat    3900
gtgagaactt ctgcactaca gaattcccctt cacagagcag tagaaaagcag ttc         3953
```

<210> SEQ ID NO 12
<211> LENGTH: 1117
<212> TYPE: PRT
<213> ORGANISM: Mouse

<400> SEQUENCE: 12

```
Met Ala Asp Gly Pro Arg Cys Lys Arg Arg Lys Gln Ala Asn Pro Arg
  1               5                  10                  15

Arg Asn Asn Val Thr Asn Tyr Asn Thr Val Val Glu Ala Asn Ser Asp
                 20                  25                  30

Ala Asp Asp Glu Asp Lys Leu His Ile Val Glu Glu Ser Ile Thr
             35                  40                  45

Asp Ala Ala Asp Cys Glu Gly Gly Lys Pro Asp Asp Glu Leu Pro Ala
         50                  55                  60

Asp Gln Thr Val Leu Pro Gly Gly Ser Asp Arg Gly Gly Gly Lys
 65                  70                  75                  80

Asn Cys Trp Gln Asp Asn Val Lys Asp Asn Glu Cys Asp Ser Asp Ala
                 85                  90                  95

Glu Asn Glu Gln Asn His Asp Pro Asn Val Glu Glu Phe Leu Gln Gln
                100                 105                 110

Gln Asp Thr Ala Val Ile Tyr Pro Glu Ala Pro Glu Asp Gln Arg Gln
            115                 120                 125
```

-continued

Gly Thr Pro Glu Ala Ser Ser His Asp Glu Asn Gly Thr Pro Asp Ala
130                     135                 140

Leu Ser Gln Leu Leu Thr Cys Pro Tyr Cys Asp Arg Gly Tyr Lys Arg
145                 150                 155                 160

Phe Thr Ser Leu Lys Glu His Ile Lys Tyr Arg His Glu Lys Asn Glu
                165                 170                 175

Asp Asn Phe Ser Cys Ser Leu Cys Ser Tyr Thr Phe Ala Tyr Arg Thr
            180                 185                 190

Gln Leu Glu Arg His Met Thr Ser His Lys Ser Gly Arg Glu Gln Arg
        195                 200                 205

His Val Thr Gln Ser Gly Gly Asn Arg Lys Phe Lys Cys Thr Glu Cys
    210                 215                 220

Gly Lys Ala Phe Lys Tyr Lys His His Leu Lys Glu His Leu Arg Ile
225                 230                 235                 240

His Ser Gly Glu Lys Pro Tyr Glu Cys Pro Asn Cys Lys Lys Arg Phe
                245                 250                 255

Ser His Ser Gly Ser Tyr Ser Ser His Ile Ser Ser Lys Lys Cys Ile
            260                 265                 270

Ser Leu Met Pro Val Asn Gly Arg Pro Arg Ser Gly Leu Lys Thr Ser
        275                 280                 285

Gln Cys Ser Ser Pro Ser Leu Ser Thr Ser Pro Gly Ser Pro Thr Arg
    290                 295                 300

Pro Gln Ile Arg Gln Lys Ile Glu Val Asn Lys Pro Leu Gln Glu Pro
305                 310                 315                 320

Leu Ser Val Asn Gln Ile Lys Thr Glu Pro Val Asp Tyr Glu Phe Lys
                325                 330                 335

Pro Ile Val Val Ala Ser Gly Ile Asn Cys Ser Thr Pro Leu Gln Asn
            340                 345                 350

Ala Val Phe Ser Ser Gly Gly Gln Leu Gln Ala Thr Ser Ser Pro Gln
        355                 360                 365

Gly Val Val Gln Ala Val Val Leu Pro Thr Val Gly Leu Val Ser Pro
    370                 375                 380

Ile Ser Ile Asn Leu Ser Asp Ile Gln Asn Val Leu Lys Val Ala Leu
385                 390                 395                 400

Asp Gly Asn Val Ile Arg Gln Val Leu Glu Thr Asn Gln Ala Ser Leu
                405                 410                 415

Ala Ser Lys Glu Gln Glu Ala Val Ser Ala Ser Pro Ile Gln Gln Gly
            420                 425                 430

Gly His Ser Val Ile Ser Ala Ile Ser Leu Pro Leu Val Asp Gln Asp
        435                 440                 445

Gly Thr Thr Lys Ile Ile Ile Asn Tyr Ser Leu Glu Glu Pro Ser Gln
    450                 455                 460

Leu Gln Val Val Pro Gln Asn Leu Lys Lys Glu Ile Pro Ala Pro Thr
465                 470                 475                 480

Asn Ser Cys Lys Ser Glu Lys Leu Pro Glu Asp Leu Thr Val Lys Ser
                485                 490                 495

Glu Thr Asp Lys Ser Phe Glu Gly Ala Arg Asp Asp Ser Thr Cys Leu
            500                 505                 510

Leu Cys Glu Asp Cys Pro Gly Asp Leu Asn Ala Leu Pro Glu Leu Lys
        515                 520                 525

Lys His Tyr Asp Pro Glu Cys Pro Ala Gln Pro Pro Pro Pro Ala Pro
530                 535                 540

-continued

| | | | | | | | | | | | | |
|---|---|---|---|---|---|---|---|---|---|---|---|---|
|Ala|Thr|Glu|Lys|Pro|Glu|Ser|Ser|Ala|Ser|Ser|Ala|Gly|Asn|Gly|Asp|
|545| | | | |550| | | | |555| | | | |560|

Leu Ser Pro Ser Gln Pro Pro Leu Lys Asn Leu Leu Ser Leu Leu Lys
565                     570                     575

Ala Tyr Tyr Ala Leu Asn Ala Gln Pro Ser Thr Glu Glu Leu Ser Lys
        580                     585                     590

Ile Ala Asp Ser Val Asn Leu Pro Leu Asp Gly Val Lys Lys Trp Phe
            595                     600                     605

Glu Lys Met Gln Ala Gly Gln Ile Pro Gly Gln Ser Pro Asp Pro Pro
    610                     615                     620

Ser Pro Gly Thr Gly Ser Val Asn Ile Pro Thr Lys Thr Asp Glu Gln
625                     630                     635                     640

Pro Gln Pro Ala Asp Gly Asn Glu Pro Gln Glu Asp Ser Thr Arg Gly
                645                     650                     655

Gln Ser Pro Val Lys Ile Arg Ser Thr Pro Val Leu Pro Val Gly Ser
                660                     665                     670

Ala Met Asn Gly Ser Arg Ser Cys Thr Ser Pro Ser Pro Leu Asn
            675                     680                     685

Leu Cys Ser Ala Arg Asn Pro Gln Gly Tyr Ser Cys Val Ala Glu Gly
    690                     695                     700

Ala Gln Glu Glu Pro Gln Val Glu Pro Leu Asp Leu Ser Leu Pro Lys
705                     710                     715                     720

Gln Gln Gly Glu Leu Leu Glu Arg Ser Thr Val Ser Ser Val Tyr Gln
                725                     730                     735

Asn Ser Val Tyr Ser Val Gln Glu Leu Pro Leu Asn Leu Ser Cys Ala
            740                     745                     750

Lys Lys Glu Pro Gln Lys Asp Ser Cys Val Thr Asp Ser Glu Pro Val
        755                     760                     765

Val Asn Val Val Pro Pro Ser Ala Asn Pro Ile Asn Ile Ala Ile Pro
770                     775                     780

Thr Val Thr Ala Gln Leu Pro Thr Ile Val Ala Ile Ala Asp Gln Asn
785                     790                     795                     800

Ser Val Pro Cys Leu Arg Ala Leu Ala Ala Asn Lys Gln Thr Ile Leu
                805                     810                     815

Ile Pro Gln Val Ala Tyr Ala Tyr Ser Ala Thr Val Ser Pro Ala Val
            820                     825                     830

Gln Glu Pro Pro Val Lys Val Ile Gln Pro Asn Gly Asn Gln Asp Glu
        835                     840                     845

Arg Gln Asp Thr Ser Ser Glu Gly Val Ser Thr Val Glu Asp Gln Asn
    850                     855                     860

Asp Ser Asp Ser Thr Pro Pro Lys Lys Thr Arg Lys Thr Glu Asn
865                     870                     875                     880

Gly Met Tyr Ala Cys Asp Leu Cys Asp Lys Ile Phe Gln Lys Ser Ser
                885                     890                     895

Ser Leu Leu Arg His Lys Tyr Glu His Thr Gly Lys Arg Pro His Glu
            900                     905                     910

Cys Gly Ile Cys Arg Lys Ala Phe Lys His Lys His His Leu Ile Glu
        915                     920                     925

His Met Arg Leu His Ser Gly Glu Lys Pro Tyr Gln Cys Asp Lys Cys
    930                     935                     940

Gly Lys Arg Phe Ser His Ser Gly Ser Tyr Ser Gln His Met Asn His
945                     950                     955                     960

Arg Tyr Ser Tyr Cys Lys Arg Gly Ala Glu Asp Arg Asp Ala Met Glu

```
                           965                 970                    975
Gln Glu Asp Ala Gly Pro Glu Val Leu Pro Glu Val Leu Ala Thr Glu
            980                 985                    990

His Val Gly Ala Arg Ala Ser Pro Ser Gln Ala Asp Ser Asp Glu Arg
            995                1000                   1005

Glu Ser Leu Thr Arg Glu Glu Asp Glu Asp Ser Glu Lys Glu Glu Glu
           1010                1015                   1020

Glu Glu Asp Lys Glu Met Glu Glu Leu Gln Glu Gly Lys Glu Cys Glu
1025                1030                    1035                1040

Asn Pro Gln Gly Glu Glu Glu Glu Glu Glu Glu Glu Glu Glu Glu Glu
                1045                1050                   1055

Glu Glu Glu Glu Glu Glu Val Glu Ala Asp Glu Ala Glu His Glu Ala
            1060                1065                   1070

Ala Ala Lys Thr Asp Gly Thr Val Glu Val Gly Ala Ala Gln Gln Ala
           1075                1080                   1085

Gly Ser Leu Glu Gln Lys Ala Ser Glu Ser Glu Met Glu Ser Glu Ser
           1090                1095                   1100

Glu Ser Glu Gln Leu Ser Glu Glu Lys Thr Asn Glu Ala
1105                1110                   1115
```

METHODS AND COMPOSITIONS USEFUL FOR DIAGNOSIS, STAGING, AND TREATMENT OF CANCERS AND TUMORS

This application claims priority to U.S. Provisional Application 60/317,300 filed Sep. 5, 2001, the entire disclosure of which is incorporated by reference herein.

Pursuant to 35 U.S.C. §202(c), it is hereby acknowledged that the U.S. Government has certain rights in the invention described herein, which was made in part with funds from the National Cancer Institute, Grant No. CA89194.

FIELD OF THE INVENTION

This invention relates to the fields of molecular biology and cancer detection. More specifically, novel compositions are provided which serve as prognostic indicators for staging neoplastic disease. Methods are also provided which facilitate the identification of those patients at risk for aggressive cancer progression. Methods are also provided which facilitate therapeutic treatment of a cancer in a mammal by modulating ZEB expression levels and activity.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

In the current state of the art in the diagnosis and treatment of cancers and tumors, it is of critical importance that a clinician or pathologist be able to stage cancer progression in a patient. The more accurately the clinician or pathologist can stage a tumor or a cancer, the greater the chances that an efficacious, minimally toxic treatment can be devised. At the present time, however, there are few reliable diagnostic markers in clinical use for the staging of various types of tumors or cancers, particularly those having a high degree of prevalence.

In addition to the direct examination of a biopsy sample, clinicians and pathologists presently rely heavily upon the presence or absence of a number of genetic or protein markers in a sample obtained from a patient in order to stage a tumor. Diagnostic or prognostic indicators such as oncogenes, growth factors, tumor suppressors, tumor-associated proteases, the loss of heterozygosity at particular alleles, chromosomal aberrations, and the like are examples of those indicators or markers currently in routine use.

An example of such a protein marker is the cell adhesion protein E-cadherin. The loss of this protein in a tumor cell or tissue is a hallmark of many later stage tumor types (Siitonnen et al., 1996, Am. J. Clin. Path., 105:394–401). Late stage tumors are generally primed biochemically, though not necessarily triggered, to metastasize (i.e., to migrate from their site of origin and to potentially invade and colonize a distant site). Immunostaining for the presence or loss of this critical marker is widely used as a standard indicator of the stage of progression of a tumor. In particular, this marker is routinely used for staging epithelial tumors, such as breast (Dahiya et al., 1998, Breast Cancer Res. & Treat., 52:185–200), colon, stomach, esophagus, bladder, and liver tumors, as well as for staging cancers such as prostate cancer, melanoma, and squamous cell carcinomas of the head and neck.

Several other markers specific for particular tumor or cancer types have been used with increasing frequency over the last five years. BRCA1 and BRCA2 in the context of breast and ovarian cancer are examples of such markers (Dahiya et al., 1998, Breast Cancer Res. & Treat., 52:185–200).

The regulation of programmed cell death and survival plays a critical role in development, homeostasis, and malignant cell transformation. In addition to carcinogenesis (59), cellular survival programs are particularly important for regulation of normal lymphopoiesis (5) and the development of the nervous system (49). A number of pathways and factors that promote survival or antagonize apoptosis have been characterized. It is now well established that disruption of the balance between the members of the Bcl-2 family which are either pro-(e.g. Bax, Bad, Bak) or anti- (e.g. Bcl-2, BCL-$X_L$, Bag) apoptotic, can ultimately affect the integrity of the mitochondrial membrane, resulting in the release of cytochrome C and activation of caspase enzymes, an ultimate and irreversible step in the apoptotic program (72). Members of the inhibitors of apoptosis protein (IAP) family of proteins suppress cell-death programs through their conserved baculoviral IAP repeats, by binding and inhibiting specific caspases (15). The pro-survival receptors of the TNFR family mediate their effects through the activation of MAPK/ERK cascades, resulting in the activation of the rel (NF-κB) and AP-1 transcription factor families which in turn transactivate genes of anti-apoptotic proteins, including IAPs (4, 16).

The transcriptional repressor ZEB (zfh-1/delta EF1) is a phylogenetically conserved DNA-binding protein containing eight kruppel-class zinc-finger domains as well as a homeodomain (21, 77, 74, 22, 24, 25). Identified based on its ability to bind E-box (CANNTG) motifs, ZEB has been implicated in the regulation of expression of a number of mammalian genes harboring such E-boxes. These include muscle-specific genes [the alpha-1 subunit of Na+, K+-ATPase (74), and muscle creatine kinase (63, 52)], genes specific for hematopoietic cells [interleukin 2 (77, 79), the immunoglobulin heavy chain (24), gata-3 (26), CD4 (9)], and other genes [delta-1 crystalline (22), alpha-4 integrin (31), ovalbumin (66), and E-cadherin (27)]. E-boxes, key regulatory elements in many promoters and enhancers, are known to bind the basic Helix-Loop-Helix (bHLH) class of trancriptional activators (41). Several bHLH transcriptional activators have been shown to trigger cell-type-specific differentiation programs (6, 41). The use of any of the above-identified molecules as markers for cancer progression has not yet been described.

BRIEF SUMMARY OF THE INVENTION

The present inventor has appreciated the need for molecular markers for cancer progression to identify patients who are at risk for aggressive disease and would benefit most from early intervention and treatment.

The present invention includes methods, compositions and kits which employ one or more detection reagents comprising an antibody which binds specifically with ZEB protein, a ZEB antisense oligonucleotide, and a ZEB-specific PCR primer for determining the stage of progression of a cancer or a tumor in a mammal. Preferably, the cancer or tumor is of epithelial origin. Additionally, the methods, compositions and kits of the invention are useful in the diagnosis and treatment of such cancers and tumors in a mammal.

The present invention is directed to methods for diagnosing and/or staging a tumor in a cell or biological sample. An exemplary method entails contacting a biological sample with a composition comprising at least one ZEB-specific detection reagent for a suitable time period and in an amount effective for detection of a ZEB-associated molecule in a sample; determining the amount and/or cellular localization of the ZEB-associated molecule, thereby diagnosing or staging the tumor present in a biological sample.

Exemplary ZEB-detection reagents include without limitation, oligonucleotides which hybridize with ZEB encoding nucleic acids, antibodies or fragments thereof with binding affinity for ZEB polypeptides or fragments thereof. Such antibody fragments include sFv, and Fab for example. Exemplary ZEB-associated molecules are genomic DNA, cDNA, or mRNA or oligonucleotides encoding ZEB protein or fragments or complementary strands thereof and ZEB polypeptides and fragments thereof.

The present invention also includes a method of treating a cancer in a mammal, the method comprising administering to a mammal a composition comprising a ZEB-associated molecule in an amount effective to de-repress an apoptotic pathway in cancer cells, thereby triggering programmed cell death in the cancer cells in said mammal. Cancers to be treated are preferably those of epithelial origin, including without limitation cancers of the skin, breast, prostate, colon, lung and ovaries.

In yet another embodiment of the present invention, a ZEB antisense oligonucleotide comprising nucleic acid sequences of SEQ ID NO: 5 and SEQ ID NO: 6 are provided. The present invention also comprises the use of a ZEB antisense oligonucleotide which shares at least about 80% homology with the nucleic acid sequences of SEQ ID NO: 5 and SEQ ID NO: 6.

In yet another embodiment of the present invention, primers suitable for amplifying ZEB encoding nucleic acids are provided. Exemplary ZEB-specific PCR primers include SEQ ID NO: 1 and SEQ ID NO: 2. The present invention also encompasses ZEB-specific PCR primers which share at least about 80% homology with nucleic acids of SEQ ID NO: 1 and SEQ ID NO: 2.

Pharmaceutical compositions suitable for administration to a patient comprising the above-mentioned ZEB-associated molecules are also within the scope of the present invention.

In yet another aspect, the present invention also provides kits for diagnosing and/or staging cancer in a mammal. An exemplary kit contains a container or a sample vial for storing a sample of a tissue or a body fluid; a composition comprising at least one ZEB-specific detection reagent in an amount effective to permit detection of a ZEB-associated molecule in a sample; and an instructional material which directs use of the composition for determining the amount and the sub-cellular location of a ZEB-associated molecule.

BRIEF DESCRIPTION OF THE DRAWINGS

The foregoing summary, as well as the following detailed description of preferred embodiments of the invention, will be better understood when read in conjunction with the appended drawings.

FIG. 4 demonstrates that ZEB-specific antisense morpholino oligomers cause fibroblasts to apoptose. (A) NIH 3T3 fibroblasts were transfected with 1.4 micromolar flourescein-labeled anti-sense morpholino oligos targeted to the ZEB initiation codon. The apoptotic morphology shown was apparent within 3–4 hours of administration. (B) Equivalent amounts of control mis-sense flourescein-labled oligos (see Materials and Methods for sequence) showed nearly normal morphology. (C&D) Western analysis of parallel transfections shows a significant reduction of ZEB protein with the anti-sense oligo, compared to endogenous levels of GAPDH.

FIG. 9A–G depicts nucleic acid sequences of human ZEB (SEQ ID NO: 9).

FIG. 10 depicts amino acid sequences of human ZEB protein (SEQ ID NO: 10)

FIG. 11A–E depicts nucleic acid sequences of murine ZEB (SEQ ID NO: 11).

FIG. 12A depicts amino acid sequences of murine ZEB protein (SEQ ID NO: 12).

DETAILED DESCRIPTION OF THE INVENTION

Figure 1B:
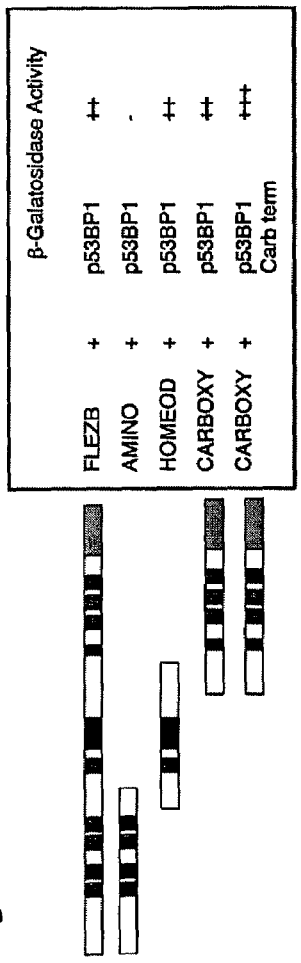
FIG. 1 shows interaction of ZEB with p53 binding protein 1 (53BP1). (A) Complementation of auxotrophy by true interacting peptides allows growth on selective media. Upper plate is -LEU/-TRP, and allows growth of all test transformations, denoted by the numbered combinations below. Bottom plate is -LEU/-TRP/-HIS, and only allows growth of the ZEB-53BP1 co-transformants, activating the HIS3 gene. (B) Sequences between the carboxyl zinc fingers and the homeobox of ZEB are responsible for the interaction with the carboxyl terminal region of 53BP1. Indicated fragments of ZEB, shown on the left were cloned into the yeast vector pAS2-1 and co-transformed with the indicated 53BP1 fragments (in the vector pGAD10) into the strain Y-190. Liquid cultures of the resulting transformants were tested for beta-galatosidase activity as described in Materials and Methods. (C) ZEB interacts with 53BP1 in vitro in GST pulldown experiments. Contents of each lane is as follows: M,$^{35}$S-labeled protein markers; 1, GST protein+carboxyl IVT p53BP1; 2, GST+fl IVTp53BP1; 3, GST-ZEB+IVT cocktail; 4, GST-ZEB+carboxyl p53BP1; 5, fl IVT p53BP1; 6, GST-ZEB+fl IVT p53BP1, same as 6, with 5 micrograms of purified unlabeled, bacterially-expressed, HA-carboxyl p53BP1 added during the initial binding reaction.

The present invention relates to methods and compositions which are useful for the diagnosis, staging, and treatment of a cancer or a tumor in a mammal. The methods and compositions of the invention employ detection of the zinc finger protein ZEB or ZEB-associated molecules as markers for assessing stages of cancer progression. The ZEB protein is recognized in the literature as ZEB, delta EF-1, or zfh-1, but for simplicity is referred to herein as ZEB protein. ZEB-associated molecules, including ZEB-encoding nucleic acids, ZEB protein or peptide fragments are detected in a sample obtained from a patient using one or more detection reagents. Such ZEB detection reagents an antibody capable of specifically binding with a ZEB protein, an antisense oligonucleotide capable of specifically binding to ZEB mRNA, and ZEB-specific PCR primers. The detection reagent used in the methods and compositions of the invention serves to provide information regarding the amount and/or the localization of ZEB protein within a cell or tissue of a mammal. Based upon the amount and/or localization of ZEB protein in a cell or tissue of a mammal, a diagnosis can be made with regard to the presence or absence of a particular tumor or cancer type, and the stage of a tumor can be determined.

In addition, the methods and compositions of the invention are useful for the treatment of cancer cells or tumors in a mammal, by employing a ZEB antisense oligonucleotide in an amount effective to de-repress an apoptotic pathway in a mammalian cancer cell or tumor, thereby activating apoptotic pathways that trigger programmed cell death. The initiation of programmed cell death or apoptosis in a cancer cell or cells of a tumor eliminates such cells and therefore provides an effective means for treating a cancer or tumor in the mammal. Kits for practicing the methods of the invention are also included. In all of the methods and compositions of the invention, the mammal can be any mammal, and is preferably a human.

Definitions

The articles "a" and "an" are used herein to refer to at least one (i.e., to at least one) of the grammatical object of the article. By way of example, "an element" means one element or more than one element.

As used herein, the term "binds specifically with" or "specific binding" in the context of an antibody means to bind substantially to a particular antigen (i.e. ZEB protein) without binding substantially to other molecules which are present with the antigen.

The term "specific binding pair" as used herein includes, without limitation, antigen-antibody, receptor-ligand, nucleic acid (RNA or DNA) hybridizing sequences, Fc receptor or mouse IgG-protein A, avidin-biotin, and streptavidin-biotin. Various other determinant-specific binding substance combinations are contemplated for use in practicing the methods of the invention, such as will be apparent to those skilled in the art. The antibodies in the compositions and methods of the present invention may exist in a variety of forms including, for example, polyclonal antibodies, monoclonal antibodies, Fv, Fab and F(ab)$_2$, as well as single chain antibodies and humanized antibodies (Harlow et al., 1988, Antibodies: A Laboratory Manual, Cold Spring Harbor, New York; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology. Such technology is well known in the art.

As used herein, the phrase "to treat a cancer or a tumor" or "treating a cancer or a tumor" in a mammal means one or more of alleviating a symptom of, correcting an underlying molecular or physiological disorder of, or reducing the frequency or severity of a pathological or deleterious physiological consequence of a cancer or a tumor in a mammal. By way of example, and not by limitation, the deleterious physiological consequences of a cancer or a tumor can include uncontrolled proliferation, metastasis and invasion of other tissues, and suppression of an immune response.

As used herein, to "stage a tumor" or to "determine the stage of progression of a tumor" means to ascertain the stage of progression of a tumor along the continuum from non-invasive to invasive, or from non-metastatic to metastatic. Typically tumors are staged from grades I–IV with IV being the most malignant or metastatic.

As used herein, a "dominant negative ZEB construct" refers to constructs encoding variants of ZEB or specific domains of ZEB which upon expression in a recombinant host cell either 1) inhibit the function(s) of endogenously expressed ZEB protein or 2) counteract the functional activity of endogenous ZEB by competitively binding to a ZEB binding site, thereby transactivating a gene regulated by the occupancy of the ZEB binding site.

As used herein, to "de-repress an apoptotic pathway" in a cell or tissue means to cause target genes which encode any or all of the protein effectors of an apoptotic pathway to be regulated from an "off" state to a "neutral" state through the biochemical interaction of ZEB or a ZEB variant (mutant or chimeric fusion protein) with the regulatory regions of those genes. Also, as used herein, to "upregulate an apoptotic pathway" in a cell or tissue means to cause target genes which encode any or all of the protein effectors of an apoptotic pathway to be regulated from a "neutral" to an "on" state through the biochemical interaction of ZEB or a ZEB variant (mutant or chimeric fusion protein) with the regulatory regions of those genes.

As used herein, the term "isolated polypeptide" refers to a polypeptide segment or fragment which has been separated from sequences which flank it in a naturally occurring state, e.g., a polypeptide fragment which has been removed from the sequences which are normally adjacent to the fragment, e.g., the sequences adjacent to the fragment in a protein in which it naturally occurs. The term also applies to a polypeptide which has been substantially purified from other components which naturally accompany the polypeptide, e.g., proteins, RNA or DNA which naturally accompany it in the cell. The term therefore includes, for example, a recombinant polypeptide which is encoded by a nucleic acid incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant polypeptide which is part of a hybrid polypeptide comprising additional amino acids.

As used herein, the term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well. A host cell that comprises a recombinant polynucleotide is referred to as a "recombinant host cell." A gene which is expressed in a recombinant host cell wherein the gene comprises a recombinant polynucleotide, expresses a "recombinant polypeptide."

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of at least a first and a second nucleic acid molecule wherein a hybrid nucleic acid molecule is generated.

As used herein, the term "recombinant polypeptide" means a polypeptide which is produced upon expression of a recombinant polynucleotide.

As used herein, an "isolated polypeptide" is one which is separated from components with which it naturally occurs.

As used herein, the term "polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

It will be appreciated that the peptides or polypeptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the peptide or polypeptide antibody or fragment thereof at its termini which is likely to affect the function of the peptide or polypeptide, i.e. sequential degradation of the peptide or polypeptide at a terminal end thereof.

Blocking groups include protecting groups conventionally used in the art of peptide chemistry which will not adversely affect the in vivo activity of the peptide or polypeptide antibody or fragment thereof. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the biological activity of the peptide or polypeptide antibody or fragment thereof. Such modifications include, but are not limited to, substitution of one or more of the amino acids in the natural L-isomeric form with amino acids in the D-isomeric form. Thus, the peptide may include one or more D-amino acid residues, or may comprise amino acids which are all in the D-form. Retro-inverso forms of peptides in accordance with the present invention are also contemplated, for example, inverted peptides in which all amino acids are substituted with D-amino acid forms.

Acid addition salts of the peptide or polypeptide antibody or fragment thereof are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicylic and the like, to provide a water soluble salt of the peptide.

The present invention also includes analogs of polypeptides or peptides of the invention. Analogs can differ from naturally occurring proteins or peptides by conservative amino acid sequence differences or by any of the modifications described herein or known in the art.

For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included in the invention are polypeptides which have been modified using standard molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In any of the compositions and methods of the invention described herein, one or more of a functional element, an analog, an epitope, and a chimeric peptide can be used in place of a polypeptide or peptide antibody or fragment thereof. This enables use of a smaller peptide in the inventive compositions having similar or greater activity than the corresponding larger peptide or polypeptide of the invention. By way of example and not by limitation, such functional elements, analogs, epitopes and chimeric peptides can be prepared using recombinant technology or they can be isolated from natural sources. Alternatively, they can be prepared synthetically by using any peptide synthesis method known in the art, such as a solid-phase peptide synthesis method.

The isolated polypeptide can be obtained by preparing and purifying a recombinant version of any of the polypeptides described herein. Molecular biology techniques for the preparation of recombinant polypeptides are well known in the art, and are described for example in Sambrook et al., 1989, *Molecular Cloning: A Laboratory Manual*, Cold Spring Harbor Laboratory, New York; Ausubel et al., 1994, *Current Protocols in Molecular Biology*, John Wiley & Sons, New York), and Gerhardt et al., eds., 1994, *Methods for General and Molecular Bacteriology*, American Society for Microbiology, Washington, D.C. Protein purification methods are also well known in the art, and are described, for example in Deutscher et al. (ed., 1990, *Guide to Protein Purification*, Harcourt Brace Jovanovich, San Diego).

As used herein, an "analog" of a peptide or polypeptide antibody or fragment thereof means a peptide or polypeptide which has been modified from the naturally occurring peptide or polypeptide by any of the modifications described herein or known to the skilled artisan, but which still exhibits activity similar to the naturally occurring peptide or polypeptide in binding specifically with ZEB protein.

As used herein, a "chimeric peptide" or "chimeric polypeptide" or "fusion protein" means a protein or polypeptide which comprises at least a portion of a first naturally occurring protein or polypeptide fused to least a portion of a second protein or polypeptide. For example, a ZEB chimeric protein may include a portion or all of a ZEB protein fused with another peptide or polypeptide such as a fusion partner, a protein tag or other chemical moiety, that may confer useful properties to ZEB, such as, for example, an epitope for an antibody, a polyhistidine sequence, a biotin moiety and the like. Such a ZEB fusion protein would retain some or all of ZEB activity. A fusion protein may also comprise portions derived from more than two naturally occurring proteins and/or polypeptides.

As used herein, a "functional element" of a protein or polypeptide fragment thereof means a portion of the protein or fragment thereof which retains some or all of the activity of the larger protein or polypeptide fragment. By way of example and not by limitation, the functional element can be a peptide, a peptide analog or an epitope of a polypeptide, a chimeric peptide thereof or an analog of a chimeric peptide thereof.

As used herein, an "epitope" of a peptide or a polypeptide means a portion of a peptide or polypeptide which is generally exposed at the surface of the peptide or polypeptide and for which one member of a specific binding pair has binding affinity.

With respect to antibodies of the invention, the term "immunologically specific" refers to antibodies that bind to one or more epitopes of a protein of interest (e.g., ZEB protein), but which do not substantially recognize and bind other molecules in a sample containing a mixed population of antigenic biological molecules.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "vector" refers to a small carrier DNA molecule into which a DNA sequence can be inserted for introduction into a host cell where it will be replicated. Thus, the term "vector" includes any replicating plasmid or a virus. The term also encompasses defective retroviral based vectors that require co-expression of a helper virus for expression. Examples of viral vectors include, but are not limited to, adenoviral vectors, adeno-associated viral vectors, retroviral vectors, and the like. An "expression vector" is a specialized vector that contains a gene with the necessary regulatory regions needed for expression in a host cell.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "promoter region" refers to the transcriptional regulatory regions of a gene, which may be found at the 5' or 3' side of the coding region, or within the coding region, or within introns.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

An "inducible" promoter is a nucleotide sequence which, when operably linked with a polynucleotide which encodes or specifies a gene product, causes the gene product to be produced in a living cell substantially only when an inducer which corresponds to the promoter is present in the cell. Living cells include, without limitation, prokaryotic cells, eukaryotic cells, including yeast cells and cells derived from an insect or a mammal.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The term "transformed" or "transformation" in the context of a cancer cell shall refer to the process by which a cell escapes normal cellular growth and regulatory controls.

As used herein, the term "antisense" in the context of an oligonucleotide refers particularly to the nucleic acid sequence of the non-coding strand of a double stranded DNA molecule encoding a protein, or to a sequence which is substantially homologous to the non-coding strand. As defined herein, an antisense oligonucleotide sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By "complementary to a portion or all of the nucleic acid encoding ZEB protein" is meant a sequence of nucleic acid which does not encode ZEB protein. Rather, the sequence which is being expressed in the cells is identical to the non-coding strand of the nucleic acid encoding ZEB protein and thus, does not encode ZEB protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules or a DNA/RNA hybrid. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Description

The invention includes a method of staging a cancer or a tumor in a mammal, preferably a human. Types of cancers that may be assessed using the methods of the invention include, without limitation, melanoma, gastric (stomach) cancer, breast cancer, colon cancer, prostate cancer, ovarian cancer, tumors of the gastrointestinal tract, epithelial cell-derived tumors, T- and B-cell leukemia, T- and B-cell lymphoma, tumors of the central nervous system, and tumors of the peripheral nervous system.

The method comprises obtaining a sample of a tissue or a body fluid from the mammal. Non-limiting examples of tissue or body fluids which can be used include blood, plasma, lymph, and tumor biopsies.

The sample of the tissue or body fluid from the mammal is contacted with a composition comprising one or more detection reagents comprising an antibody which binds specifically with ZEB protein, an antisense oligonucleotide which binds specifically with ZEB mRNA, and a ZEB-specific PCR primer pair.

The nucleotide sequence of full length human ZEB cDNA (SEQ ID NO: 9) is provided in FIG. 9.

The amino acid sequence of human ZEB protein (SEQ ID NO: 10), which is encoded by SEQ ID NO: 9 is provided in FIG. 10.

The sample can be contacted with the composition comprising one or more detection reagents by any means routinely applied for contacting a sample with a biological molecule such as an antibody, an antisense oligonucleotide and a PCR primer pair. For example, in one embodiment, the sample and the composition are contacted in a microwell plate or in a microvial adapted for the mixture of small volumes.

The methods of the invention provide for use of any type of antibody including, but not limited to, polyclonal and monoclonal antibodies which binds specifically with ZEB protein, or a fragment thereof.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion or a full-length protein of interest (i.e., the rodent or human ZEB proteins and polypeptides of the invention) and a portion of another protein such as a maltose binding protein or glutathione (GST) tag polypeptide portion, and/or a moiety such that the ZEB portion is rendered more immunogenic.

Monoclonal antibodies directed against full length or peptide fragments of a protein or peptide may be prepared by any procedure for the generation of monoclonal antibodies, such as those described, for example, in Harlow et al. (1988, In: Antibodies, A Laboratory Manual, Cold Spring Harbor, N.Y.) and in Tuszynski et al. (1988, Blood, 72:109–115). The desired peptide may be synthesized using chemical synthesis technology or, alternatively, DNA encoding the desired peptide may be cloned and expressed from an appropriate promoter sequence in cells suitable for the generation of large quantities of peptide. Peptides generated by the above techniques can be purified to render them suitable for use a immunogens to inject into mice.

The invention should not, however, be construed as being limited solely to these antibodies or to these portions of the ZEB protein antigens. The present invention also includes other antibodies, as that term is defined herein, to mouse and human ZEB protein, or portions thereof. Such antibodies bind ZEB protein and are suitable for use in a number of different applications to visualize ZEB protein such as Western blots, immunohistochemistry, and immunofluorescence microscopy.

The methods described herein provide means to generate antibodies that can specifically bind with full-length ZEB protein and/or any portion of a ZEB protein. The present invention is not limited to the use of full-length ZEB protein as an immunogen but also includes the use of an immunogenic portion of the ZEB protein to produce an antibody that binds specifically with a mammalian ZEB protein. That is, the invention includes immunizing an animal using an immunogenic portion, or antigenic determinant, of the ZEB protein.

The antibodies can be produced by immunizing an animal such as, but not limited to, a rabbit or a mouse, with a protein of the invention, or a portion thereof, or by immunizing an animal using a protein comprising at least a portion of ZEB protein, or a fusion protein including a portion comprising the appropriate ZEB protein amino acid residues covalently linked with a polypeptide tag portion comprising, for example, a maltose binding protein polypeptide tag portion. Additionally, smaller fragments of ZEB protein can also be used to produce antibodies that bind specifically with ZEB protein.

Various portions of an isolated ZEB polypeptide can be used to generate antibodies to either highly conserved regions of ZEB protein or to non-conserved regions of the polypeptide. Domains or regions of ZEB protein predicted to be immunodominant or highly conserved across mammalian species include, but are not limited to, the following: 1) a polypeptide encoded by nucleotides 200 through 1600 of the human cDNA and 2) a polypeptide encoded by nucleotides 2100 through 3000 of the human cDNA.

The amino acid sequence of ZEB protein and the identification of conserved and non-conserved epitopes or domains of the protein can be used to generate antibodies specific for a mammalian ZEB polypeptide. Such methods are well known in the art.

As mentioned above, non-conserved regions of a protein of interest can be more immunogenic than the highly conserved regions which are conserved among homologs of various organisms. Further, immunization using a non-conserved immunogenic portion can produce antibodies specific for the non-conserved region thereby producing antibodies that do not cross-react with other proteins which can share one or more conserved portions. Thus, one skilled in the art would appreciate that the non-conserved regions of each ZEB protein molecule can be used to produce antibodies that are specific only for that ZEB protein and do not cross-react non-specifically with ZEB proteins derived from other organisms, or proteins other than ZEB, derived from any species.

Alternatively, antibodies can also be generated using a region that is conserved among one or more ZEB protein molecules can be used to produce antibodies that react specifically with one or more mammalian ZEB proteins. Methods for producing antibodies that specifically bind with a conserved protein domain, which may otherwise be less immunogenic than other portions of the protein, are well-known in the art and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one ZEB protein and antibodies that bind specifically with more than one ZEB protein, including antibodies that bind specifically with all mammalian ZEB proteins.

Thus, the present invention encompasses antibodies that neutralize and/or inhibit ZEB protein activity (e.g., by inhibiting necessary ZEB protein receptor/ligand interactions) which antibodies can recognize one or more ZEB proteins, as well as ZEB proteins from various species (e.g., mouse, human, and/or rat).

The determination of percent homology (i.e. percent identity) described herein between two amino acid or nucleotide sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example, at the National Center for Biotechnology Information (NCBI) world wide web site having the universal resource locator www.ncbi.nlm.nih.gov/BLAST/. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www.ncbi.nlm.nih.gov.

The percent identity between two amino acid or nucleotide sequences can be determined using techniques similar to those described above, with or without allowing gaps. In calculating percent identity, typically exact matches are counted.

The invention encompasses polyclonal, monoclonal, synthetic antibodies, and the like, all capable of specifically binding ZEB protein, or a portion thereof. One skilled in the art would understand, based upon the disclosure provided herein, that one feature of the antibody of the invention is that the antibody binds specifically with ZEB protein, and does not substantially bind with other proteins with which ZEB is associated. That is, the antibody of the invention recognizes ZEB protein, or a fragment thereof (e.g., an immunogenic portion or antigenic determinant thereof), but does not substantially recognize other proteins for example, on Western blots, in immunostained cells, or in immunoprecipitates of ZEB protein using standard methods well-known in the art.

The antibodies of the invention can be used to localize the ZEB protein in a cell and to study the role(s) of the ZEB protein in cell processes. The antibodies can also be used to detect and/or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibodies of the present invention can be used to inhibit the activity of ZEB protein if the antibody binds to a region of ZEB and thereby alters the function and/or stability of ZEB protein. Such an inhibitory antibody could, for example, bind to ZEB and thus sterically hinder the association of ZEB with an essential binding partner. Thus, by administering the antibody to a cell or to the tissues of an animal or to the animal itself, the required ZEB protein receptor/ligand interactions are inhibited, such that the effects of ZEB protein mediated signaling are also inhibited.

Nucleic acids encoding the monoclonal antibody obtained using the procedures described herein may be cloned and sequenced using technology which is available in the art, and is described, for example, in Wright et al. (1992, Critical Rev. Immunol. 12:125–168), and the references cited therein.

Further, the antibody of the invention may be "humanized" using the technology described in, for example, Wright et al. (supra), and in the references cited therein, and in Gu et al. (1997, Thrombosis and Hematocyst 77:755–759), and other methods of humanizing antibodies well-known in the art.

To generate a phage antibody library, a cDNA library is first obtained from mRNA which is isolated from cells, e.g., the hybridoma, which expresses the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding with its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin.

The procedures presented above describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes the variable regions of the heavy and light chains of the antibody. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

The methods of the invention include the use of a ZEB antisense oligonucleotide. By way of example and not by limitation, the ZEB antisense oligonucleotide can be used in the methods of the invention as a detection reagent for detecting the presence of a ZEB mRNA and/or as an agent to inhibit the expression of a ZEB gene. Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes. The use of antisense methods to inhibit the translation of genes is known in the art, and is described, for example, in Marcus-Sakura (1988, Anal. Biochem. 172:289). Such antisense molecules may be provided to the cell via transfection and expression of DNA constructs encoding the antisense molecule as taught by Inoue (1993, U.S. Pat. No. 5,190,931).

In the method of the invention, the antisense oligonucleotide can be any type of antisense oligonucleotide known to the skilled artisan. In certain situations, it may be desirable to inhibit expression of ZEB protein, and the invention therefore includes compositions useful for inhibition of ZEB protein expression. Thus, the method of the invention uses an isolated nucleic acid complementary to a portion or all of a nucleic acid encoding a mammalian ZEB protein, which nucleic acid is in an antisense orientation with respect to transcription. Preferably, the antisense nucleic acid is complementary with a nucleic acid having at least about 30% homology with at least one of SEQ ID NO: 5 and SEQ ID NO: 6, or a fragment thereof. Preferably, the nucleic acid is about 35–55% homologous, more preferably, about 55–75% homologous, even more preferably, about 75–90% homologous, and most preferably, about 95% homologous to a nucleic acid sequence complementary to a portion or all of a nucleic acid sequence encoding a mammalian ZEB protein having the sequence of at least one of SEQ ID NO: 5, SEQ ID NO: 6, or a fragment thereof, which is in an antisense orientation with respect to transcription. Most preferably, the nucleic acid is complementary to a portion or all of a nucleic acid that is at least one of SEQ ID NO: 5, SEQ ID NO: 6, or a fragment thereof. Such antisense nucleic acid molecules serve to inhibit the expression, function, or both, of a ZEB protein molecule.

Alternatively, antisense molecules useful in the methods of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

The method of the invention also includes using ZEB-specific PCR primers. ZEB-specific PCR primers are useful for PCR amplification of a nucleic acid which encodes part or all of a ZEB protein. ZEB-specific PCR primers are thus useful as detection reagents since they facilitate the detection of ZEB mRNA in a cell by promoting the PCR amplification of cDNA generated from such ZEB mRNA.

A ZEB-specific primer can be any nucleic acid which binds specifically with a nucleic acid encoding ZEB protein. Examples of preferred ZEB-specific primers are described herein in the Experimental Examples as SEQ ID NO: 1 and SEQ ID NO: 2.

In one embodiment, at least one of the detection reagents in the composition is an antibody which binds specifically with ZEB protein. This method comprises incubating the sample with the composition for a period of time sufficient to permit detection of the ZEB protein. For example, where the detection reagent is an antibody Which binds specifically with ZEB protein, the sample and the composition are incubated for a period of time sufficient to allow the formation of a complex between the antibody and the ZEB protein. Alternatively, the detection reagent may be an antisense oligonucleotide which binds specifically with ZEB mRNA, the sample and the composition are incubated for a period of time sufficient to allow the formation of a complex between the ZEB mRNA and the antisense oligonucleotide.

The method also includes detecting the ZEB protein or the ZEB mRNA in the sample. ZEB protein can be detected by a number of different methods including, but not limited to polyacrylamide gel electrophoresis (PAGE) visualization, Western blotting, and immuno-histochemistry. ZEB mRNA can be detected by a number of different methods including, but not limited to, polymerase chain reaction (PCR) amplification of cDNA generated from ZEB RNA, Northern analysis, and RNase protection. Exemplary methods for the detection of ZEB mRNA molecules using antisense oligonucleotides as probes or ZEB-specific PCR primer pairs are described herein.

Based upon one or more of the amount and the location of the ZEB protein and/or the ZEB mRNA in one or more of the cells of the sample, a determination is made as to whether a cancer or tumor is present in the mammal. For example, when the sub-cellular localization of the ZEB protein in a sample derived from a population of cancer cells or a tumor differs from that of the ZEB protein in a control sample derived from matched, normal cells or tissue, the difference in the sub-cellular location of the ZEB protein is an indication of the presence of a cancer or a tumor in the mammal tested. Alternatively, when the expression levels of the ZEB protein and/or the ZEB mRNA are significantly different, either elevated or reduced, in a cancer cell or a tumor cell relative to the expression levels of the ZEB protein and/or the ZEB mRNA present in one or more cells of a matched sample of normal tissue or body fluid from the mammal, then this difference in the level of the ZEB protein and/or the ZEB mRNA is an indication of the presence of a cancer or tumor in a mammal.

By determining from one or more of the expression levels and/or cellular localization of the ZEB protein and/or ZEB mRNA in controls versus samples obtained from the mammal, a determination of whether a cancer or tumor is present in the mammal is made, thereby diagnosing a cancer or tumor in the mammal.

The invention also includes a method of staging the progression of a tumor in a cell or tissue sample obtained from a mammal. The tumor can be of any type, and is preferably an epithelial tumor. A biological sample isolated from a cancer patient is contacted with a composition comprising one or more detection reagents as described herein. The composition comprises at least one detection reagent in an amount effective to permit detection of the ZEB protein or the ZEB mRNA in the sample. The stage of progression of the tumor along the continuum from non-invasive and non-metastatic to invasive and metastatic can be determined as described herein. Depending on the type of tumor (e.g., an epithelial tumor), translocation of ZEB protein from the cytoplasm to the nucleus of a cell can be used as an indication of a late-stage tumor. Moreover, as shown herein, changes in ZEB protein levels can have profound effects on cellular response to apoptotic signals. Repression of apoptotic signals and/or loss of responsiveness to apoptotic signals can provide tumor cells with a significant growth advantage over normal cells. Information regarding ZEB protein levels thus can be used to advantage to facilitate diagnosis or staging of a tumor and/or predicting tumor response to a pharmaceutical agent that modulates cellular apoptosis or programmed cell death.

Staining of thin sections derived from normal and adenocarcinoma colon cells, for example, revealed that ZEB RNA transcript levels decreased dramatically in the dedifferentiated adenocarcinoma cells when compared to normal differentiated cells. Moreover, it was apparent that ZEB protein expression also increased dramatically as colon crypt cells differentiate and migrate to the tip of a villus. The ZEB expression pattern broadened from the cytoplasmic localization typically observed in younger crypt cells in the lower part of the villus spreading throughout the entirety of mature cells as they differentiate and migrate up the villus. Maximal ZEB staining was observed at the tip of the villus. Thus a correlation exists between of low levels of ZEB RNA transcript/protein levels and the de-differentiated" cancerous state.

Staining of thin sections derived from normal and transformed breast cells also revealed that ZEB RNA transcript levels decreased dramatically in transformed cells as compared to normal cells. Moreover, translocation of ZEB protein from the cytoplasm to the nucleus was observed during the progression of breast ductal epithelial cells from a normal state to ductal carcinoma in situ.

Staining of thin sections derived from normal and transformed ovarian cells also revealed that ZEB RNA transcript levels decreased dramatically in transformed cells as compared to normal cells.

Staining of thin sections derived from stomach cancer cells, however, revealed that in this tissue type, ZEB mRNA levels increased dramatically in tumor cells as compared to normal cells; as much as a 50× increase has been observed in some samples. Since gastric cancer is one of the most prevalent tumor types in people of Asian descent, utilizing modulations of ZEB transcript levels as an indicator for diagnosis, prognosis, and/or best mode for pharmaceutical intervention in a patient diagnosed with gastric cancer provides streamlining of treatment in patients afflicted with this type of cancer.

Staining of thin sections derived from normal and transformed prostate cells revealed that ZEB mRNA levels were elevated in tumor cells relative to those of normal cells.

Figure 13:
FIG. 13 shows the differential expression pattern of ZEB protein in melanoma cell lines derived from patients at different stages of melanoma disease progression.

Staining of cell lines derived from melanoma patients at different stages of disease has also revealed that a correlation exists between translocation of ZEB protein from the cytoplasm to the nucleus and degree of melanoma tumorigenicity (FIG. 13). These studies showed that ZEB protein was localized to the cytoplasm in a cell line taken from a patient with primary/radial growth phase (low grade, initial phase) melanoma. In a cell line taken from a patient with intermediate grade (vertical growth phase) melanoma, however, ZEB was expressed cell-wide. Significantly, ZEB was detected only in the nucleus of a cell line isolated from a patient with an advanced tumor (metastatic growth phase). These studies revealed a correlation between ZEB cellular localization and severity of disease which provides a facile assay with which to define the stage of melanoma progression. In a particular embodiment of the present invention, nuclear localization of ZEB can be used as an indicator of late stage, advanced melanoma.

The above information regarding modulation of ZEB RNA and protein expression levels and cellular localization thereof provides a framework with which a physician can provide improved care for a patient, the advantages of which include a more accurate diagnosis of tumor stage and, therefore, better assessment of the benefit to risk ratio that must be considered in any therapeutic regimen.

For example, diagnostic tools such as those described above provide a clinician valuable information as to the course of therapeutic intervention most appropriate for the treatment of the mammal from which such tumor cells or tissue samples were derived.

The methods of the present invention, therefore, provide a basic diagnostic tool to indicate the presence of a cancer cell or a tumor and a more sophisticated diagnostic tool to evaluate the stage or progression of said cancer cell or tumor.

Methods of Gene Therapy

The invention also includes a method of treating the cancer or a tumor in a mammal, preferably a human. The cancer or tumor can be of any of the types described herein. The method comprises administering to the mammal a composition comprising a ZEB antisense oligonucleotide, a construct encoding a ZEB antisense oligonucleotide, a dn ZEB protein, or a construct encoding a dn ZEB protein. Such methods provide therapeutic tools for the treatment of patients with tumors and may be particularly useful in the treatment of patients whose tumors have become resistant to standard therapeutic regimens, including those that utilize radiation and chemotherapy.

A ZEB antisense oligonucleotide can be any of the antisense oligonucleotides described herein which is specific for a ZEB mRNA molecule. The composition comprises a ZEB antisense oligonucleotide in an amount effective to de-repress an apoptotic pathway in a cancer or tumor cell in a mammal. The phrase "to de-repress an apoptotic pathway" as used herein relates to the induction of apoptotic, or programmed cell death, pathways following the abrogation of cellular signals that had heretofore been repressing or inhibiting apoptosis of such cells.

Figure 3A:
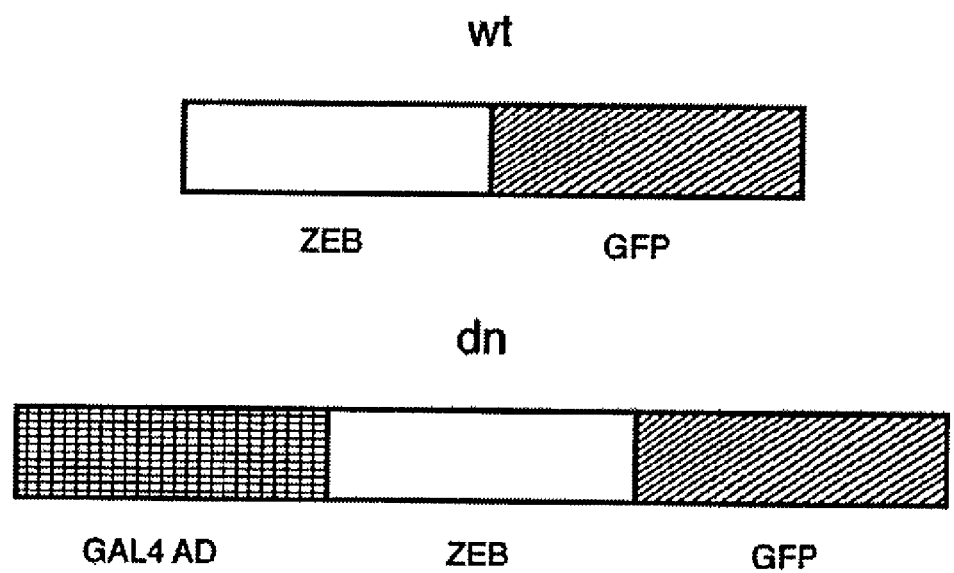
FIG. 3 reveals that dominant negative ZEB causes cells to apoptose. (A) Constructs indicated were cloned into a tetracycline-responsive expression vector (Clontech) and transiently transfected into various cell types. 48 hours post transfection, the inducing agent doxycycline was added to the culture medium to 2 micrograms/ml. 4 hours after induction, cells were treated as indicated in Materials and Methods for caspase activity using a cell-permeable, irreversibly binding, rhodamine-coupled pan-caspase inhibitor. (B) Jurkat (panels a, b, e, and f) and the pre-osteoblast cell line MC3T3 (panels c, d, g and h) (the fraction of cells that took-up the expression constructs) showed an apoptotic morphology (panels e and g) and were rhodamine-positive (panels f and h) when transfected with the dominant negative construct. The same cells transfected with the wt ZEB construct showed no differences from control GFP-only transfections (panels a–d and data not shown). All photomicrographs were taken 6 hours after administration of doxycycline, and representative fields of GFP-positive cells are shown.
Figure 3B:
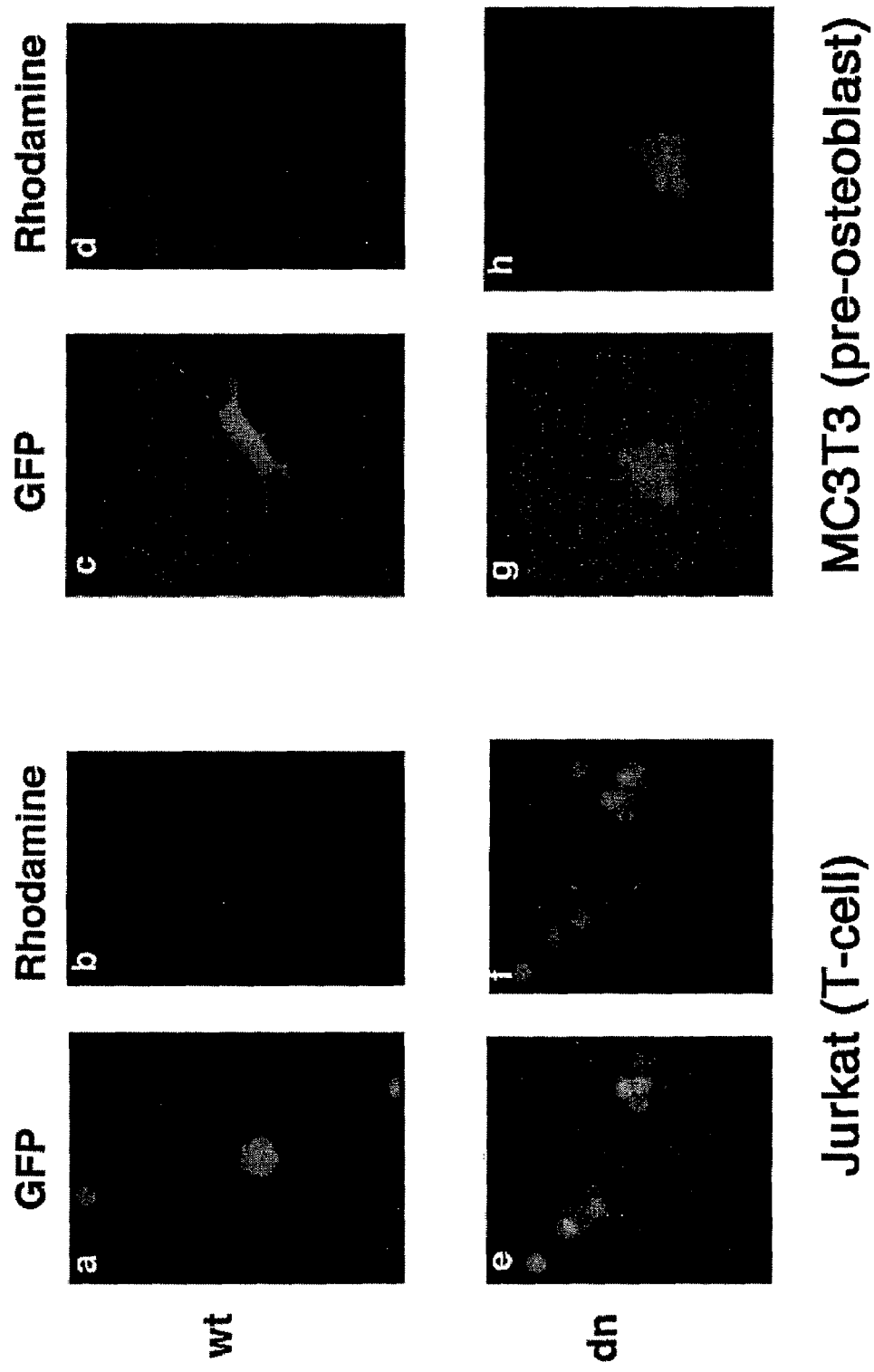

A dominant negative (dn) ZEB protein can also be used to de-repress an apoptotic pathway. A dn ZEB protein can be any of the dn ZEB proteins described herein which inhibit or counteract the activity of wildtype ZEB protein activity. A dn ZEB protein can be expressed and purified exogenously or produced by an expression construct in the cell or tumor to be treated. A description of a dn ZEB construct is provided in Example 1. This construct was used to generate a subset of the data shown in FIG. 3. In brief, the sequences encoding the DNA-binding carboxyl zinc-finger domain of ZEB were fused in frame at their 3' end to the sequence encoding green fluorescent protein (GFP) as depicted in FIG. 3A. To create a dn ZEB, sequences encoding the GAL4 activation domain were fused to the 5' end of the ZEB sequence.

Dominant negative versions of ZEB include, but are not limited to those having the same architecture as the dn ZEB proteins described above: GAL4-ZEB-GFP, in which the ZEB moiety is altered to include any number of mutations which will cause the entire construct to functionally inhibit endogenous ZEB activity, or to counteract endogenous ZEB activity by activating a gene through a ZEB binding site.

In addition, the GAL4 moiety can be removed, altered, mutated or substituted with a different activation domain. The activation domain of other well characterized transcriptional activators (for example, VP-16) could also be utilized. One of skill in the art would be aware of the plurality of transcriptional activators available and would choose an activation domain thereto that would be suitable for a particular experimental condition.

As a further alternative, DNA constructs comprising nucleic acid sequences encoding a dn ZEB polypeptide or an antisense ZEB molecule could be used in methods of gene therapy to treat a tumor which has become resistant to apoptosis. As described herein, dn ZEB polypeptides and antisense ZEB molecules can de-repress and/or activate apoptotic pathways in such tumors. Since repression or inactivation of apoptotic pathways is a common mechanisms whereby many cancer cells escape normal proliferative controls, such therapeutic intervention is beneficial to patients with tumors that are resistant to apoptosis.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target expression of nucleic acids encoding dn ZEB protein or antisense ZEB molecules to malignant tissues are preferred. Examples of selective targeting techiniques include receptor-mediated gene transfer, in which the nucleic acid is linked to a protein ligand via polylysine, with the ligand being specific for a receptor present on the surface of a target cells. Microcapsule based delivery systems are also available for delivery of nucleic acids to targeted cell types.

The composition comprising a ZEB antisense oligonucleotide, a construct encoding a ZEB antisense oligonucleotide, a dn ZEB protein, or a construct encoding a dn ZEB protein can be administered to a mammal using any route of administration known to the skilled artisan. Examples of preferred methods of administration include, but are not limited to, topical application of the compound via an appropriate solvent (for example, DMSO), direct injection of a solution of the compound into the cells of a solid tumor mass, liposomal-mediated delivery, and timed release via any appropriate surgically implanted device.

A composition comprising a ZEB antisense oligonucleotide includes, but is not limited to, those ZEB antisense oligonucleotides described herein which are present in an amount effective to reduce the levels of endogenous ZEB up to or beyond a threshold level to achieve a de-repression of a member of an apoptotic pathway or an entire pathway in a mammalian tumor or cancer cell.

A composition comprising a construct encoding a ZEB antisense molecule includes, but is not limited to, those constructs encoding ZEB antisense molecules described herein. A construct encoding a ZEB antisense molecule is present in a composition in an amount effective to express ZEB antisense molecules in a target cell at levels sufficient to reduce the amount of endogenous ZEB up to or beyond a threshold level to achieve a de-repression of a member of an apoptotic pathway or an entire pathway in a mammalian tumor or cancer cell.

A composition comprising a dn ZEB protein includes, but is not limited to, those dn ZEB proteins described herein which are present in an amount effective to inhibit the activity of endogenous ZEB up to or beyond a threshold level to achieve a de-repression of a member of an apoptotic pathway or an entire pathway in a mammalian tumor or cancer cell.

A composition comprising a construct encoding a dn ZEB protein includes, but is not limited to, those constructs encoding dn ZEB proteins described herein. A construct encoding a dn ZEB protein is present in a composition in an amount effective to express dn ZEB protein at levels sufficient to inhibit the activity of endogenous ZEB up to or beyond a threshold level to achieve a de-repression of a member of an apoptotic pathway or an entire pathway in a mammalian tumor or cancer cell.

In a preferred embodiment, the tumor or cancer cell is in a mammal, preferably a human. Preferably, the tumor or cancer cell is an epithelial tumor or cancer cell.

In one embodiment, the composition comprising the ZEB antisense oligonucleotide, a construct encoding a ZEB antisense oligonucleotide, a dn ZEB protein, or a construct encoding a dn ZEB protein is in the form of a pharmaceutical composition. Preferably, the pharmaceutical composition comprises a pharmaceutically acceptable carrier.

The pharmaceutical composition can be used to administer the ZEB antisense oligonucleotide, a construct encoding a ZEB antisense oligonucleotide, a dn ZEB protein, or a construct encoding a dn ZEB protein to a cell, a tissue, or a mammal to modulate the expression of ZEB protein or modulate the activity of endogenous ZEB protein in a cell, a tissue, or a mammal. The compositions are useful to treat a cancer or a tumor which is associated with altered expression or sub-cellular location of ZEB protein, e.g., where a cancer or a tumor is associated with an altered level of ZEB protein expression or a translocation of ZEB protein from the cytoplasm or from a cell-wide distribution to the nuclear distribution, the pharmaceutical composition can be used to lower the expression of ZEB protein.

The pharmaceutical composition for the administration of the ZEB antisense oligonucleotide, a construct encoding a ZEB antisense oligonucleotide, a dn ZEB protein, or a construct encoding a dn ZEB protein can be used for 1) relief of repression of apoptotic signaling pathways or 2) relief of repression, accompanied by subsequent activation of a gene encoding a component of an apoptotic pathway or a subset or all of the genes encoding an entire apoptotic pathway.

For administration to the mammal, the ZEB antisense oligonucleotide, a construct encoding a ZEB antisense oligonucleotide, a dn ZEB protein, or a construct encoding a dn ZEB protein can be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to mammals of all sorts. Modification of pharmaceutical compositions suitable for administration to humans in order to render the compositions suitable for administration to various animals is well understood, and veterinary pharmacologists routinely design and perform such modifications. Subjects to which administration of the pharmaceutical compositions of the invention is contemplated include, but are not limited to, humans and other primates, mammals including commercially relevant mammals such as cattle, pigs, horses, sheep, cats, and dogs.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the ZEB antisense oligonucleotide, a construct encoding a ZEB antisense oligonucleotide, a dn ZEB protein, or a construct encoding a dn ZEB protein which may be administered to a mammal, preferably a human, will vary depending upon any number of factors, including but not limited to, the type of mammal and type of cancer or tumor being treated, the age of the animal and the route of administration.

A ZEB antisense oligonucleotide, a construct encoding a ZEB antisense oligonucleotide, a dn ZEB protein, or a construct encoding a dn ZEB protein can be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the cancer or tumor being treated, the type and age of the mammal, etc.

The invention also includes a kit for treating a cancer or a tumor in a mammal, preferably a human. The cancer or tumor can be of any of the types described herein, and is preferably an epithelial cancer or tumor. The kit comprises compositions of the invention comprising a ZEB antisense oligonucleotide, a construct encoding a ZEB antisense oligonucleotide, a dn ZEB protein, or a construct encoding a dn ZEB protein in an amounts effective to de-repress an apoptotic pathway in a cancer or tumor cell in a mammal. The kit also comprises an instructional material which directs the use of the compositions for the function of treating a cancer or a tumor in a mammal by administering at least one of the compositions to a mammal using any route of administration known to the skilled artisan.

As used herein, an "instructional material" includes a publication, a recording, a diagram, or any other medium of expression which directs or dictates the use of the components of a kit for performing the function of a method of the invention described herein. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The invention also includes a kit for diagnosing a cancer or a tumor in a mammal. The cancer or tumor can be of any of the types described herein, and is preferably an epithelial cancer or tumor. The kit comprises a container or a sample tube, or the like, for storing a sample of a cell, a population of cells, a tissue or a body fluid obtained from the mammal.

The kit also comprises a composition comprising one or more detection reagents selected from the group consisting of an antibody which specifically binds with ZEB protein, an antisense oligonucleotide which specifically binds with ZEB mRNA, and a ZEB-specific PCR primer pair. These detection reagents are as described herein in the inventive methods and compositions. The composition comprises the one or more detection reagents in an amount effective to permit detection of the ZEB protein or the ZEB mRNA in the sample. Detection of the ZEB protein or the ZEB mRNA is accomplished using any of the methods described herein or known to a skilled artisan for detecting a specific protein or specific mRNA molecule within a biological sample.

The kit also comprises an instructional material which directs the use of the composition and the sample for the function of determining the amount and the location of the ZEB protein or the ZEB mRNA in one or more cells of the sample. The instructional material also directs the correlation of the amount and the location of the ZEB protein or the ZEB mRNA in the cells of the sample with the diagnosis of a cancer or a tumor in the mammal.

The invention also includes a kit for staging a tumor in a mammal. The tumor can be of any of the types described herein, and is preferably an epithelial tumor. The kit comprises a container or a sample tube, or the like, for storing a tumor cell or tissue sample obtained from the mammal.

The kit also includes an instructional material which directs the use of the composition and the sample for the function of determining the amount and the location of the ZEB protein or the ZEB mRNA in one or more cells of said sample. The instructional material also directs the correlation of the amount and location of the ZEB protein or the ZEB mRNA in one or more cells of the sample with the stage of progression of the tumor in the mammal.

EXAMPLE 1

Methods suitable for the detection of endogenous steady-state ZEB mRNA levels are provided which facilitate a qualitative assessment of ZEB mRNA levels from particular biological samples. Methods for the modulation of ZEB-associated molecules in such samples, such as mRNA and protein are also disclosed.

The following materials and methods are provided to facilitate the practice of Example 1.

I. Detection of ZEB mRNA

The mRNA encoding ZEB protein was detected using a probe as described in Genetta et. al., Mol. Cell. Biol. 14:6153. The probe comprises, for the human ZEB protein, the entire coding sequence from nucleotide 4 to nucleotide 3378 (SEQ ID NO: 9; FIG. 9), and for the mouse ZEB protein, the entire coding sequence from nucleotide 37 to 3390 (SEQ ID NO: 11; FIG. 11).

Any standard detection system known in the art can be used to detect a full-length mRNA from any vertebrate source after the mRNA is labeled using any type of standard methodology. The mRNA can be isolated, for example, from tissue or biopsy samples as well as from primary or established cell lines.

Using a high stringency of detection [i.e., 68° C. for 15 minutes in 0.1× sodium chloride/sodium citrate (SSC), 0.1% SDS; repeating once], a unique band for ZEB at approximately 5.3 kilobases can be detected in a standard Northern blot analysis.

II. Relative-Quantitative PCR Detection of ZEB mRNA.

An adaptation of a standard RT-PCR method is used to detect relative levels of ZEB mRNA obtained from any source. Briefly, PCR primers which specifically amplify the gene of interest (e.g., ZEB) are biotinylated at their 5' ends. This modification is used for the detection of the subsequent PCR product. Additionally, this method utilizes a 1:49 ratio of 5' biotinylated to unmodified PCR primers specific for the internal "housekeeping" gene glyceraldehyde phosphate dehydrogenase (GAPDH) to provide an internal control with which to normalize for the amount of mRNA derived from different sources. The amount of the GAPDH PCR product, as indicated by the intensity of the signal, can be analyzed in parallel with that of the ZEB product to ensure that the detected signals are within the linear range of detection of the X-ray film. This method allows for rapid and sensitive detection of relative quantitative levels of ZEB mRNA in samples obtained from different sources.

```
The PCR primers used to detect a unique, ZEB-
specific
298 base-pair product are:
5': CAA GTG CCA ACC CCA TAA AT    (SEQ ID NO:1)

3': TTT TTG GGC GGT GTA GAA TC    (SEQ ID NO:2)

The PCR primers used to detect a unique, GAPDH-
specific
band of 160 base pairs are:
5': CAT CAA GAA GGT GGT GAA GC    (SEQ ID NO:3)

3': GAG CTT GAC AAA GTG GTC GT    (SEQ ID NO:4)
```

A. Synthesis of First-Strand cDNA

Total RNA is isolated from a given tissue or cell line using the Totally RNA kit (Ambion), according to the manufacturer's instructions. Complementary DNA (cDNA) was prepared using 1 microgram of RNA in a total volume of 10 microliters containing 75 nanograms of random hexamers (Life Technologies, Inc.), 0.5 millimolar dNTPs, and 100 Units of Superscript II Reverse Transcriptase (Life Technologies, Inc.) in a reaction buffer consisting of 20 millimolar Tris-Cl (pH 8.4), 50 millimolar KCl, 2.5 millimolar $MgCl_2$, and 10 millimolar DTT. The RNA was denatured at 80° C. for 10 minutes and chilled immediately on ice. The reaction was incubated at 23° C. for 10 minutes, then at 42° C. for 50 minutes, and finally at 70° C. for 15 minutes. The RNA template, from which the cDNA was reversed transcribed, was then digested by adding two Units of RNAse H (Life Technologies, Inc.) and incubating at 37° C. for 30 minutes.

B. PCR

One microliter of the first-strand cDNA product synthesized as described above was added directly to a 10 microliter PCR reaction containing 50 millimolar KCl, 10 millimolar Tris-Cl (pH 8.3), 2 millimolar $MgCl_2$, 200 micromolar dNTPs, 0.4 micromolar primers, and 0.5 Units of AmpliTaq Gold Polymerase (Perkin Elmer). A 1:49 ratio of biotinylated:unmodified GAPDH-specific primers was used to generate the GAPDH PCR product. Diluting the biotinylated GAPDH primers reduced the detectable signal of the GAPDH product to within the linear range of detection of X-ray film. To visualize ZEB cDNA, derived from the relatively rare RNA encoding ZEB, it was necessary to utilize only biotinylated primers so as to maximize the intensity of the signal generated for the ZEB PCR product. PCR amplification to generate the ZEB and GAPDH PCR products was limited to about 20 cycles, so as to ensure that the amplification process proceeded in the linear range. The PCR cycling conditions were as follows: 95° C., 10 minutes—1 cycle; 95° C., 30 seconds, 55° C., 30 seconds, 72° C., 90 seconds—20 cycles; 72° C., 5 minutes.

C. Visualization of PCR Products

ZEB- and GAPDH-specific PCR products are separated on a 10% non-denaturing acrylamide vertical mini-gel, followed by electroblotting onto a nylon membrane. The bands of interest were visualized using a standard chemiluminescent methodology (Tropix, Inc.), which utilizes alkaline phosphatase-coupled avidin as the primary reagent.

III. Preparation of Antibodies for Use in the Detection of ZEB Protein

A. Production of Polyclonal Anti-ZEB Antibodies in Rabbits

Polyclonal antibodies which bind specifically to different fragments of the human ZEB protein were prepared as follows. Rabbit polyclonal antibodies were raised against two distinct fragments of the human ZEB protein. A 920 base-pair fragment (nucleotide 2537 to nucleotide 3473) encoding the carboxyl terminal zinc-finger domain of the human ZEB protein and a 646 base-pair fragment (nucleotides 481 through 1132) encoding the amino terminal zinc-finger domain were each fused in frame to the coding region of the entire glutathione-S-transferase (GST) coding region harbored in the prokaryotic expression vector pGEX-2× (Pharmacia). Inducing the expression of the fusion proteins and their subsequent isolation from bacterial culture yielded a 56 kiloDalton ZEB carboxyl terminal-GST fusion protein and a 48 kiloDalton ZEB amino terminal-GST fusion protein.

The fusion proteins were grown in large-scale bacterial culture and approximately 1 milligram of each was purified by affinity chromatography on a GST-binding column. The relative purity of each GST fusion protein was determined by SDS-PAGE analysis, which revealed that the fusion protein preparations were greater than 90% pure. The purified fusion proteins were lyophilized and sent to a commercial producer of antibodies (Hazelton Laboratories, Denver, Pa.). This vendor resuspended the dried fusion proteins in the appropriate adjuvant and injected them individually into separate rabbits for the production of polyclonal antibodies. Periodic test bleeds obtained from these immunized rabbits were analyzed for the presence of polyclonal antibodies capable of specific binding with and thus detection of in vitro translated ZEB protein by Western blot assay. After verifying that the sera from these rabbits contained anti-ZEB specific antibodies, the rabbits were terminally bled. Thus, polyclonal antibodies were generated that specifically recognized either the carboxy terminal or the amino terminal zinc-finger domains of ZEB protein.

B. Affinity Purification of the Anti-ZEB Antibodies

Each polyclonal antibody preparation was affinity purified as follows. All test bleeds were combined with the terminal bleed from the appropriate immunized rabbit (total yield of about 180 milliliters per animal), and the serum was cleared by centrifugation at 3,000 g for 30 minutes. A saturated solution of ammonium sulfate was slowly added, with stirring, to bring the cleared serum to a final concentration of 50%.(w/v) ammonium sulfate. After incubation at 4° C. overnight, the ammonium sulfate precipitate was pelleted by centrifugation at 3000 g for 30 minutes. The supernatant was discarded and the pellet was resuspended in 80 milliliters of phosphate buffered saline (PBS). This solution was dialysed overnight at 4° C. against three changes of PBS. The dialyzed solution was cleared by centrifugation at 3000 g for 30 minutes and the anti-ZEB antibodies contained therein were subjected to affinity purification as described below.

A recombinant baculovirus was engineered to comprise a nearly full-length fragment of the ZEB cDNA (nucleotides 241 to 3460), operably linked to the polyhedrin promoter. Recombinant baculovirus expressing the fragment of ZEB protein encoded by the ZEB cDNA fragment was identified and propagated in Tn5 cells, which provided for the secretion of ZEB protein into the culture medium. Infected Tn5 cells were grown in rotation bottles to yield eight liters of culture medium containing secreted ZEB protein. The cells were pelleted and a protease inhibitor cocktail was added to the media immediately thereafter to prevent degradation of the secreted ZEB protein. The ZEB protein was concentrated by ammonium sulfate precipitation, dialyzed, and further concentrated by ultrafiltration. The yield from this process was approximately 400 milligrams of relatively pure ZEB protein per eight liters of medium.

The affinity chromatography column used for the purification of anti-ZEB polyclonal antibodies was prepared by chemically coupling approximately 100 milligrams of baculovirus generated ZEB protein (described above) to cyanogen bromide-activated Sepharose-4 beads (Pharmacia Biotech). The coupled beads were then packed into a column. Each of the partially purified antibody solutions described above (containing either anti-amino terminal or anti-carboxyl terminal zinc-finger domain antibodies) were then individually passed through the affinity column, thereby facilitating binding of ZEB specific antibodies contained thereto to the immobilized ZEB protein. The column was then washed extensively to remove any contaminants that had bound to the column non-specifically, and the antibodies which had bound specifically to the immobilized ZEB protein were eluted at low pH. Glycerol was added to the eluted purified antibody solutions to a final concentration of 50% (v/v) and the antibody solutions were stored long term at −80° C. Working aliquots of the antibodies were stored at 4° C.

IV. Recombinant DNA Constructs

All recombinant constructs were generated using standard methods and protocols (Ausubel et al., 1992), and verified by sequencing in both directions by the University of Pennsylvania Cell Center Sequencing Facility. Dominant negative(dn) nucleic acids encoding a ZEB fusion protein comprised the GAL4 activation domain (AD), sequences encoding ZEB or specific domains of ZEB, and GFP. The ZEB moiety included in the above fusion protein construct was comprised of one of the following: the entire coding region of the murine cDNA, sequences encoding the first third (20–919 nt) of the amino terminus, or sequences encoding the last third (2582–3037 nt) of the carboxyl terminus. To synthesize each of the fusion protein constructs, PCR products of the GAL4 AD, one of the three ZEB moieties described above, and a GFP fragment were generated into which 15 nt overhanging ends were incorporated to facilitate bridging of the PCR products in subsequent amplification reactions. Approximately 5–10 ng of each of the three fragments having complementary overhanging ends was then used for templates in a second PCR reaction that included only the 5' (top) primer used in the synthesis of the GAL4 fragment, and the 3' (bottom) primer used in the synthesis of the GFP fragment. The resulting "bridge" PCR product, comprising the GAL4 AD, a ZEB moiety, and a GFP fragment, was gel-purified, restriction digested, and ligated into PTRE downstream of the tetracycline-repressible CMV promoter (Clontech). A similar construct, comprising the entire coding region of ZEB linked in frame to the GFP fragment, but lacking the GAL4 activation domain, was synthesized to express wild-type ZEB-GFP. CtBP1 was a generous gift of Y. Higashi, and the p21

Luciferase reporter was a kind gift of W. el-Deiry. SHP-1 cDNA was kindly provided by Dr. J. Johnston from DNAX, Palo ALTO, Calif. and cloned into the expression vector pcDNA3 (Invitrogen).

V. Yeast Two-hybrid Screen

Murine ZEB cDNA (129–3240 nt) was cloned in frame with the GAL4 DNA-binding domain in the yeast vector pAS21 (the "bait" fusion protein). A "prey" library was generated by fusing cDNA from a mouse embryonic day 11 cDNA library (Clontech) in frame to the GAL4-activation domain (GAL4-AD). The ZEB bait construct and the prey library were used in a standard yeast two-hybrid screen in the yeast strain Y-190 (Fields and Song, 1989, Nature 340:245–6). Of the 58 true positives (verified through the complementation of auxotrophy by plate selection), nucleotide sequencing revealed that two clones (#43 and #10) were identical to the 3' end of p53BP1. The longer of these, clone #43, was 1768 nt long, comprising the 3'-most 1434 bases of the p53 BP1 cDNA, followed by 334 bases of 3' un-translated region. The other clone (#10), a truncated version of clone #43, was not used further. This interaction was verified by testing co-transformants on beta-galactosidase plates.

The ZEB-p53BP1 interaction domains were narrowed by generating overlapping PCR fragments of ZEB. Each primer pair incorporated a Bam HI site into the 5' end of the PCR product with an Nco I site at the 3' end, and these were cloned into the yeast expression vector pAS2-1. Each of the ZEB fragments was co-transfected with the #43 p53BP1 clone into Y-190, and beta-galactosidase assays were performed on liquid cultures derived from colonies that grew on -LEU/-TRP/-HIS selective plates.

VI. Expression of GST Proteins and Pull-down Assay

Full length ZEB was cloned into the bacterial expression plasmid GST-KG and purified as described (Genetta et al., 1994, Mol. Cell Biol. 14:6153–6163). The full length p53BP1 (a kind gift of K. Iwabuchi) and the carboxyl fragment derived from the yeast two-hybrid screen were cloned into the pGEM vector (Promega) and in vitro translated protein products were generated in the presence of $^{35}$S methionine using T7 RNA polymerase in the TNT Coupled Reticulocyte system (Promega). For GST pull-down experiments, 2 microliters of the purified ZEB-GST protein (made to 50% glycerol for long term storage at −80° C.) was incubated with 10 microliters of translation product (direct from the tube) and ZEB-bound peptides were isolated using glutathione-agarose beads (Sigma). To demonstrate the specificity of the ZEB-p53BP1 interaction, HA-tagged p53BP1 carboxyl fragment was in vitro translated as above in the presence of unlabeled methionine, and affinity purified using anti-HA antibody coupled to agarose beads (Roche).

VII. Tissue Culture and Transfections

All cell lines were maintained in a 37° C. humidified incubator in an atmosphere of 5% $CO_2$. Jurkat cells were maintained in RPMI medium with 10% fetal calf serum, supplemented with penicillin, streptomycin and glutamine. NIH 3T3 and MC3T3 pre-osteoblast fibroblasts were each maintained in DMEM medium with 10% fetal calf serum, supplemented with penicillin, streptomycin and glutamine. Jurkat cells ($2 \times 10^7$) were transfected via electroporation at 250 mV and 975 mF, using a total of 30 micrograms of DNA (the empty vector PBSK was used as carrier to equalize all transfections for 30 micrograms total DNA). Adherent cells were transiently transfected using the liposomal reagent Fugene (Roche), according to the manufacturer's instructions. SHP-1-expressing stable constructs were prepared as follows. Human Jurkat T-cells ($10^7$) were electroporated as above with 10 micrograms of pcDNA3-SHP-1. After selection in G418, single cell clones were isolated by limiting dilution (Ausubel et al., 1992) for further analysis. The resulting stable lines were maintained using G418 at an effective concentration of 1 mg/ml.

VIII. Antisense Experiments

Morpholino oligonucleotides (Genetools, Corvalis, Oreg.), in which the ribose moiety is replaced by a morpholine ring, were labeled by the manufacturer at their 3' end with flourescein. The sequence of the anti-sense ZEB oligo was: 5'-GGG CCA TCC GCC ATG ATC CTC TCG C-3' (SEQ ID NO: 5); the mis-sense control oligo sequence (with alterations in lower case) was: GGG gCA TgC GCC ATG ATC gTC TgG C-3' (SEQ ID NO: 6). Oligos were delivered to the tissue culture media according to the manufacturer's protocol via the EPEI cationic liposomal reagent (GeneTools), and cells were observed at regular intervals. Flourescent cells were photographed using a CCD color video camera.

IX. Western Blot Analysis

Six hours after administering antisense (or control missense) oligonucleotides, parallel transfections of NIH 3T3 cells in 10 cm tissue culture dishes were lysed following the addition of 600 microliters of SDS-PAGE loading buffer (Ausubel et al., 1992). Lysed cells were passed through a 27 gauge needle to shear the DNA contained therein, boiled for 10 min. and aliquots loaded directly onto a 10% denaturing gel for SDS-PAGE. Separated proteins were electrophoretically transferred to a nitrocellulose membrane, which was blocked and incubated with a 1:1000 dilution of a polyclonal anti-hamster ZEB antibody (a kind gift of M. Magnusson) for 1 hour at 4° C. After washing with blocking buffer plus 0.2% Tween-20 detergent (3×15 min.), the blot was incubated with a 1:1500 dilution of a biotinylated goat anti-rabbit antibody (Vector Labs) for 1 hour at room temperature. Following three 15 min. washes in Tris buffered saline (TBS) containing 0.2% Tween 20, the blot was incubated with a streptavidin-HRP solution (Dako), and developed in a calorimetric assay containing 3–3'-diamino-benzidine. To detect expression of SHP-1, cell lysates were prepared using 1% NP-40 lysis buffer with protease and phosphatase inhibitors (Ausubel et al., 1992). An equivalent of 1 million cells were loaded per lane. After protein transfer, the membrane was blocked for 0.5 hour in 3% non-fat milk, incubated with anti-SHP-1 polyclonal antibody at a dilution of 1:1000 (Santa Cruz) for 1 hour, washed extensively, incubated with secondary antibody for 45 min, and washed extensively again. The membranes were then incubated with a tertiary peroxidase-conjugated antibody to generate a detectable signal and developed using the ECL chemiluminescence reagents (Amersham Life Science).

X. Induction of Tetracycline-responsive Constructs.

All cell lines, except Jurkat cells, were transiently transfected with both the pTRE tetracycline-inducible expression constructs described above (harboring either the wild-type or dn ZEB-GFP fusion protein sequences) and a plasmid encoding the "Tet-ON" repressor protein (which constitutively expresses a tetracycline-VP16 fusion protein that will bind to its cognate binding site in the pTRE vectors only in the presence of tetracycline or the tetracycline analogue doxycycline). The Jurkat line was purchased from Clontech as a hygromycin-resistant (100 microgram/ml for maintenance) line stably expressing the "Tet-ON" fusion protein.

Only the PTRE expression constructs were used, therefore, to transiently transfect these cells. Forty-eight hours after transfection, the tetracycline-responsive constructs were induced using the tetracycline analogue, doxycycline (Sigma) at a final concentration of 2 micrograms/ml of cell culture media. Cells were then directly monitored, utilizing an inverted microscope, for the presence of green fluorescence due to the expression of the GFP fusion proteins and for the appearance of an apoptotic morphology. Detection of active caspases (a biochemical indicator of apoptosis) was carried out using the CaspaTag Kit (Intergen, Purchase, N.Y.). This kit employs a cell membrane-permeable sulforhodamine-labeled derivative of benzyloxycarbonyl valylalnylaspartic acid flouromethyl ketone (zVAD-FMK), which irreversibly binds to and inhibits activated caspase-1, -2, -3, -4, -5, -6, -7, -8, and -9. Flourescent cells were photographed using a CCD color video camera.

XI. Gamma-irradiation of Jurkat Cells

Cells were transiently transfected with the tetracycline-inducible wild-type or dominant negative ZEB constructs in the pTRE vector as described. Forty-eight hours later, doxycycline was added to the media to induce fusion protein expression and the cells were returned to the 37° C. incubator for an additional 4 hours. 10 ml aliquots of cells ($1 \times 10^6$ cells/ml) were then subjected to either 2.5, 5, or 10 Grey (Gy) of gamma radiation from a $^{137}$Cs source (Iomedic Model Gammator M-38-1), and then returned to the 37° C. incubator. Aliquots of the irradiated cells were removed at the indicated time points and analyzed for the presence of apoptotic cells using the rhodamine-coupled pan-caspase inhibitor (zVAD-FMK) as described above. For each sample, 5 separate fields of 100 cells were scored for single or double-positive staining. The results of three separate experiments were averaged for each construct. Standard errors of the mean were calculated for each group.

XII. Relative Quantitative RT-PCR

The protocol of Ikegaki (Eggert et al., 2000, Biotechniques 28:681–691) was used, which allows for quantitation of levels of ZEB mRNA relative to those of the housekeeping gene GAPDH in a single PCR reaction. Total RNA was isolated from Jurkat cells according to established protocols (Ausubel et al., 1992). One microgram of total RNA was reverse transcribed in a 10 microliter reaction with 20 mM Tris-Cl (pH 8.4), 50 mM KCl, 2.5 mM MgCl2, 10 mM DTT, 75 ng random hexamers (Life Technologies), 0.5 mM dNTPs, and 100 U Superscript II Reverse Transcriptase (Life Technologies). The RNA was first denatured at 80° C. for 10 min, chilled immediately on ice, and then added to the remaining reaction of above components pre-warmed to room temperature. The reaction was incubated at 23° C. for 10 min, then at 42° C. for 50 min., and finally at 70° C. for 15 min. Following reverse transcription to generate cDNA, the RNA template was digested by adding two units of RNAse H (Life Technologies) and incubating at 37° C. for 30 min. The PCR reaction included primers biotinylated at their 5' ends to enable the visualization of resultant products. Primers unique to ZEB, yielding a 257-bp PCR product (Postigo and Dean, 2000, Proc. Natl. Acad. Sci. (U.S.A.) 97:6391–6396) were: Top, 5'-ATA AGC AGT AAG AAA TGT ATC AGC TTG ATA CCT GTG AAT GGG-3' (SEQ ID NO: 7), Bottom 5'-ATT TTG TAA AGG GGT TGA ACA GTT GAT TCC TGA AGC AAC CAC-3' (SEQ ID NO: 8); for the 160 bp GAPDH PCR product: Top, 5'-CAT CAA GAA GGT GGT GAA GC-3' (SEQ ID NO: 3), bottom, 5'-GAG CTT GAC AAA GTG GTC GT-3' (SEQ ID NO: 4). Biotinylated primers were used exclusively to synthesize the ZEB fragment, while a ratio of biotinylated to unmodified primers of 1:49 was used to generate the GAPDH product. Diluting the biotinylated GAPDH primers reduced the signal from the GAPDH product to within the linear range of detection on X-ray film, commensurate with the levels of the ZEB product. 1 microliter of the first-strand product from the RT reaction was used in a 10 microliter PCR reaction containing 50 mM KCl, 10 mM Tris-Cl (pH 8.3), 2 mM MgCl2, 200 mM dNTPs, 0.4 mM each primer, and 0.5 Units of AmpliTaq Gold Polymerase (Perkin-Elmer). Cycling conditions were one cycle of 95° C., 10 min; twenty cycles of 95° C., 30 sec., 55° C., 30 sec., 72° C., 90 sec.; and one cycle of 72° C., 5 min. ZEB- and GAPDH-specific PCR fragments products were separated on a 10% non-denaturing acrylamide vertical mini-gel, followed by electroblotting onto a nylon membrane. The biotinylated bands were visualized via a standard chemiluminescent method employing an avidin-coupled alkaline phosphatase (Tropix, Inc.).

RESULTS

ZEB Interacts with the C-terminal Domain of p53BP1.

Figure 1C:
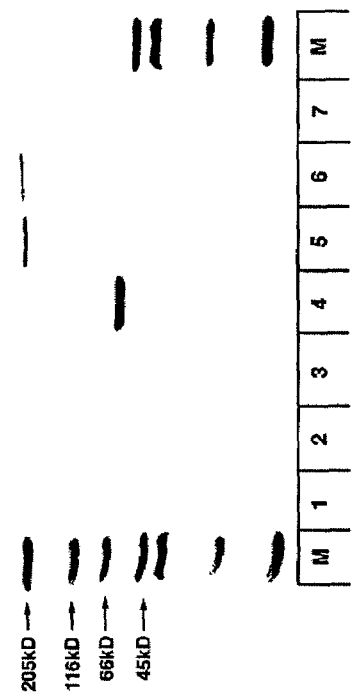
Figure 1A:
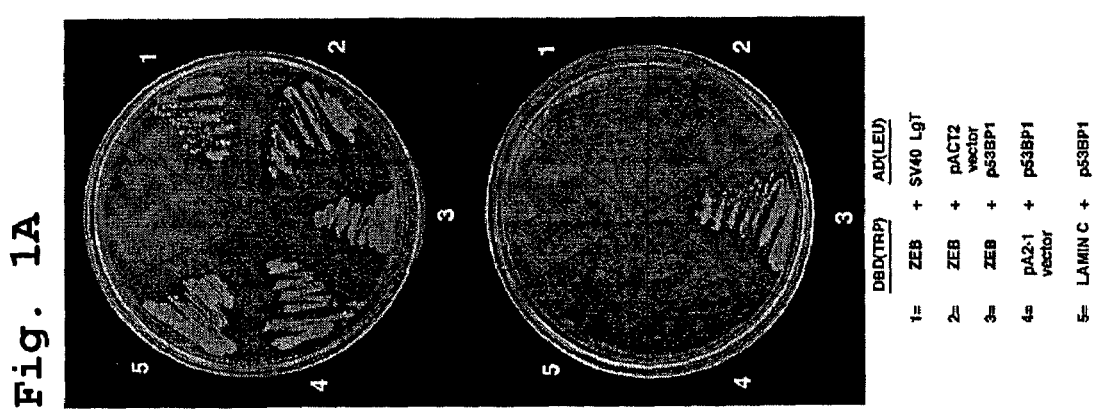

To identify novel proteins that interact with ZEB, a nearly full-length version of the murine ZEB cDNA (Genetta and Kadesch, 1996, Gene 169:289–290) was used as the bait in a yeast two-hybrid screen against a day E11 whole mouse embryo cDNA prey library. Of the 58 unique ZEB-interacting clones, two (#10 and #43) were identified by sequence analysis as cDNA fragments coding for the carboxyl-terminal domains of p53BP1 (Iwabuchi et al., 1994, Proc. Natl. Acad. Sci. (USA) 91:6098–6102; Iwabuchi et al., 1998, J. Biol. Chem. 273: 26061–26068). The reaction was specific, as only the ZEB-p53BP1 co-transformed colonies grew in the selective media (FIG. 1A). The two-hybrid system was also used to define the domain critical for the p53BP1 interaction to the mid-portion of ZEB, between the homeodomain and the proximal zinc-finger in three finger cluster of the carboxyl-terminal domain (FIG. 1B). As expected from the yeast two hybrid screen, the region of p53BP1 sufficient for ZEB binding was the carboxyl-terminal fragment.

Interestingly, this region of p53BP1 shares significant sequence homology with the carboxyl-terminal domain of the breast and ovarian cancer susceptibility gene, BRCA1 (Weber et al., 1995, Breast Cancer Res. Treat. 33:115–124; Welcsh et al., 2000, Trends Genet. 16:69–74; Abbott et al., 1999, J. Biol. Chem. 274:18808–18812; Miyake et al., 2000, . J. Biol. Chem. 275:40169–40173; Hu et al., 1999, Genes Dev. 13:637–642).

Figure 2:
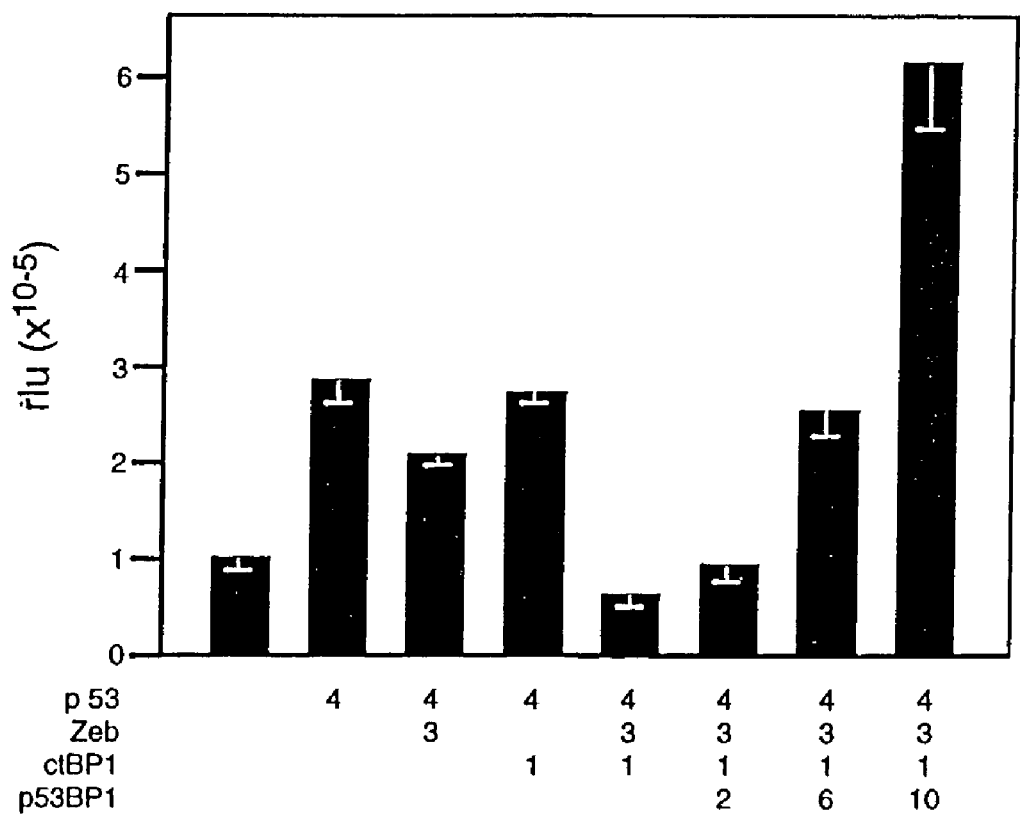
FIG. 2 shows that ZEB-CtBP1 mediated repression of the p21 promoter is relieved by co-expressed 53BP1. 2 micrograms of a p21-promoter-driven luciferase reporter was co-transfected into NIH 3T3 cells along with the indicated expression constructs. ZEB represses p53-mediated activation of this reporter nearly four-fold in the presence of its co-activator, CtBP1. 53BP1 relieves this repression and increasing amounts up-regulate the reporter two-fold above the levels seen with p53 alone. Results shown are the average of four separate transfections, error bars indicate standard errors of the mean. Amounts indicated below are micrograms. Rlu, relative light units.

To confirm the ZEB-p53BP-1 interaction in vitro, co-precipitation experiments were performed using bacterially-expressed, full-length ZEB fused to GST and an in vitro-translated (IVT), radio-labeled HA epitope-tagged p53BP1. Both the carboxy-terminal fragment (52 kD) and the full-length p53BP1 (217 kD) co-precipitated with ZEB as shown in FIG. 1C, lanes 4 and 6, respectively. The interaction of ZEB with full-length p53BP1 was competed away using purified, bacterially expressed, unlabeled HA-tagged carboxyl 53BP1 (52 kD) (FIG. 1B, lanes 6 and 7). Iwabuchi et al. demonstrated that p53BP1 can co-activate p53-mediated transcription (Iwabuchi et al., 1998, J. Biol. Chem. 273: 26061–26068). To test the functional consequences of the ZEB-p53BP1 interaction, we performed a series of transient transfections using a well-characterized p53 target promoter from the p21/WAF1 gene (Zeng and el-Deiry, 1996, Oncogene. 12:1557–1564). A luciferase reporter construct driven by this 2.3 kb promoter contains two binding sites for p53 at its 5' terminus and eight E-box (CANNTG) motifs (several of which can bind to ZEB in electrophoretic mobility shift assays, data not shown) distributed throughout the 3' half of this promoter. As seen in FIG. 2, ZEB repressed p53-mediated transactivation of the p21 promoter nearly four-fold (FIG. 2) when co-expressed with the co-repressor CtBP1 (53, 23). This repression could be overcome adding increasing amounts of 53BP1 (FIG. 2).

The yeast two hybrid screen also revealed that ZEB interacts with three additional proteins which play roles in diverse signal transduction pathways. ZEB binding partners identified also include: Homeodomain Interacting Protein Kinase 2 (HIPK2), S-adenosylhomocysteine hydrolase (AdoHcyase; S-adenosyl-L-homocystein hydrolase), and α-catenin. HIPK2 is a highly conserved serine/threonine kinase which localizes to the nucleus and is a component of a corepressor complex (Choi et al., 1999, J. Biol. Chem. 274:33194–33197; Kim et al., 1999, Proc. Natl. Acad. Sci. 96:12350–12355 Li et al., 2000, Biochem. Biophys. Res. Comm. 277:513–517; Wang et al., 2001, Biochim. Biophys Acta 1518:168–172). AdoHcyase is involved in the catabolism of S-adenosyl-L-homocysteine (AdoHcy) and, as such, has been implicated in a number of signaling pathways, including those related to cell viability, transformation, and drug resistance (Hershfield and Kredich, 1980, Proc. Natl. Acad. Sci. 77:4292–4296; Shatrov et al., 1999, Eur. Cytokine Netw. 10:247–252; Han et al., 1998, Arch. Pharm. Res. 21:378–384; Bemi et al., 1998, Int. J. Cancer 75:713–720). Alpha-catenin is a cytoplasmic protein which is a component of a complex that serves to anchor E-cadherin to the actin cytoskeleton. E-cadherin, the epithelium-specific cadherin, is known to play a major role in tumor progression in many human carcinomas, via intercellular homophilic Ca2+-dependent adhesion (Mialhe et al., 1997, Invasion Metastasis 17:124–137; Khare et al., 1999, Int. J. Oncol. 14:33–40).

The identification of ZEB binding partners in the two hybrid assay facilitates high throughput screening analyses to identify proteins, peptides, and/or compounds which modulate the interaction of ZEB with p53BP1, HIP2K, AdoHcyase, alpha-catenin. The identification of proteins, peptides, and/or compounds which modulate the interaction of ZEB with its binding partners provides additional tools that can be used in the treatment of cancers in which ZEB activity has been altered.

Dominant Negative ZEB causes Cells to Apoptose.

The ZEB-p53BP1 interaction, together with the dramatic (90%) reduction in the T-cell population in the ZEB knockout mouse (Higashi et al, 1997, J. Exp. Med. 185:1467–1479; Takagi et al., 1998, Development. 125: 21–31), prompted an investigation of the potential role(s) that ZEB might play in apoptosis. To test the hypothesis that ZEB may be repressing pro-apoptotic genes, the effect of expressing a dominant negative (dn) version of the ZEB protein on the expression patterns of ZEB target genes in T-cells was evaluated. To this end, the sequences encoding the DNA-binding carboxyl zinc-finger domain of ZEB were fused in frame at their 3' end to the sequence encoding green flourescent protein (GFP) as depicted in FIG. 3A. To create a dn ZEB, sequences encoding the GAL4 activation domain were fused to the 5' end of the ZEB sequence. The above described wild-type and dn ZEB constructs were then cloned into a tetracycline responsive vector (see Materials and Methods). To test their functional integrity, the transiently transfected NIH3T3 murine fibroblasts were monitored for green fluorescence after induction of fusion protein expression following exposure to the tetracycline analogue, doxycycline. Surprisingly, the GFP-positive cells carrying the dn ZEB, but not those GFP-positive cells carrying wild-type ZEB, displayed a classic apoptotic morphology, including cell shrinkage and membrane blebbing, within hours of doxycycline addition (data not shown). Given that the predominant phenotype of the ZEB knockout mouse suggests increased cell death in T cells and, to a lesser degree, osteoblasts (Takagi et al., 1998, Development. 125:21–31), the effects of the expression of dn ZEB in cells from these two lineages were evaluated. Similar to the NIH 3T3 fibroblasts, expression of dn ZEB construct in T cells (FIG. 3B, panel e) and the MC3T3 pre-osteoblast cell line (panel g) induced morphologic changes consistent with apoptosis. To demonstrate directly the activation of the cell-death program, doxycycline-treated cells were incubated with a cell-membrane permeable, rhodamine-labeled zVAD-FMK compound, which irreversibly binds and inhibits active caspases, thereby inhibiting apoptosis (see Materials and Methods). Both Jurkat and MC3T3 cells transfected with wild-type ZEB, displayed normal cell morphology (FIG. 3B, panels a and c, respectively), but no detectable rhodamine fluorescence (b and d). In striking contrast, the cells expressing dn ZEB were rhodamine-positive (panels f and h), indicating the presence of active caspases.

Antisense Oligomers Targeting Endogenous ZEB Cause Apoptosis.

To determine whether inhibition of endogenous ZEB also rendered cells vulnerable to apoptosis, cells were transfected with ZEB anti-sense or mis-sense morpholino-based oligonucleotides (in which the five-membered ribose ring of a traditional nucleotide is replaced with a nuclease-resistant, six-membered morpholine ring (Schmajuk et al., 1999, J. Biol. Chem. 274:21783–21789). These oligos are designed to base-pair with translation initiation sites and, via an RNAse H-independent mechanism, consequently inhibit the translation of target specific RNA (Thangaraju et al., 2000, J. Biol. Chem. 275:33487–33496). Both the ZEB anti-sense and mis-sense control oligonucleotides were labeled with flourescein at their 3' ends, so the recipient cells could be visualized in real time. NIH 3T3 cells treated with the anti-sense oligonucleotide displayed the apoptotic morphology shown in FIG. 4A. A fluorescence signal was also readily detected in NIH3T3 cells treated with the mis-sense control oligo, but the cells appeared essentially normal (FIG. 4, panel B). Western blot analysis of protein extracts from parallel oligonucleotide (anti-sense and mis-sense) treatments demonstrated a significant reduction in endogenous levels of ZEB protein in the anti-sense treated cells (FIG. 4C) as compared to controls. The expression of the internal control GAPDH was unaffected, thereby confirming the specificity of the inhibition of ZEB protein translation by the ZEB anti-sense oligonucleotide.

Expression of Wild-type ZEB Protects Cells from Radiation-induced Apoptosis.

Figure 5:
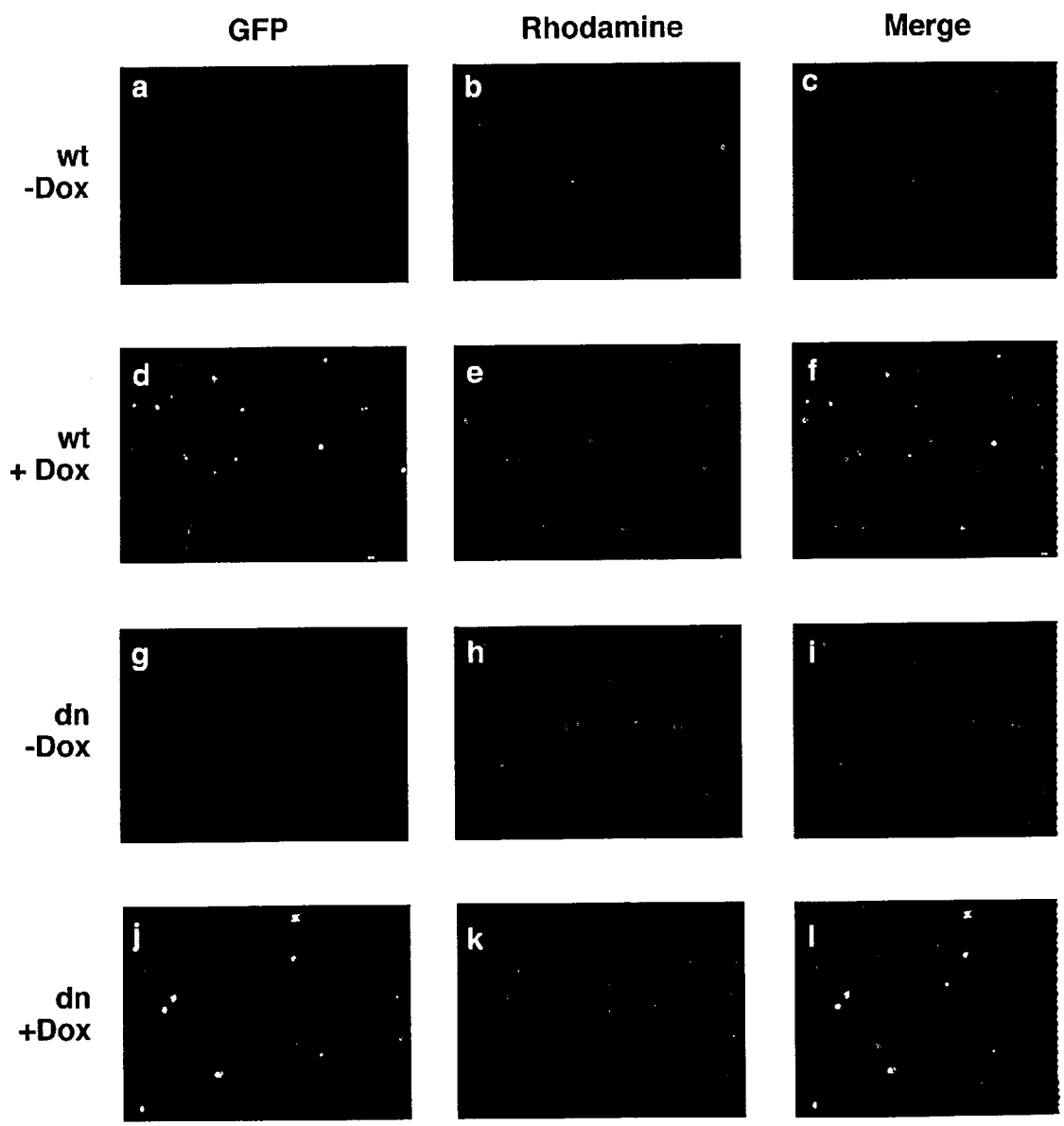
FIG. 5 shows that wild type ZEB is radioprotective, while dominant negative ZEB potentiates radiation-induced apoptosis in Jurkat cells. Cells stably transfected with a tetracycline-inducible tet-repressor-VP16 fusion construct, were transiently transfected with either wild-type ZEB fused to GFP (wt), or the dominant negative GAL4-ZEB-GFP (dnsee schematic in FIG. 3). 2 days later, doxycylcine (Dox, 2 mg/ml in the culture medium) was added to one of two pools of each transfection (the other pool received vehicle only (-Dox)), and the wt-transfected cells were incubated at 37° C. for another 48 hours, while the dn cells were incubated at 37° C. for 2 hours. Aliquots of cells were then subjected to gamma radiation at various doses, and returned to the incubator. Four hours following radiation treatment, the cells were tested for the presence of activated caspases using a rhodamine-coupled pan-caspase inhibitor VAD-FMK (see Materials and Methods). Cells were then cytospun onto microscope slides, and examined using flourescence microscopy. All cells depicted here received a dose of 10 Gy of radiation. a-c, cells transfected with wt ZEB-GFP with no induction, rhodamine-labeled cells are representative of radiation-induced background apotosis; d-f, induced wt ZEB-GFP (green cells) are not labeled by the caspase inhibitor; g-i, cells transfected with the dn construct with no induction, with a similar background of radiation-induced apoptosis; j-l, induced dn-transfected cells and apoptosing cells co-localize.
Figure 6:
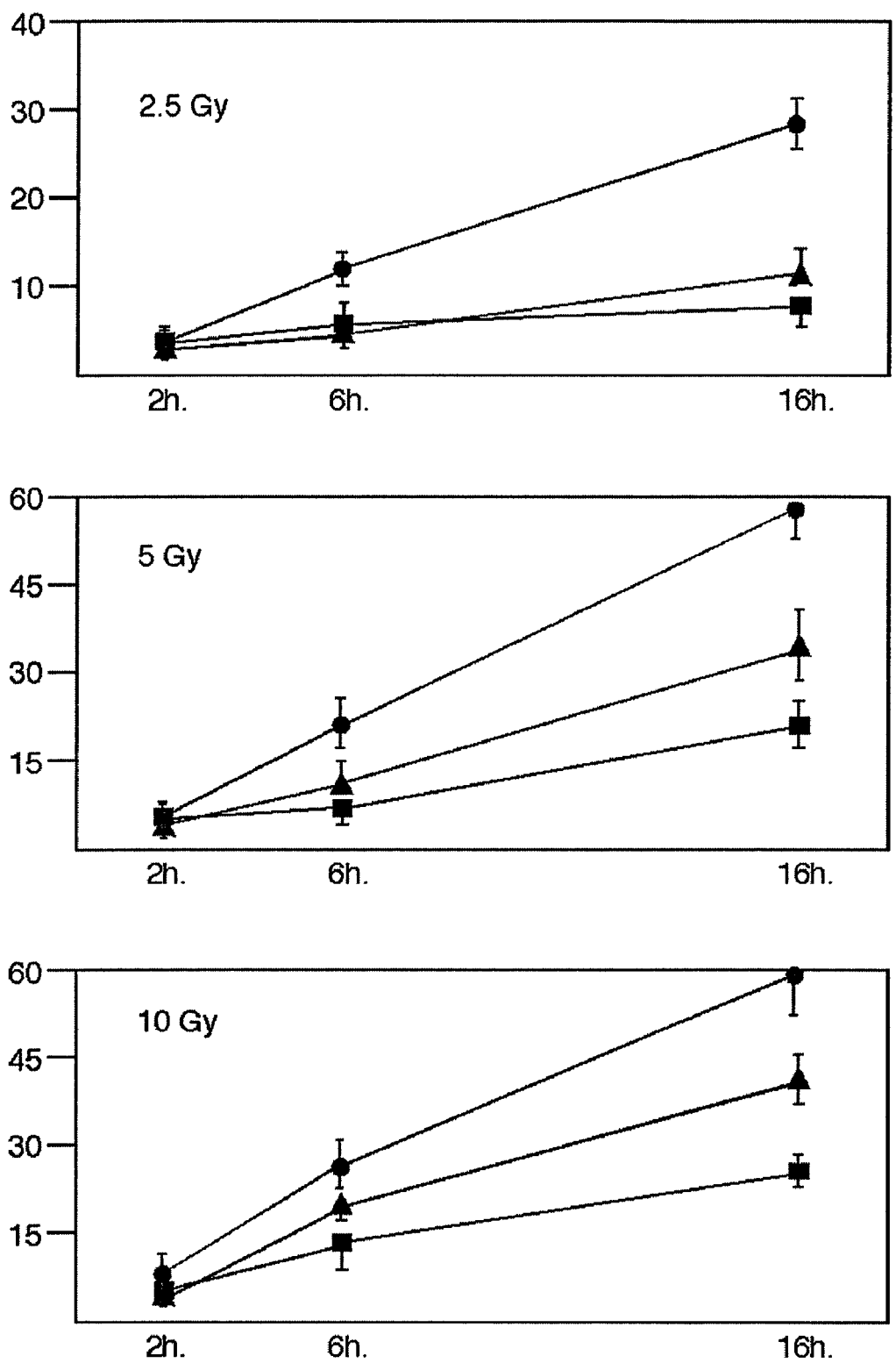
FIG. 6 reveals effects of wild type and dn ZEB constructs on ionizing radiation-induced apoptosis. Jurkat cells transfected with tetracycline-inducible wt or dn ZEB constructs were induced, and 48 hrs. (in the case of wt) or 4 hrs. (in the case of the dn construct) later were subjected to either 2.5, 5, or 10 Gy of gamma radiation. At 2 hrs, 6 hrs, and 16 hrs. post-irradiation, cells were assayed for the presence of active caspases as described in Materials and Methods, and observed via epi-flouresence microscopy. For each sample, 5 separate fields of 100 cells were scored for single (GFP) or double-positive (GFP and rhodamine) flourescence. The results of three separate experiments were averaged for each construct and are summarized in the graphs as percentages of apoptotic (rhodamine positive) cells, of all the cells in each counted field. Note the differences in the scale on the X-axis between the first graph and the second and third. Error bars represent standard errors of the mean. Red circles, dn construct; green triangles, GFP alone; black squares, wt construct.

Jurkat cells stably expressing the "Tet-ON" tetracycline repressor (Clontech, see Materials and Methods) were transiently transfected with a tetracycline-responsive expression vector harboring either wild-type ZEB-GFP fusion proteins or dn Gal4-ZEB-GFP fusion constructs (FIG. 3, panel A). Forty-eight hours later, the cells were treated with either doxycycline or diluent solution thereto, and returned to the incubator. Four hours post-induction, aliquots of each transfection were then subjected to various amounts of ionizing radiation and returned to the incubator to recover. Samples of each of the irradiated cells were removed at 2, 6, and 16 hours post-irradiation and assayed as above for active caspase activity (see FIG. 3; Materials and Methods). Representative fluorescent micrographs of the results are shown in FIG. 5, with a graphic representation of the overall results shown in FIG. 6. Sixteen hours after exposure to either 5 Gy or 10 Gy of gamma radiation, over-expression of wild-type ZEB (FIG. 6 squares) reduced the number of apoptosing cells by roughly 15% compared to that of control cells (triangles) expressing only GFP. Over-expression of dn ZEB had the opposite effect, increasing the fraction of cells undergoing apoptosis by an average of 20% over the entire range of radiation exposure (FIG. 6, compare circles to triangles). Expression of either the full length wildtype ZEB-GFP or wild-type carboxyl-ZEB-GFP construct provided virtually identical protection against apoptosis in this experiment.

Over-expression of SHP-1, a Negative Regulator of Cell Signaling, Inhibits Expression of ZEB.

Figure 7A:
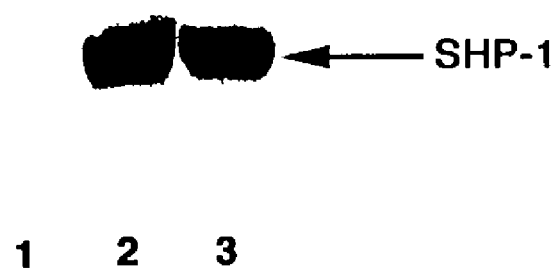
FIG. 7 reveals that ZEB is down-regulated in Jurkat cells over-expressing SHP-1. Jurkat cells were stably transfected with a SHP-1-expression vector, and individual clonal lines derived by limiting dilution (see Materials and Methods). (A) Representative western blot of cellular lysates from two stable lines. Lane 1, empty pcDNA3 expression vector; lane 2, stable line C4; lane 3, line G11. (B) RT-PCR analysis performed on total RNA isolated from the cell lines in (A). ZEB mRNA is significantly down-regulated (greater than ten-fold) in the SHP-1-expressing cell lines. Lane 1, parent non-transfected Jurkat line; lane 2, vector alone; lane 3, line C4; lane 4, line G11.
Figure 7B:
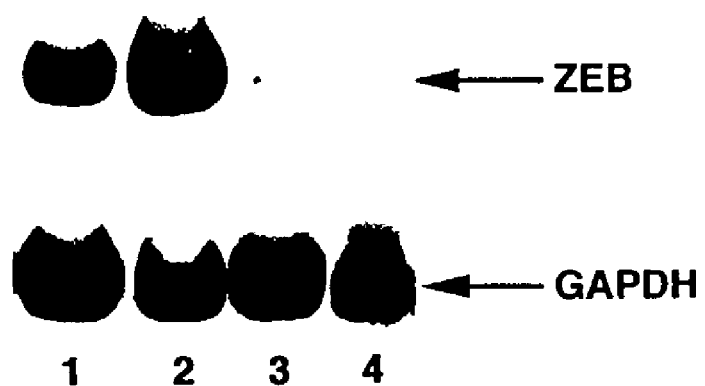

In hematopoietic cells, SHP-1 phosphatase is a key negative regulator of a number of receptor-mediated signaling pathways, including those of the immunoglobulin/T-cell receptor and cytokine receptor families (Kozlowski et al., 1993, J. Exp. Med. 178:2157–2163; Siminovitch et al., 1998, Semin. Immunol. 10:329–347). SHP-1 participates in the regulation of cellular activation, proliferation, differentiation, migration and survival (Lenardo et al., 1999, Annu. Rev. Immunol. 17:221–253; Matthews et al., 1992, Mol. Cell. Biol. 12:2396–2405; Kozlowski et al., 1993, J. Exp. Med. 178:2157–2163). The finding presented herein that ZEB displays anti-apoptotic activity, coupled with the dramatic reduction in the number of mature T cells in the ZEB knock-out mouse (Higashi et al, 1997, J. Exp. Med. 185: 1467–1479), led to the hypothesis that SHP-1 might regulate ZEB in the T-cell lineage. To test this hypothesis, Jurkat T cells (which express negligible levels of endogeneous SHP-1 mRNA; M. A. Wasik; unpublished data), were stably transfected with a SHP-1 expression vector or a control empty vector. The resulting expression of the SHP-1 protein in the transfected , as well as parental Jurkat cells, was determined by Western blot assay (FIG. 7A). Semi-quantitative RT-PCR assays were performed in parallel using RNA isolated from each of these lines to test for the relative levels of ZEB mRNA expression. As demonstrated by both assays, ZEB was down-regulated to nearly undetectable levels in all stable lines expressing detectable levels of SHP-1 (a total of 5 different, SHP-1-transfected Jurkat lines). The results from two such lines (along with the control parental and empty vector transfected lines) are shown in FIG. 7B. These findings indicate that SHP-1 is a negative regulator of ZEB expression in Jurkat human T cells.

Over-expression of SHP-1 in Jurkat Cells Increases their Sensitivity to Ionizing Radiation.

Figure 8B:
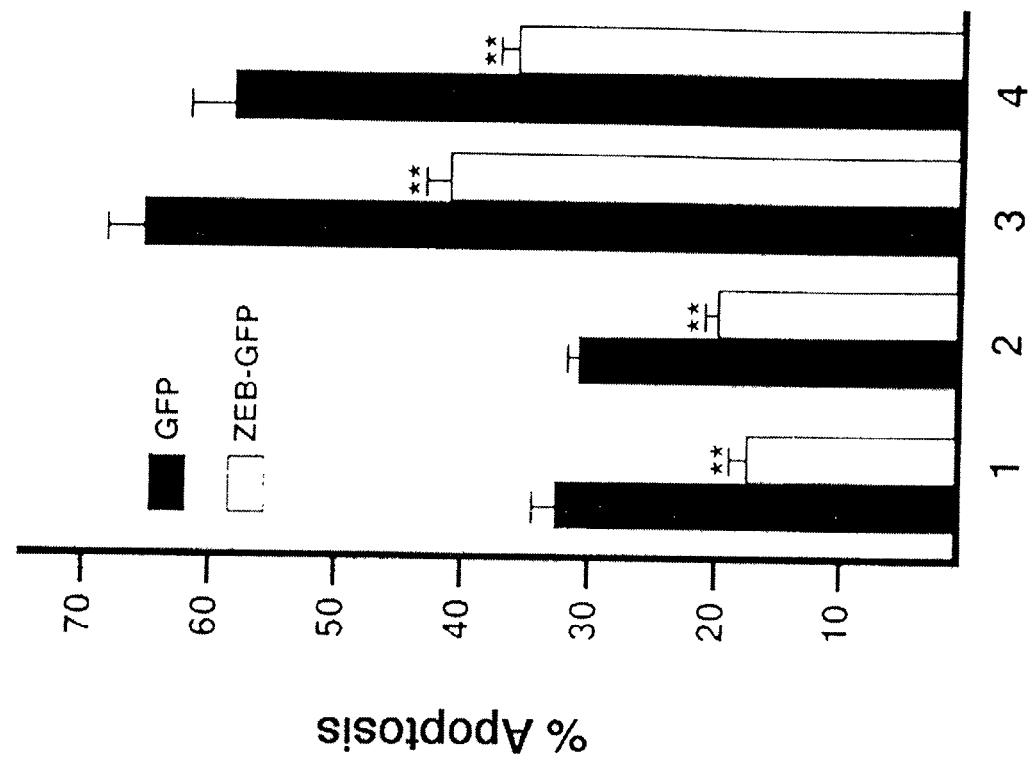
FIG. 8 shows that the enhanced sensitivity of SHP-1 over-expressing cells to ionizing radiation is restored to normal levels following expression of wild type ZEB. Results are depicted in (A) and (B) with histogram bars.
Figure 8A:
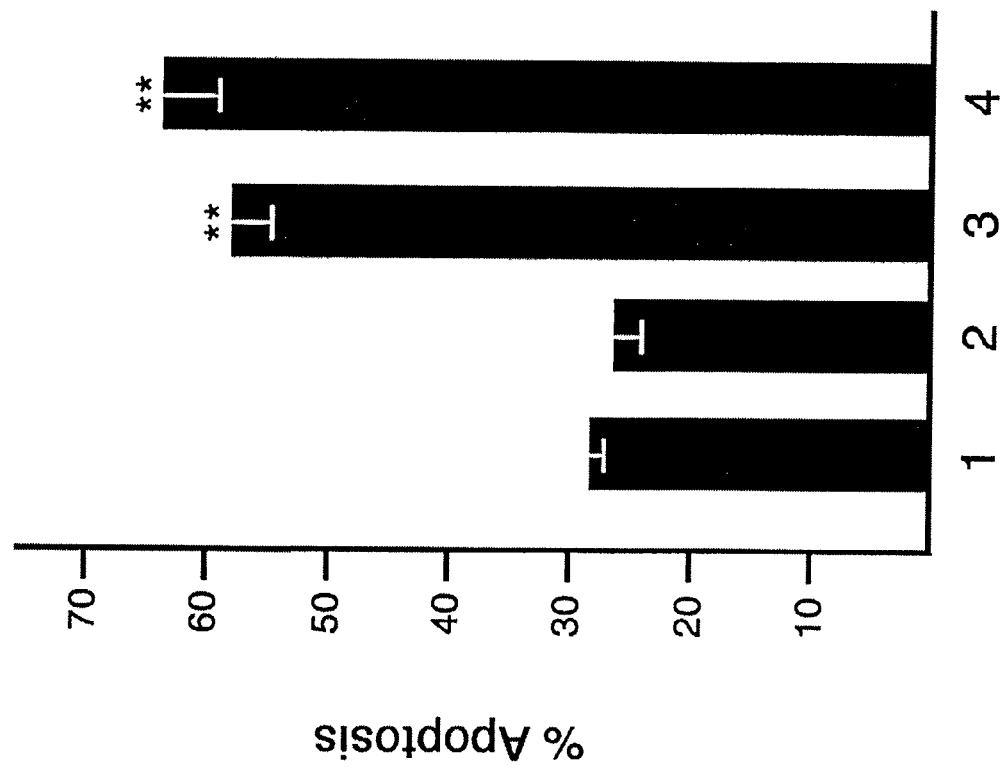

Over-expression of ZEB-1 protected Jurkat cells from ionizing radiation-induced programmed cell death, while reducing levels of the endogenous protein caused cells to apoptose. In view of the above results, an assessment was made of a potential correlation between the decreased levels of ZEB-1 mRNA in Jurkat cells stably transfected with SHP-1 phosphatase and an increase in their sensitivity to ionizing radiation. The parental Jurkat line, from which the stable SHP-1-expressing lines were derived, and a control cell line stably transfected with empty expression vector pcDNA 3 were roughly equivalent in their sensitivity to gamma irradiation; slightly less than one-third of these control cell populations underwent apoptosis following gamma irradiation (FIG. 8A, bars 1 and 2). As demonstrated by the number of cells undergoing apoptosis at a particular time after irradiation, both of the SHP-1-expressing lines tested were approximately twice as sensitive to gamma irradiation (FIG. 8A, bars 3 and 4).

Re-expression of ZEB-1 in SHP-1-over-expressing Stable Cell Lines Restores their Radio-resistance to Wild-type Levels.

To test whether the enhanced sensitivity of SHP-1 over-expressing cells could be restored to a normal (base-line) level of radio-resistance by rescue with ZEB-1, wild-type ZEB-1 was re-introduced into these cells. Each of the cell lines shown in FIG. 8B was transiently transfected with tetracycline-inducible vectors harboring either GFP alone or wild-type ZEB-1 fused to GFP and induced, irradiated and analysed as described herein (see Materials and Methods). All of the cells over-expressing GFP alone showed no alteration in their sensitivity to ionizing radiation (FIG. 8B, black bars). When transfected with the wtZEB-1-GFP construct, however, both of the SHP-1 over-expressing lines returned to their base-line levels of radio-resistance (FIG. 8B, white bars, colums 3 & 4). Consistent with the results described herein (FIGS. 2 & 3), a significant increase in the resistance of both of the control cell lines was also observed (FIG. 8B, white bars, columns 1 & 2).

EXAMPLE 2

ZEB mRNA expression levels in normal and transformed cells derived from a variety of different tissue types are described in the present example. The data obtained provide a framework for correlating modulations in ZEB mRNA expression levels to tumor stage.

TABLE I

Change in levels of ZEB mRNA in tumor versus normal tissue

| Tissue | Increase | Decrease | No Change | Percent |
|---|---|---|---|---|
| Stomach | 20 | 3 | 5 | 71% UP |
| Prostate | 3 | — | — | 100% UP |
| Ovary | 0 | 3 | 1 | 75% DOWN |
| Colon | 1 | 8 | — | 88% DOWN |
| Breast | 6 | 3 | — | 66% DOWN |

Table I provides a summary of data correlating relative levels of ZEB mRNA in tumor versus normal tissue biopsies. As can be seen modulation in levels of ZEB associated molecules varies with tissue types.

EXAMPLE 3

The cellular localization of ZEB protein is also a useful diagnostic indicator of the grade or stage of cancer. Staining of cell lines derived from melanoma patients at different stages of disease, for example, revealed that a correlation exists between translocation of ZEB protein from the cytoplasm to the nucleus and the degree of melanoma tumorigenicity (FIG. 13). These studies showed that ZEB protein was localized to the cytoplasm in a cell line taken from a patient with primary/radial growth phase (low grade, initial phase) melanoma. In a cell line taken from a patient with intermediate grade (vertical growth phase) melanoma, however, ZEB was expressed cell-wide. Significantly, ZEB was detected only in the nucleus of a cell line isolated from a patient with an advanced melanoma (metastatic growth phase). These studies revealed a correlation between ZEB cellular localization and severity of disease which provides a facile assay with which to define the stage of melanoma progression. In a particular embodiment of the present invention, nuclear localization of ZEB can be used as an indicator of late stage, advanced melanoma.

REFERENCES

1. Abbott, D. W., M. E. Thompson, C. Robinson-Benion , G. Tomlinson, R. A. Jensen, and J. T. Holt. 1999. BRCA1 expression restores radiation resistance in BRCA1-defective cancer cells through enhancement of transcription-coupled DNA repair. J. Biol. Chem. 274:18808–18812.
2. Ambrosini, G., C. Adida, D. C. Altieri. 1997. A novel anti-apoptosis gene, survivin, expressed in cancer and lymphoma. Nat Med. 3: 917–921.
3. Ambrosini, G., C. Adida, G. Sirugo, and D. C. Altieri. 1998. Induction of apoptosis and inhibition of cell proliferation by survivin gene targeting. J. Biol. Chem. 273:11177–11182.
4. Arch, R. H., R. W. Gedrich, and C. B. Thompson. 1998. Tumor necrosis factor receptor-associated factors (TRAFs)—a family of adapter proteins that regulates life and death. Genes Dev. 12: 2821–2830.
5. Arch R. H. and C. B. Thompson. 1999. Lymphocyte survival—the struggle against death. Annu. Rev. Cell. Dev. Biol. 15:113–140.
6. Arnold, H. H., and B. Winter. 1998. Muscle differentiation: more complexity to the network of myogenic regulators. Curr Opin Genet Dev. 8:539–544.
7. Ausubel, F. M., R. Brent, R. E. Kingston, D. D. Moore, J. G. Siedman, J. A. Smith, and K. Struhl. 1992. Current Protocols in Molecular Biology. John Wiley & Sons, Inc. New York, N.Y.
8. Bork, P., K. Hofmann, P, Bucher, A. F. Neuwald, S. F. Altschul, and E. V. Koonin. 1997. A superfamily of conserved domains in DNA damage-responsive cell cycle checkpoint proteins. FASEB J. 11: 68–76.
9. Brabletz, T, A. Jung, F. Hlubek , C. Lohberg, J. Meiler, U. Suchy, and T. Kirchner. 1999. Negative regulation of CD4 expression in T cells by the transcriptional repressor ZEB. Int Immunol. 11:1701–1708.
10. Brunet, A, J. Park, H. Tran, L. S. Hu, B. A. Hemmings, and M. E. Greenberg. 2001. Protein Kinase SGK Mediates Survival Signals by Phosphorylating the Forkhead Transcription Factor FKHRL1 (FOXO3a). Mol. Cell. Biol. 21:952–965.
11. Callebaut, I., and J. P. Mornon. 1997. From BRCA1 to RAP1: a widespread BRCT module closely associated with DNA repair. FEBS Lett. 400: 25–30.
12. Chapman, M. S., and I. M. Verma. 1996. Transcriptional activation by BRCA1. Nature. 382: 678–679.
13. Chen, F., D. Chang, M. Goh, S. A. Klibanov, M. Ljungman. 2000. Role of p53 in cell cycle regulation and apoptosis following exposure to proteasome inhibitors. Cell Growth Differ. 11: 239–246.
14. Cuevas, B, Y. Lu , S. Watt, R. Kumar, J. Zhang, K. A. Siminovitch, and G. B. Mills. 1999. SHP-1 regulates Lck-induced phosphatidylinositol 3-kinase phosphorylation and activity. J. Biol. Chem. 274: 27583–27589.
15. Deveraux Q. L, and J. C. Reed. 1999. IAP family proteins—suppressors of apoptosis. Genes Dev. 13:239–252.
16. Dragovich T, C. M. Rudin, and C. B. Thompson 1998. Signal transduction pathways that regulate cell survival and cell death. Oncogene. 17:3207–3213.
17. Earnshaw W. C., L. M. Martins, and S. H. Kaufmann. 1999. Mammalian caspases: structure, activation, substrates, and functions during apoptosis. Annu. Rev. Biochem. 68:383–424.
18. Eggert A, Broodeur G M, Ikegaki N. 2000. Relative quantitative RT-PCR protocol for TrkB expression in neuroblastoma using GAPD as an internal control. Biotechniques 28: 681–691.
19. el-Deiry, W. S. 1998. Regulation of p53 downstream genes. Semin Cancer Biol. 8: 345–357.
20. Fields, S., and O. Song. 1989. A novel genetic system to detect protein-protein interactions. Nature. 340: 245–6.
21. Fortini, M. E., Z. C. Lai, and G. M. Rubin. 1991. The Drosophila zfh-1 and zfh-2 genes encode novel proteins containing both zinc-finger and homeodomain motifs. Mech Dev. 34:113–122.
22. Funahashi, J., R. Sekido, K. Murai, Y. Kamachi, and H. Kondoh. 1993. Delta-crystallin enhancer binding protein delta EF1 is a zinc finger-homeodomain protein implicated in postgastrulation embryogenesis. Development. 119:433–446.
23. Furusawa, T., H. Moribe, H. Kondoh, and Higashi Y. 1999. Identification of CtBP1 and CtBP2 as corepressors of zinc finger-homeodomain factor deltaEF1. Mol. Cell. Biol. 19: 8581–8590.
24. Genetta, T., D. Ruezinsky, and T. Kadesch. 1994. Displacement of an E-box-binding repressor by basic helix-loop-helix proteins: implications for B-cell specificity of the immunoglobulin heavy-chain enhancer. Mol Cell Biol. 14:6153–6163.
25. Genetta, T., and T. Kadesch. 1996. Cloning of a cDNA encoding a mouse transcriptional repressor displaying striking sequence conservation across vertebrates. Gene. 169:289–290.
26. Gregoire, J. M., and P. H. Romeo. 1999. T-cell expression of the human GATA-3 gene is regulated by a non-lineage-specific silencer. J Biol Chem. Mar 274:6567–6578.
27. Grooteclaes, M. L., and S. M. Frisch. 2000. Evidence for a function of CtBP in epithelial gene regulation and anoikis. Oncogene. 19:3823–3828.
28. Healy, J. I. and C. C. Goodnow. 1998. Positive versus negative signaling by lymphocyte antigen receptors. Ann. Rev. Immunol. 16:645–670.
29. Hemavathy, K, S. C. Guru, J. Harris, J. D. Chen, and Y. T. Ip. 2000. Human Slug is a repressor that localizes to sites of active transcription. Mol. Cell. Biol. 20: 5087–5095.
30. Hengartner, M. O. 2000. The biochemistry of apoptosis. Nature 407:770–776.
31. Higashi, Y., H. Moribe, T. Takagi, R. Sekido, K. Kawakami, H. Kikutani, and H. Kondoh. 1997 Impairment of T cell development in deltaEF1 mutant mice. J. Exp. Med. 185:1467–1479.
32. Hu, Y. F., Z. L. Hao, and R. Li. 1999. Chromatin remodeling and activation of chromosomal DNA replication by an acidic transcriptional activation domain from BRCA1. Genes Dev. 13: 637–642.
33. Huyton, T., P. A. Bates, X. Zhang, M. J. Sternberg, and P. S. Freemont. 2000. The BRCA1 C-terminal domain: structure and function. Mutat. Res. 460: 319–332.
34. Inukai, T., A. Inoue, H. Kurosawa, K. Goi, T. Shinjyo, K. Ozawa, M. Mao, T. Inaba, and A. T. Look. 1999. SLUG, a ces-1-related zinc finger transcription factor gene with antiapoptotic activity, is a downstream target of the E2A-HLF oncoprotein. Mol. Cell. 4: 343–352.

35. Iwabuchi, K., P. L. Bartel, B. Li, R. Marraccino, and S. Fields. 1994. Two cellular proteins that bind to wild-type but not mutant p53. Proc. Natl. Acad. Sci. (USA). 91: 6098–6102

36. Iwabuchi, K., B. Li, T. J. Massa, B. J. Trask, T. Date, and S. Fields. 1998. Stimulation of p53-mediated transcriptional activation by the p53-binding proteins, 53BP1 and 53BP2. J. Biol. Chem. 273: 26061–26068.

37. Jacobson M. D., M. Weil, and M. C. Raff. 1997. Programmed cell death in animal development. Cell. 88:347–354.

38. Kozlowski, M., I. Mlinaric-Rascan, G. S. Feng, R. Shen, T. Pawson, and K. A. Siminovitch. 1993. Expression and catalytic activity of the tyrosine phosphatase PTP1C is severely impaired in motheaten and viable motheaten mice. J. Exp. Med. 178:2157–2163.

39. Lai, Z. C., M. E. Fortini, and G. M. Rubin 1991. The embryonic expression patterns of zfh-1 and zfh-2, two Drosophila genes encoding novel zinc-finger homeodomain proteins. Mech Dev. 34:123–134.

40. Lakin, N. D., and S. P. Jackson. 1999. Regulation of p53 in response to DNA damage. Oncogene. 18:7644–7655.

41. Lassar A. B., R. L. Davis, W. E. Wright, T. Kadesch, C. Murre, A. Voronova, D. Baltimore, and H. Weintraub. 1991. Functional activity of myogenic HLH proteins requires hetero-oligomerization with E12/E47-like proteins in vivo. Cell. 66:305–315.

42. Lee, J. E. 1997. Basic helix-loop-helix genes in neural development. Curr Opin Neurobiol. 7:13–20.

43. Lenardo, M. K. M. Chan, F. Hornung, H. McFarland, R. Siegel, J. Wang, and L. Zheng. 1999. Mature T lymphocyte apoptosis—immune regulation in a dynamic and unpredictable antigenic environment. Annu. Rev. Immunol. 17: 221–253.

44. Lopez, C. D., Y. Ao, L. H. Rohde, T. D. Perez, D. J. O'Connor, X. Lu, J. M. Ford, and L. Naumovski. 2000. Proapoptotic p53-interacting protein 53BP2 is induced by UV irradiation but suppressed by p53. Mol. Cell. Biol. 20: 8018–8025.

45. Matthews, R. J., D. B. Bowne, E. Flores, M. L. Thomas. 1992. Characterization of hematopoietic intracellular protein tyrosine phosphatases: description of a phosphatase containing an SH2 domain and another enriched in proline-, glutamic acid-, serine-, and threonine-rich sequences. Mol. Cell. Biol. 12:2396–2405.

46. Miyake, T., Y. F. Hu, D. S. Yu, and R. Li. 2000. A functional comparison of BRCA1 C-terminal domains in transcription activation and chromatin remodeling. J. Biol. Chem. 275: 40169–40173.

47. Monteiro, A. N., A. August, and H. Hanafusa. 1996. Evidence for a transcriptional activation function. Proc. Natl. Acad. Sci. (U.S.A.) 93:13595–13599.

48. Naumovski, L, and M. L. Cleary. 1996. The p53-binding protein 53BP2 also interacts with Bc12 and impedes cell cycle progression at G2/M. Mol Cell Biol. 16:3884–3892.

49. Nijhawan D, Honarpour N, Wang X. 2000. Apoptosis in neural development and disease. Annu. Rev. Neurosci. 23:73–87.

50. Plas, D. R., R. Johnson, J. T. Pingel, R. J. Matthews, M. Dalton, G. Roy, A. C. Chan, and M. L. Thomas. 1996. Direct regulation of ZAP-70 by SHP-1 in T cell antigen receptor signaling. Science. 272:1173–1176.

51. Ono, M., H. Okada, S. Bolland, S. Yanagi, T. Kurosaki, and J. V. Ravetch. 1997. Deletion of SHIP or SHP-1 reveals two distinct pathways for inhibitory signaling. Cell. 90: 293–301.

52. Postigo, A. A., and, Dean D. C. ZEB, a vertebrate homolog of Drosophila Zfh-1, is a negative regulator of muscle differentiation. EMBO J. 1997 16:3935–3943.

53. Postigo, A. A., D. C. Dean. 1999. ZEB represses transcription through interaction with the co-repressor CtBP. Proc. Natl. Acad. Sci. (U.S.A.) 96:6683–6688.

54. Postigo A A, Dean D C. 2000. Differential expression and function of members of the zfh-1 family of zinc finger/homeodomain repressors. Proc. Natl. Acad. Sci. (U.S.A.) 97: 6391–6396.

55. Postigo, A. A., E, Ward, J. B. Skeath, and D. C. Dean. 1999. zfh-1, the Drosophila homologue of ZEB, is a transcriptional repressor that regulates somatic myogenesis. Mol. Cell. Biol. 19:7255–7263.

56. Prabhu, S., A. Ignatova, S. T. Park, and X. H. Sun. 1997. Regulation of the expression of cyclin-dependent kinase inhibitor p21 by E2A and Id proteins. Mol Cell. Biol. 17: 5888–5896.

57. Qian, D. and A. Weiss. 1997. T cell antigen receptor signal transduction. Curr. Opin. Cell Biol. 9: 205–212.

58. Rathmell, J. C., and C. B. Thompson. 1999. The central effectors of cell death in the immune system. Annu Rev Immunol. 17:781–828.

59. Reed, C. J. 2000. Apoptosis and cancer: strategies for integrating programmed cell death. Semin. Hematol. 37:9–16.

60. Rudin C. M., and C. B. Thompson. 1997. Apoptosis and disease: regulation and clinical relevance of programmed cell death. Annu. Rev. Med. 48:267–281.

61. Sakamuro, D., and G. C. Prendergast. 1999. New Myc-interacting proteins: a second Myc network emerges. Oncogene. 18: 2942–2954.

62. Sebzda, E., S. Mariathasan, T. Ohteki, R. Jones, M. F. Bachmann, and P. S. Ohashi. Selection of the T cell repertoire. 1999. Annu. Rev. Immunol. 17:829–874.

63. Sekido, R., K. Murai, J. Funahashi, Y. Kamachi, A. Fujisawa-Sehara, Y. Nabeshima, and H. Kondoh. The delta-crystallin enhancer-binding protein delta EF1 is a repressor of E2-box-mediated gene activation. Mol Cell Biol. 1994 14:5692–5700.

64. Schmajuk, G., H. Sierakowska, and R. Kole. 1999. Antisense oligonucleotides with different backbones. Modification of splicing pathways and efficacy of uptake. J. Biol. Chem. 274: 21783–21789.

65. Schultz, L. B., N. H. Chehab, A. Malikzay, and T. D. Halazonetis. 2000. p53 Binding Protein 1 (53BP1) Is an Early Participant in the Cellular Response to DNA Double-Strand Breaks. J. Cell. Biol. 151:1381–1390.

66. Sensenbaugh, K. R., and M. M. Sanders. Multiple promoter elements including a novel repressor site modulate expression of the chick ovalbumin gene. DNA Cell Biol. 1999 18:147–156.

67. Sheikh, M. S., and A. J. Fornace, Jr. 2000. Role of p53 family members in apoptosis. J. Cell. Physiol. 182:171–181.

68. Siminovitch, K. A., and B. G. Neel. 1998. Regulation of B cell signal transduction by SH2-containing protein-tyrosine phosphatases. Semin. Immunol. 10: 329–347.

69. Takagi, T., H. Moribe, H. Kondoh, and Y. Higashi. 1998. DeltaEF1, a zinc finger and homeodomain transcription factor, is required for skeleton patterning in multiple lineages. Development. 125:21–31.

70. Taylor, M. F., J. D. Paulauskis, D. D. Weller, and L. Kobzik. 1996. In vitro efficacy of morpholino-modified antisense oligomers directed against tumor necrosis factor-alpha mRNA. J. Biol. Chem. 271: 17445–17452.

71. Thangaraju, M., S. H. Kaufmann, and F. J. Couch. 2000. BRCA1 facilitates stress-induced apoptosis in breast and ovarian cancer cell lines. J Biol Chem. 275: 33487–33496.
72. Wang H. G., and J. C. Reed. 1998. Mechanisms of Bcl-2 protein function. Histol Histopathol. 13:521–30.
73. Wang, X. W. 1999. Role of p53 and apoptosis in carcinogenesis. Anticancer Res. 19: 4759–4771.
74. Watanabe Y, K. Kawakami, Y. Hirayama , and K. Nagano. Transcription factors positively and negatively regulating the Na, K-ATPase alpha 1 subunit gene. J Biochem (Tokyo). 1993 114:849–855.
75. Weber, B. L., K. J. Abel, F. J. Couch, S. Merajver, L. Castilla, L. C. Brody, and F. S. Collins. 1995. Transcript identification in the BRCA1 candidate region. Breast Cancer Res. Treat. 33:115–124.
76. Welcsh, P. L., Owens K. N., and M. C. King. 2000. Insights into the functions of BRCA1 and BRCA2. Trends Genet. 16:69–74.
77. Williams T. M., D. Moolten, J. Burlein, J. Romano, R. Bhaerman, A. Godillot, M. Mellon, F. J. Rauscher 3d, and J. A. Kant. Identification of a zinc finger protein that inhibits IL-2 gene expression. Science. 1991 254:1791–1794.
78. Xia, Z., J. C. Morales, W. G. Dunphy, and P. B. Carpenter. 2000. Negative cell cycle regulation and DNA-damage inducible phosphorylation of the BRCT protein 53BP1. J. Biol. Chem. [epub. ahead of print]
79. Yasui, D. H, T. Genetta , T. Kadesch, T. M. Williams, S. L. Swain, L. V. Tsui and B. T. Huber. Transcriptional repression of the IL-2 gene in Th cells by ZEB. J Immunol. 1998.160:4433–4440.
80. Zhang, Q., P. N. Raghunath, E. Vonderheid, N. Odum and M. A. Wasik. 2000. Lack of phosphotyrosine phosphatase SHP-1 expression in malignant T-cell lymphoma cells results from methylation of the SHP-1 promoter. Am J Pathol. 157:1137–1146.
81. Zhang, X., S. Morera, P. A. Bates, P. C. Whitehead, A. I. Coffer, K. Hainbucher, R. A. Nash, M. J. Sternberg, T. Lindahl, and P. S. Freemont. 1998. Structure of an XRCC1 BRCT domain: a new protein-protein interaction module. EMBO J. 17: 6404–6411.
82. Zeng, Y. X., and W. S. el-Deiry. 1996. Regulation of p21WAF1/CIP expression by p53-independent pathways. Oncogene. 12:1557–1564.

It will be appreciated by those skilled in the art that changes could be made to the embodiments described above without departing from the broad inventive concept thereof. It is understood, therefore, that this invention is not limited to the particular embodiments disclosed, but includes modifications within the spirit and scope of the present invention as defined by the appended claims.

What is claimed is:

1. A method of diagnosing a cancer or a tumor in a mammal, said method comprising
   a) obtaining a biological sample from said mammal;
   b) contacting said sample with a composition comprising one or more ZEB specific detection reagent in an amount effective to permit detection and quantitation of a ZEB polypeptide, if present, in said sample, wherein said ZEB polypeptide is selected from the group consisting of SEQ ID NO: 10, the amino acid sequence encoded by nucleotides 2537 to 3473 of SEQ ID NO: 9, and the amino acid sequence encoded by nucleotides 481 to 1132 of SEQ ID NO: 9;
   c) determining from b) one or more of the amount and the sub-cellular location of said ZEB polypeptide; and
   d) determining from c) altered expression levels and/or localization of said ZEB polypeptide relative to normal control samples, thereby diagnosing a cancer or a tumor in said mammal.

2. A method as claimed in claim 1, wherein said cancer is of epithelial origin.

3. A method as claimed in claim 1, wherein said cancer is selected from the group consisting of melanoma, stomach, prostate, ovary, colon or breast cancer.

4. A kit for diagnosing and/or staging a tumor in a mammal, said kit comprising:
   a) a container for storing a biological sample obtained from said mammal, said sample comprising cells or tissues;
   b) a normal control biological sample for comparison to the sample obtained said mammal;
   c) a composition comprising one or more ZEB-specific detection reagents in an amount effective to permit detection of a ZEB polypeptide if present, in said sample, wherein said ZEB polypeptide is selected from the group consisting of SEQ ID NO: 10, the amino acid sequence encoded by nucleotides 2537 to 3473 of SEQ ID NO: 9, and the amino acid sequence encoded by nucleotides 481 to 1132 of SEQ ID NO: 9; and
   d) an instructional material setting forth a protocol suitable for use in detection and quantifying said ZEB polypeptide.

5. A kit as claimed in claim 4, wherein said ZEB-specific detection reagent is selected from the group consisting of antibodies or fragments thereof which have specific binding for said ZEB polypeptide.

* * * * *